United States Patent
Cha et al.

(10) Patent No.: US 9,972,785 B2
(45) Date of Patent: May 15, 2018

(54) SPIRO-TYPE COMPOUND AND ORGANIC LIGHT EMITTING ELEMENT COMPRISING SAME

(71) Applicant: LG Chem, Ltd., Seoul (KR)

(72) Inventors: Yongbum Cha, Daejeon (KR); Jin Joo Kim, Daejeon (KR); Sang Duk Suh, Daejeon (KR); Jungbum Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days. days.

(21) Appl. No.: 15/543,312

(22) PCT Filed: Oct. 12, 2016

(86) PCT No.: PCT/KR2016/011418
§ 371 (c)(1),
(2) Date: Jul. 13, 2017

(87) PCT Pub. No.: WO2017/073931
PCT Pub. Date: May 4, 2017

(65) Prior Publication Data
US 2018/0006233 A1 Jan. 4, 2018

(30) Foreign Application Priority Data

Oct. 28, 2015 (KR) .................. 10-2015-0150335
Oct. 10, 2016 (KR) .................. 10-2016-0130746

(51) Int. Cl.
*H01L 51/50* (2006.01)
*H01L 51/00* (2006.01)
(Continued)

(52) U.S. Cl.
CPC ........ *H01L 51/0056* (2013.01); *C07D 209/08* (2013.01); *C07D 209/86* (2013.01); *C07D 213/16* (2013.01); *C07D 215/06* (2013.01); *C07D 235/18* (2013.01); *C07D 239/26* (2013.01); *C07D 239/74* (2013.01); *C07D 251/24* (2013.01); *C07D 263/57* (2013.01);
(Continued)

(58) Field of Classification Search
CPC .. C07D 209/86; C07D 333/76; C07D 219/08; C07D 307/91; H01L 51/50
See application file for complete search history.

(56) References Cited

U.S. PATENT DOCUMENTS

| | | | |
|---|---|---|---|
| 2004/0251816 A1 | 12/2004 | Leo et al. | |
| 2012/0298203 A1 | 11/2012 | Ikeda et al. | |
| 2016/0308129 A1* | 10/2016 | Stoessel | C09K 11/06 |

FOREIGN PATENT DOCUMENTS

| | | |
|---|---|---|
| CN | 102532002 A | 7/2012 |
| CN | 104592978 A | 5/2015 |

(Continued)

OTHER PUBLICATIONS

Search report from International Application No. PCT/KR2016/011418, dated Jan. 20, 2017.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification provides a compound having a spiro structure, and an organic light emitting device including the same.

17 Claims, 1 Drawing Sheet

(51) Int. Cl.

| | | |
|---|---|---|
| *C09K 11/02* | (2006.01) | |
| *C07D 239/26* | (2006.01) | |
| *C07D 213/16* | (2006.01) | |
| *C07D 239/74* | (2006.01) | |
| *C07D 209/86* | (2006.01) | |
| *C07F 9/53* | (2006.01) | |
| *C07D 235/18* | (2006.01) | |
| *C07D 307/91* | (2006.01) | |
| *C07D 333/76* | (2006.01) | |
| *C07D 215/06* | (2006.01) | |
| *C07D 209/08* | (2006.01) | |
| *C07D 263/57* | (2006.01) | |
| *C07D 277/66* | (2006.01) | |
| *C07D 307/36* | (2006.01) | |
| *C07D 333/08* | (2006.01) | |
| *C07D 271/107* | (2006.01) | |
| *C07D 285/12* | (2006.01) | |
| *C07D 279/22* | (2006.01) | |
| *C07D 265/38* | (2006.01) | |
| *C09K 11/06* | (2006.01) | |
| *C07D 251/24* | (2006.01) | |
| *H01L 51/52* | (2006.01) | |

(52) U.S. Cl.
CPC ....... *C07D 265/38* (2013.01); *C07D 271/107* (2013.01); *C07D 277/66* (2013.01); *C07D 279/22* (2013.01); *C07D 285/12* (2013.01); *C07D 307/36* (2013.01); *C07D 307/91* (2013.01); *C07D 333/08* (2013.01); *C07D 333/76* (2013.01); *C07F 9/5325* (2013.01); *C09K 11/025* (2013.01); *C09K 11/06* (2013.01); *H01L 51/006* (2013.01); *H01L 51/007* (2013.01); *H01L 51/0058* (2013.01); *H01L 51/0061* (2013.01); *H01L 51/0065* (2013.01); *H01L 51/0067* (2013.01); *H01L 51/0068* (2013.01); *H01L 51/0069* (2013.01); *H01L 51/0071* (2013.01); *H01L 51/0072* (2013.01); *H01L 51/0073* (2013.01); *H01L 51/0074* (2013.01); *H01L 51/0077* (2013.01); *H01L 51/0085* (2013.01); *C09K 2211/1007* (2013.01); *C09K 2211/1022* (2013.01); *C09K 2211/1029* (2013.01); *C09K 2211/181* (2013.01); *C09K 2211/185* (2013.01); *H01L 51/001* (2013.01); *H01L 51/0054* (2013.01); *H01L 51/5016* (2013.01); *H01L 51/5056* (2013.01); *H01L 51/5076* (2013.01); *H01L 51/5088* (2013.01); *H01L 51/5092* (2013.01); *H01L 51/5096* (2013.01); *H01L 51/5206* (2013.01); *H01L 51/5221* (2013.01)

(56) References Cited

FOREIGN PATENT DOCUMENTS

| | | |
|---|---|---|
| KR | 20110002156 A | 1/2011 |
| KR | 20140021969 A | 2/2014 |
| KR | 101560102 B1 | 10/2015 |
| KR | 20160126399 A | 11/2016 |
| WO | 2003012890 A2 | 2/2003 |
| WO | 2008140134 A1 | 11/2008 |
| WO | 2011093067 A1 | 8/2011 |

OTHER PUBLICATIONS

Kim, Ji-Young, et al., "Orange Phosphorescent Organic Light-emitting Diodes Using New Spiro[benzoanthracene-fluorene]-Type Host Materials," Dyes and Pigments [Electronic publishing] Jan. 27, 2012, vol. 94, pp. 304-313.
Written Opinion of the International Searching Authority from PCT/KR2016/011418, dated Jan. 20, 2017.
Search Report from International Application No. PCT/KR2016/011421, dated Jan. 23, 2017.
Written Opinion of the International Searching Authority for PCT/KR2016/011421, dated Jan. 23, 2017.

* cited by examiner

【FIG. 1】
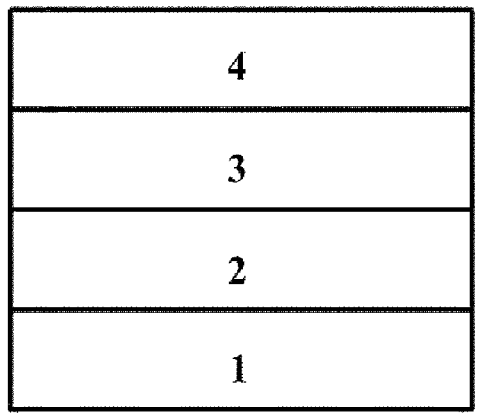
【FIG. 2】
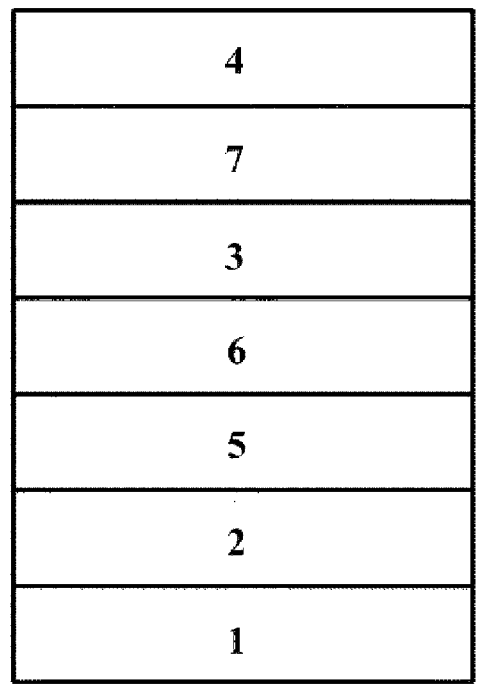

SPIRO-TYPE COMPOUND AND ORGANIC LIGHT EMITTING ELEMENT COMPRISING SAME

CROSS-REFERENCE TO RELATED APPLICATIONS

The present application is a national phase entry under 35 U.S.C. §371 of International Application No. PCT/KR2016/011418 filed Oct. 12, 2016, published May 4, 2017, which claims priority to Korean Patent Application No. 10-2015-0150335, filed Oct. 28, 2015, and Korean Patent Application No. 10-2016-0130746, filed Oct. 10, 2016, all of which are incorporated herein by reference.

TECHNICAL FIELD

The present specification relates to a compound having a spiro structure and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a compound having a spiro structure and an organic light emitting device including the same.

Technical Solution

One embodiment of the present specification provides a compound represented by the following Chemical Formula 1:

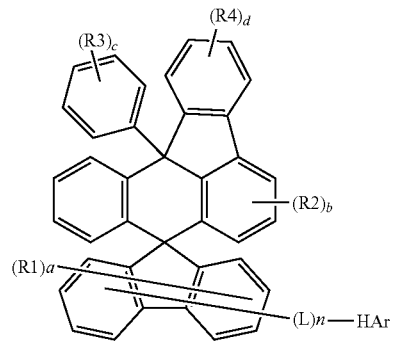

[Chemical Formula 1]

In Chemical Formula 1,

L is a direct bond, a substituted or unsubstituted arylene group; or a substituted or unsubstituted heteroarylene group, HAr is a substituted or unsubstituted heterocyclic group; or a substituted or unsubstituted phosphine oxide group, R1 to R4 are the same as or different from each other, and each independently hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may bond to an adjacent group to form a substituted or unsubstituted ring, a is an integer of 0 to 7, b is an integer of 0 to 7, c is an integer of 0 to 5, d is an integer of 0 to 4, n is an integer of 0 to 10, and when a, b, c, d and n are each 2 or greater, structures in the parentheses are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

Compounds described in the present specification can be used as a material of an organic material layer of an organic light emitting device. Compounds according to at least one embodiment are capable of enhancing efficiency, low driving voltage and/or enhancing lifespan properties in an organic light emitting device. Particularly, compounds described in the present specification can be used as a material of hole injection, hole transfer, hole injection and hole transfer, light emission, electron transfer or electron injection. In addition, compounds described in the present specification can be preferably used as a material of a light emitting layer, electron transfer or electron injection. More preferably, when using compounds described in the present specification as a material of hole injection, hole transfer and electron suppression layer, properties of low voltage, high efficiency and/or long lifespan are exhibited.

DESCRIPTION OF DRAWINGS

FIG. 1 illustrates an organic light emitting device formed with a substrate (1), an anode (2), a light emitting layer (3) and a cathode (4).

FIG. 2 illustrates an organic light emitting device formed with a substrate (1), an anode (2), a hole injection layer (5), a hole transfer layer (6), a light emitting layer (3), an electron transfer layer (7) and a cathode (4).

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in more detail.

One embodiment of the present specification provides a compound represented by Chemical Formula 1.

Examples of the substituents are described below, however, the substituents are not limited thereto.

In the present specification, the term "substituted or unsubstituted" means being substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group unsubstituted or substituted with an alkyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In one embodiment of the present specification, the expression "substituted or unsubstituted" may mean being preferably substituted with one or more substituents selected from the group consisting of deuterium; a halogen group; a nitrile group; an alkyl group; a trimethylsilyl group; an aryl group; and a heterocyclic group, or being unsubstituted.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the number of carbon atoms of the carbonyl group is not particularly limited, but is preferably from 1 to 40. Specifically, compounds having structures as below may be included, however, the carbonyl group is not limited thereto.

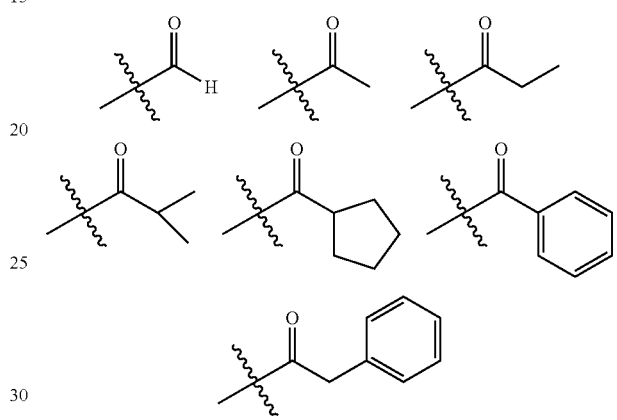

In the present specification, in the ester group, the oxygen of the ester group may be substituted with a linear, branched or cyclic alkyl group having 1 to 25 carbon atoms, or an aryl group having 6 to 25 carbon atoms. Specifically, compounds having the following structural formulae may be included, however, the ester group is not limited thereto.

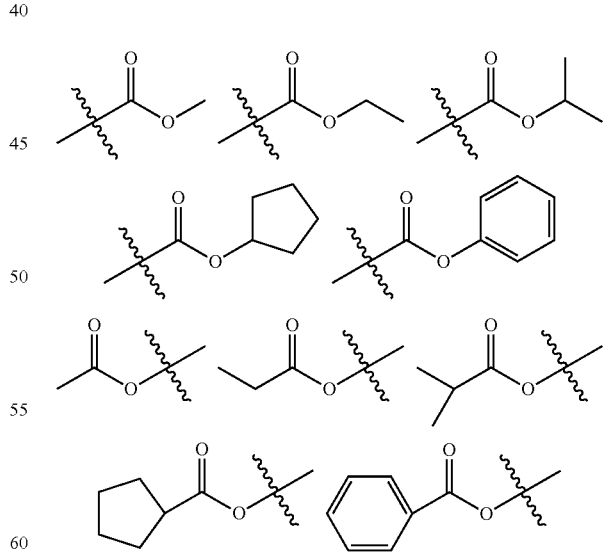

In the present specification, the number of carbon atoms of the imide group is not particularly limited, but is preferably from 1 to 25. Specifically, compounds having structures as below may be included, however, the imide group is not limited thereto.

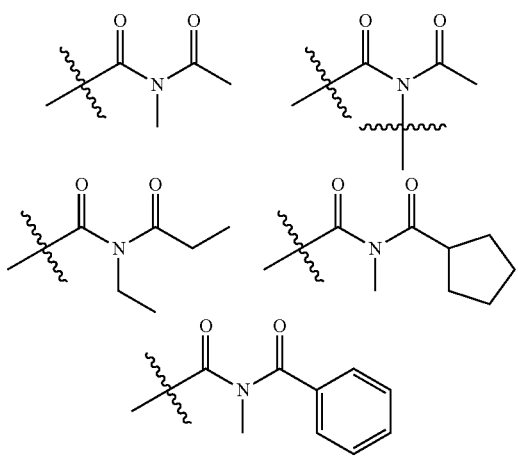

In the present specification, the silyl group may be represented by the chemical formula of —SiRR'R", and R, R' and R" may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —BRR', and R and R' may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, examples of the halogen group may include fluorine, chlorine, bromine or iodine.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to still another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group is not particularly limited, but preferably has 1 to 40 carbon atoms. According to one embodiment, the number of carbon atoms of the alkoxy group is from 1 to 10. According to another embodiment, the number of carbon atoms of the alkoxy group is from 1 to 6. Specific examples of the alkoxy group may include a methoxy group, an ethoxy group, a propoxy group, an isobutyloxy group, a sec-butyloxy group, a pentyloxy group, an iso-amyloxy group, a hexyloxy group and the like, but are not limited thereto.

In the present specification, the number of carbon atoms of the amine group is not particularly limited, but is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups.

Specific examples of the arylamine group may include a phenylamine group, a naphthylamine group, a biphenylamine group, an anthracenylamine group, a 3-methylphenylamine group, a 4-methylnaphthylamine group, a 2-methylbiphenylamine group, a 9-methylanthracenylamine group, a diphenylamine group, a phenylnaphthylamine group, a ditolylamine group, a phenyltolylamine group, carbazole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both monocyclic heterocyclic groups and multicyclic heterocyclic groups.

In the present specification, the arylheteroarylamine group means an amine group substituted with an aryl group and a heterocyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl groups.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. Examples of the monocyclic aryl group may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group, a triphenylene group and the like, but are not limited thereto.

In the present specification, the fluorenyl group may be substituted, and two of the substituents may bond to each other to form a spiro structure.

When the fluorenyl group is substituted,

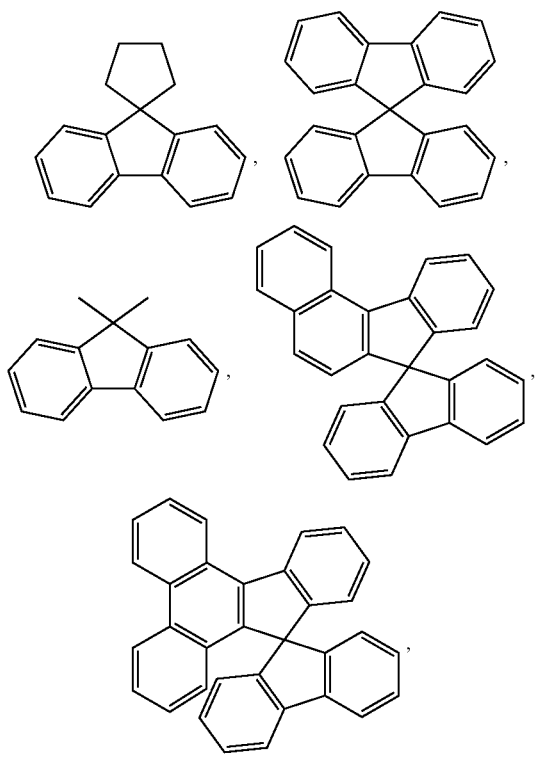

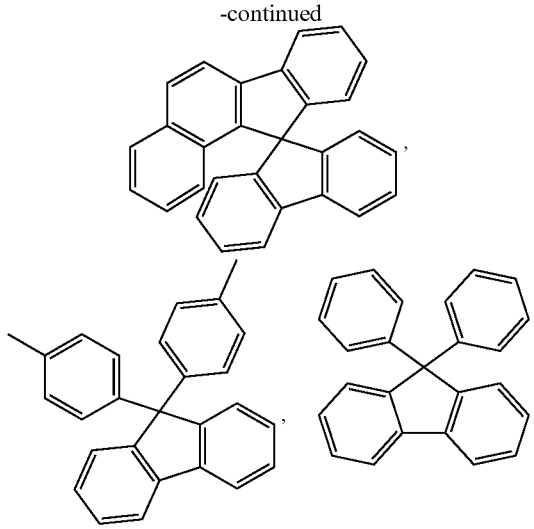

and the like may be included. However, the structure is not limited thereto.

In the present specification, the heterocyclic group is a heterocyclic group including one or more of N, O, S, Si and Se as a heteroatom, and although not particularly limited thereto, the number of carbon atoms is preferably from 2 to 60. Examples of the heterocyclic group may include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenoxazinyl group, a phenothiazinyl group, a dibenzofuranyl group and the like, but are not limited thereto.

In the present specification, the descriptions on the heterocyclic group provided above may be used on the heteroaryl group except that the heteroaryl group is an aromatic group.

In the present specification, the descriptions on the aryl group provided above may be used on the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, the descriptions on the alkyl group provided above may be used on the alkyl group in the alkylthioxy group, the alkylsulfoxy group, the aralkyl group, the aralkylamine group, the alkylaryl group and the alkylamine group.

In the present specification, the descriptions on the heteroaryl group provided above may be used on the heteroayl group in the heteroaryl group, the heteroarylamine group and the arylheteroarylamine group.

In the present specification, the descriptions on the alkenyl group provided above may be used on the alkenyl group in the aralkenyl group.

In the present specification, the descriptions on the aryl group provided above may be used on the arylene group except that the arylene group is divalent.

In the present specification, the descriptions on the heteroaryl group provided above may be used on the heteroarylene group except that the heteroarylene group is divalent.

In the present specification, bonding to an adjacent group to form a ring means bonding to an adjacent group to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

In the present specification, the aliphatic hydrocarbon ring means a ring that is not aromatic and formed only with carbon and hydrogen atoms.

In the present specification, examples of the aromatic hydrocarbon ring may include benzene, naphthalene, anthracene and the like, but are not limited thereto.

In the present specification, the aliphatic heteroring means an aliphatic ring including one or more of heteroatoms.

In the present specification, the aromatic heteroring means an aromatic ring including one or more of heteroatoms.

In the present specification, the aliphatic hydrocarbon ring, the aromatic hydrocarbon ring, the aliphatic heteroring and the aromatic heteroring may be monocyclic or multicyclic.

According to one embodiment of the present specification, Chemical Formula 1 may be represented by one of the following Chemical Formulae 2 to 5.

[Chemical Formula 2]

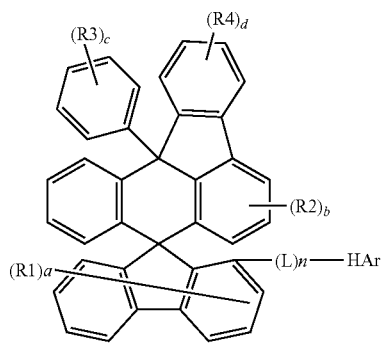

[Chemical Formula 3]

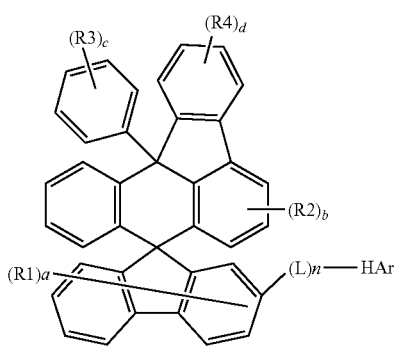

[Chemical Formula 4]

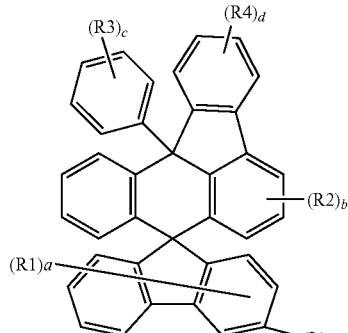

[Chemical Formula 5]

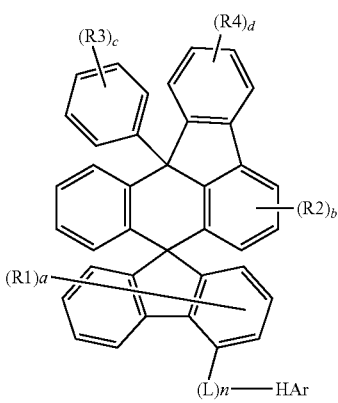

In Chemical Formulae 2 to 5, definitions of substituents are the same as in Chemical Formula 1.

According to one embodiment of the present application, in Chemical Formulae 1 to 5, HAr is a substituted or unsubstituted pyridyl group; a substituted or unsubstituted pyrimidyl group; a substituted or unsubstituted triazinyl group; a substituted or unsubstituted furan group; a substituted or unsubstituted thiophene group; a substituted or unsubstituted oxadiazole group; a substituted or unsubstituted thiadiazole group; a substituted or unsubstituted phenanthroline group; a substituted or unsubstituted quinolinyl group; a substituted or unsubstituted isoquinolinyl group; a substituted or unsubstituted quinazoline group; a substituted or unsubstituted benzoxazole group; a substituted or unsubstituted benzothiazole group; a substituted or unsubstituted benzimidazole group; a substituted or unsubstituted phenoxazine group; a substituted or unsubstituted phenothiazine group; a substituted or unsubstituted dibenzofuran group; a substituted or unsubstituted dibenzothiophene group; a substituted or unsubstituted carbazole group; or a substituted or unsubstituted diarylphosphine oxide group.

According to one embodiment of the present application, in Chemical Formulae 1 to 5, HAr may be unsubstituted or substituted with a substituted or unsubstituted aryl group; a substituted or unsubstituted heterocyclic group; a substituted or unsubstituted arylamine group; a substituted or unsubstituted heteroarylamine group; or a substituted or unsubstituted arylheteroarylamine group.

According to one embodiment of the present application, in Chemical Formulae 1 to 5, HAr may be unsubstituted or substituted with a substituted or unsubstituted aryl group or a substituted or unsubstituted heterocyclic group.

According to one embodiment of the present application, in Chemical Formulae 1 to 5, HAr may be unsubstituted or substituted with a substituted or unsubstituted aryl group.

According to one embodiment of the present application, in Chemical Formulae 1 to 5, HAr may be unsubstituted or substituted with an aryl group.

According to one embodiment of the present application, in Chemical Formulae 1 to 5, HAr may be unsubstituted or substituted with a phenyl group or a biphenylyl group.

According to one embodiment of the present application, in Chemical Formulae 1 to 5, -(L)n-HAr may be represented by the following structural formulae.

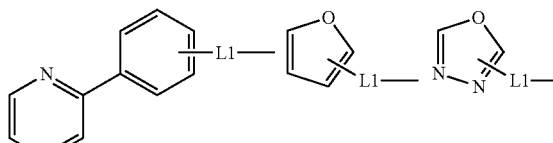
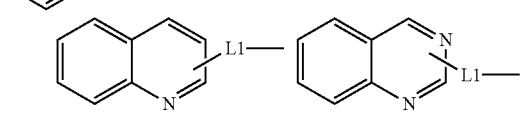
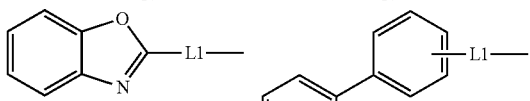
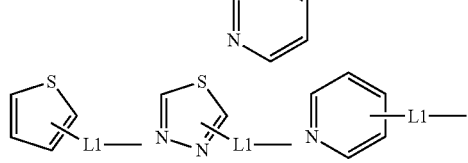
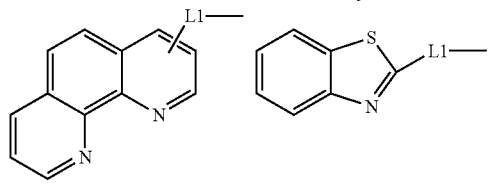
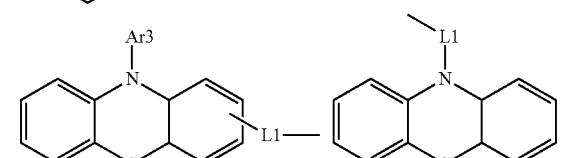
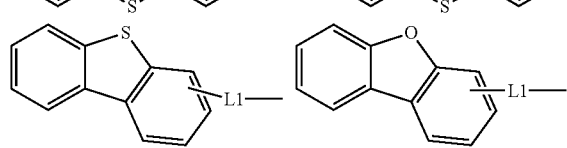
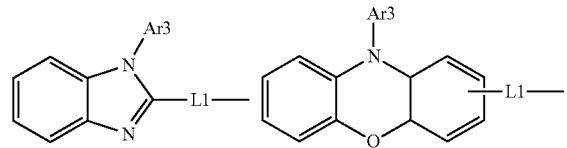
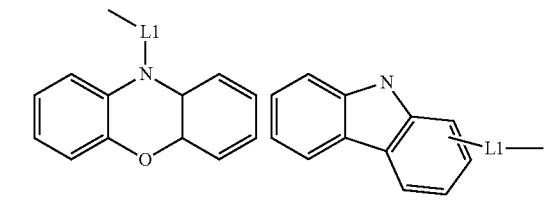

-continued

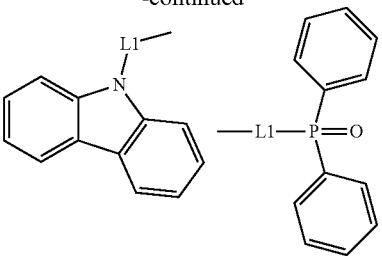
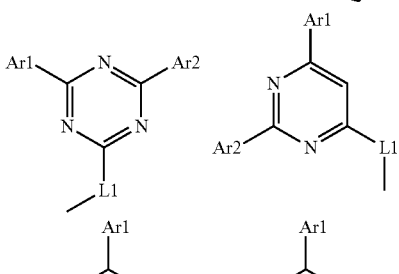
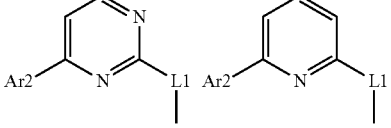
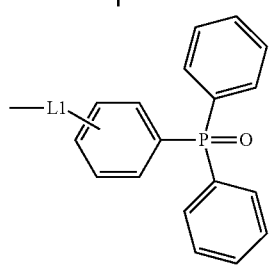

In the structural formulae,

Ar1 to Ar3 are the same as or different from each other, and each independently a substituted or unsubstituted aryl group; a substituted or unsubstituted heterocyclic group; a substituted or unsubstituted arylamine group; a substituted or unsubstituted heteroarylamine group; or a substituted or unsubstituted arylheteroarylamine group, L1 is a direct bond; a substituted or unsubstituted arylene group; or a substituted or unsubstituted heteroarylene group, and the structural formulae may be unsubstituted or substituted with one or more substituents selected from the group consisting of deuterium; a halogen group; a nitrile group; a nitro group; a hydroxyl group; a carbonyl group; an ester group; an imide group; a substituted or unsubstituted amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment, the structural formulae illustrated as -(L)n-HAr may be unsubstituted or substituted with a substituted or unsubstituted aryl group; a substituted or unsubstituted heterocyclic group; a substituted or unsubstituted arylamine group; a substituted or unsubstituted heteroarylamine group; or a substituted or unsubstituted arylheteroarylamine group.

According to one embodiment of the present disclosure, L and L1 are the same as or different from each other, and each independently a direct bond; or a substituted or unsubstituted monocyclic to pentacyclic arylene group.

According to one embodiment of the present disclosure, L and L1 are the same as or different from each other, and each independently a direct bond; or a substituted or unsubstituted monocyclic to tetracyclic arylene group.

According to one embodiment of the present disclosure, L and L1 are the same as or different from each other, and each independently a direct bond; or an arylene group.

According to one embodiment of the present disclosure, L and L1 are the same as or different from each other, and each independently a direct bond; a substituted or unsubstituted phenylene group; a substituted or unsubstituted divalent biphenyl group; a substituted or unsubstituted divalent terphenyl group; a substituted or unsubstituted divalent quaterphenyl group; a substituted or unsubstituted divalent naphthyl group; a substituted or unsubstituted divalent anthracenyl group; a substituted or unsubstituted divalent fluorenyl group; a substituted or unsubstituted divalent phenanthryl group; a substituted or unsubstituted divalent pyrenyl group; or a substituted or unsubstituted divalent chrysenyl group.

According to one embodiment of the present disclosure, L and L1 are the same as or different from each other, and each independently a direct bond; a phenylene group; a divalent biphenyl group; a divalent terphenyl group; a divalent quaterphenyl group; a divalent naphthyl group; a divalent anthracenyl group; a divalent fluorenyl group; a divalent phenanthryl group; a divalent pyrenyl group; or a divalent chrysenyl group.

According to one embodiment of the present disclosure, L and L1 are the same as or different from each other, and each independently a substituted or unsubstituted heteroarylene group.

According to one embodiment of the present disclosure, L and L1 are the same as or different from each other, and each independently a substituted or unsubstituted heteroarylene group including O, N or S.

According to one embodiment of the present disclosure, L and L1 are the same as or different from each other, and each independently a heteroarylene group including O, N or S.

According to one embodiment of the present disclosure, L and L1 are the same as or different from each other, and each independently a direct bond or any one selected from among the following structural formulae.

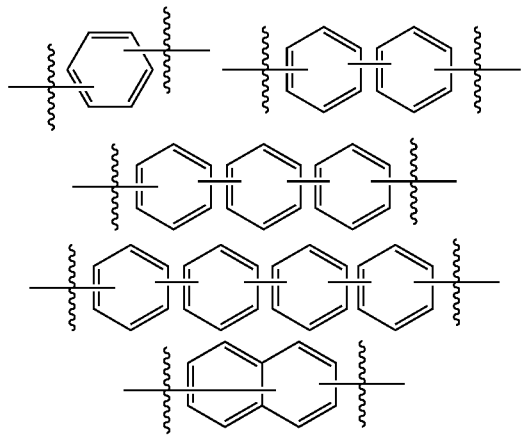

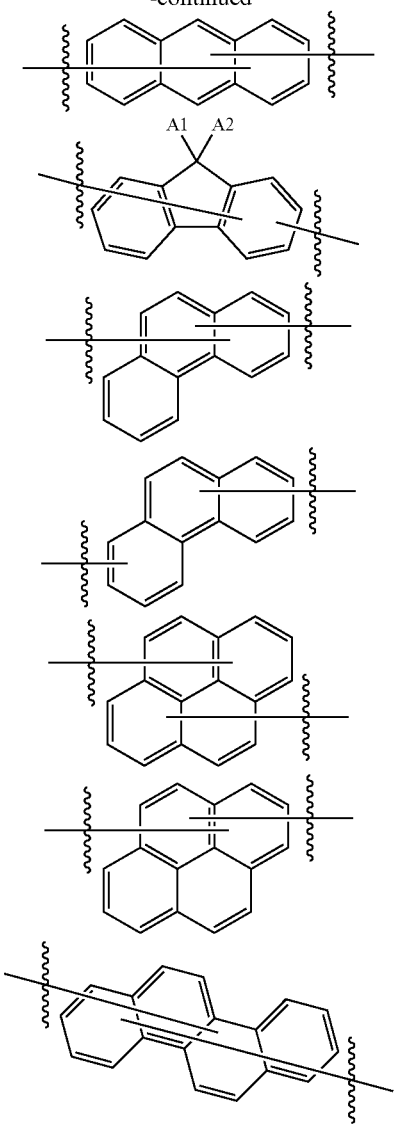

In the structural formulae,

A1 and A2 are the same as or different from each other, and each independently hydrogen; a substituted or unsubstituted alkyl group; a substituted or unsubstituted aryl group; or a substituted or unsubstituted heterocyclic group, or may bond to each other to form a substituted or unsubstituted ring, and the structures may be unsubstituted or substituted with one or more substituents selected from the group consisting of deuterium; a halogen group; a nitrile group; a nitro group; a hydroxyl group; a carbonyl group; an ester group; an imide group; a substituted or unsubstituted amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

According to one embodiment of the present disclosure, L and L1 are the same as or different from each other, and each independently a direct bond or any one selected from among the following structural formulae.

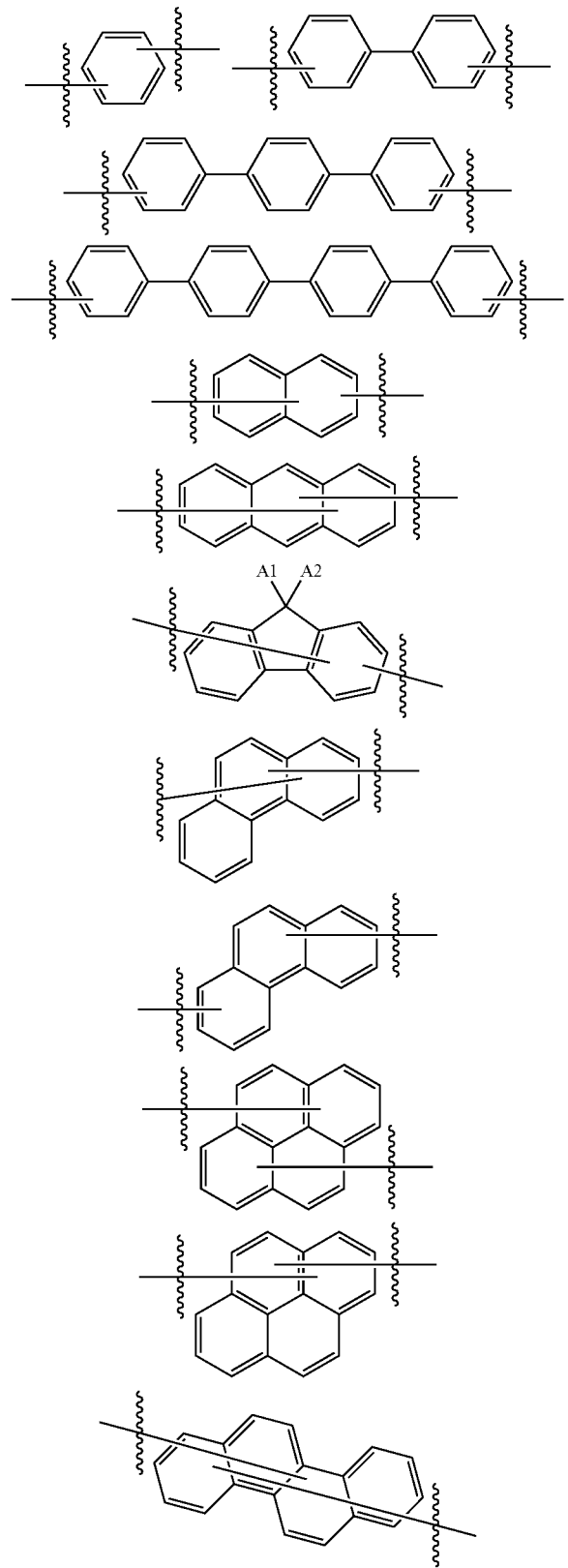

In the structural formulae,

A1 and A2 are the same as or different from each other, and each independently hydrogen; a substituted or unsubstituted alkyl group; a substituted or unsubstituted aryl group; or a substituted or unsubstituted heterocyclic group, or may bond to each other to form a substituted or unsubstituted ring, and the structures may be unsubstituted or substituted with one or more substituents selected from the group consisting of deuterium; a halogen group; a nitrile group; a nitro group; a hydroxyl group; a carbonyl group; an ester group; an imide group; a substituted or unsubstituted amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

According to one embodiment of the present disclosure, L and L1 are the same as or different from each other, and each independently a direct bond; or any one selected from among the following structural formulae.

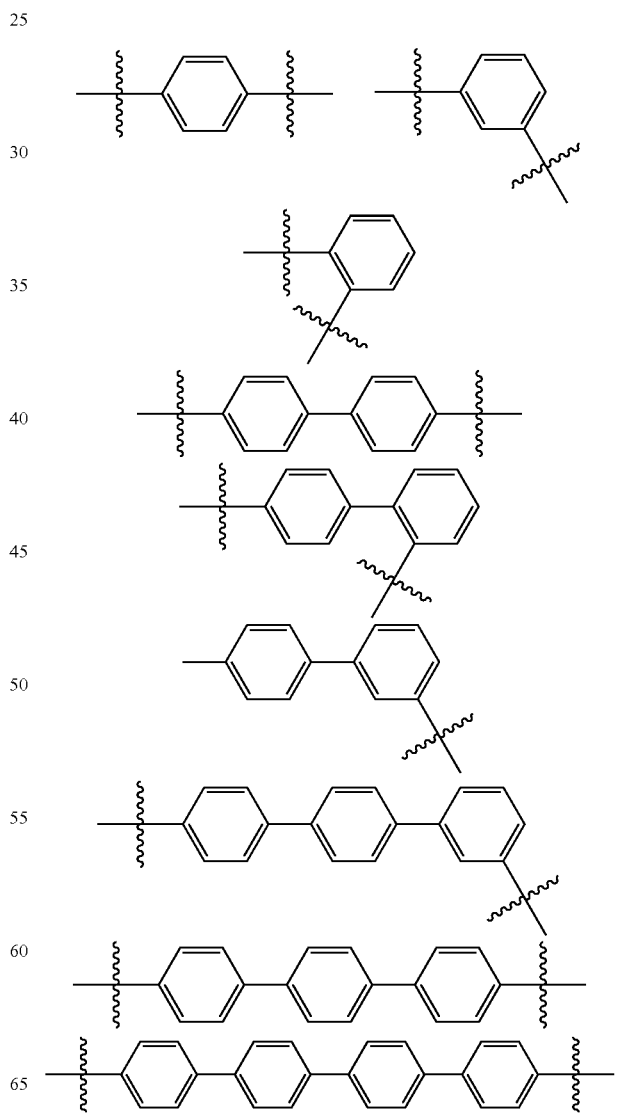

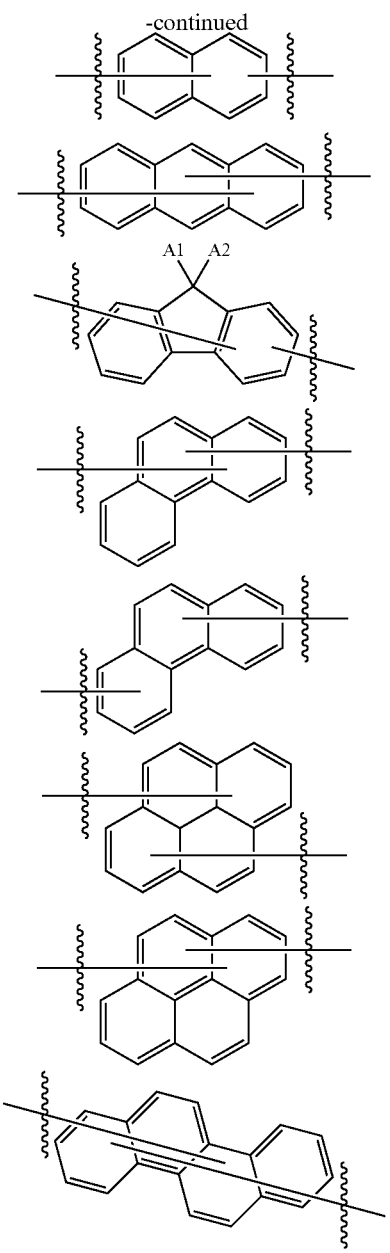

In the structural formulae,

A1 and A2 are the same as or different from each other, and each independently hydrogen; a substituted or unsubstituted alkyl group; a substituted or unsubstituted aryl group; or a substituted or unsubstituted heterocyclic group, or may bond to each other to form a substituted or unsubstituted ring, and the structures may be unsubstituted or substituted with one or more substituents selected from the group consisting of deuterium; a halogen group; a nitrile group; a nitro group; a hydroxyl group; a carbonyl group; an ester group; an imide group; a substituted or unsubstituted amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

According to one embodiment of the present disclosure, L and L1 are the same as or different from each other, and each independently a direct bond; a phenylene group; a biphenylylene group; or a fluorenylene group.

According to one embodiment of the present disclosure, L and L1 are the same as or different from each other, and each independently a direct bond; or a phenylene group.

According to one embodiment of the present disclosure, in the structural formulae described above, Ar1 to Ar3 are the same as or different from each other, and each independently a substituted or unsubstituted aryl group; or a substituted or unsubstituted heterocyclic group.

According to one embodiment of the present disclosure, in the structural formulae described above, Ar1 to Ar3 are the same as or different from each other, and each independently a substituted or unsubstituted aryl group.

According to one embodiment of the present disclosure, in the structural formulae described above, Ar1 to Ar3 are the same as or different from each other, and each independently a phenyl group; a biphenylyl group; or a naphthyl group.

According to one embodiment of the present disclosure, the compound of Chemical Formula 1 may be any one selected from among the following compounds.

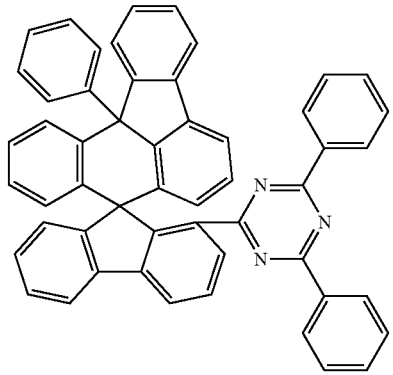

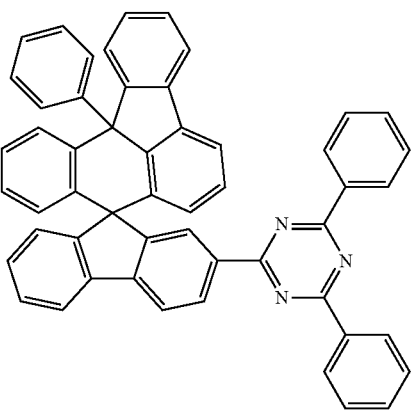

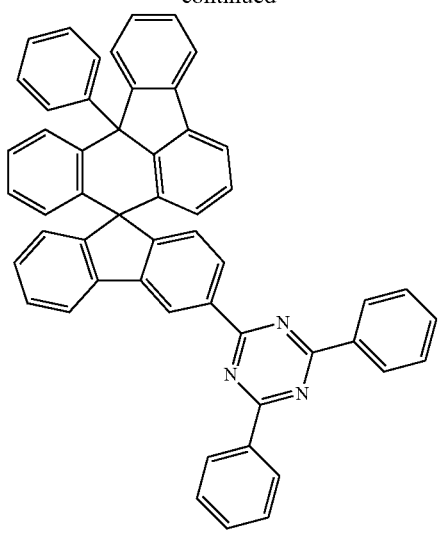
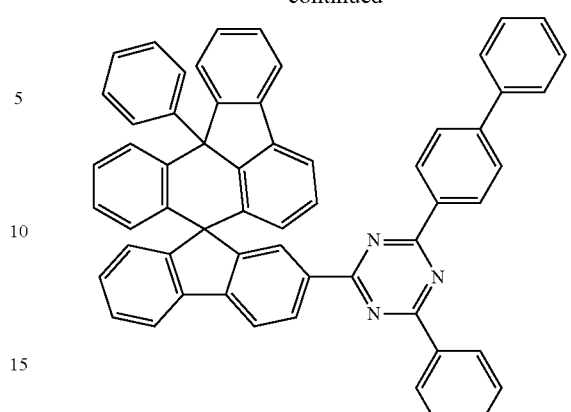
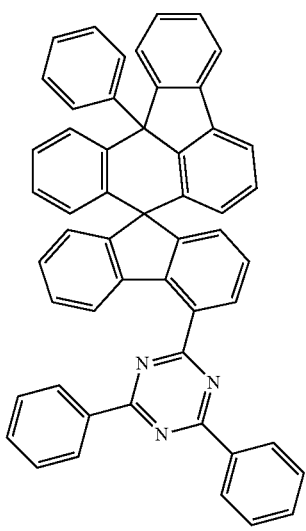
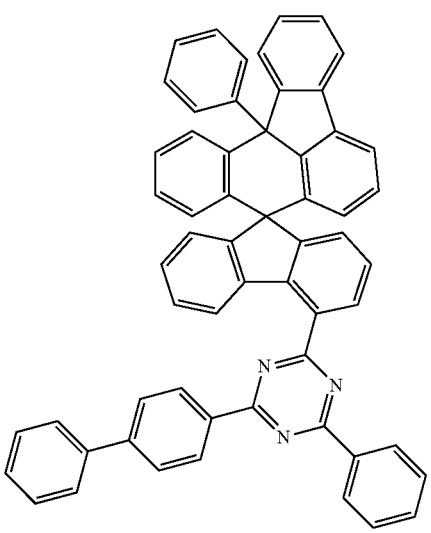
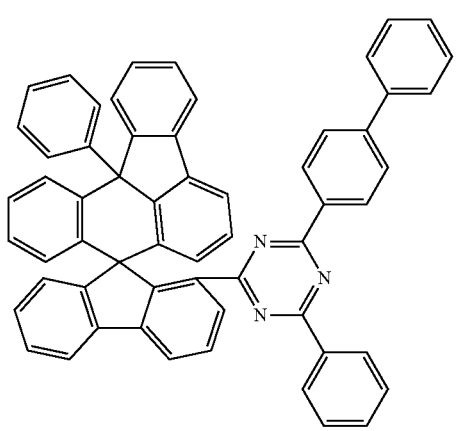

-continued
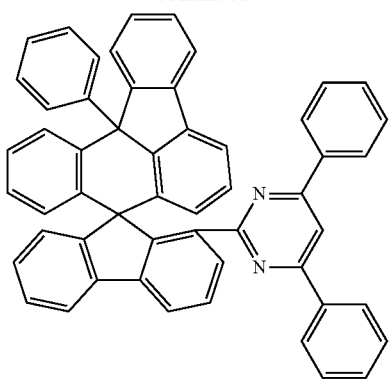
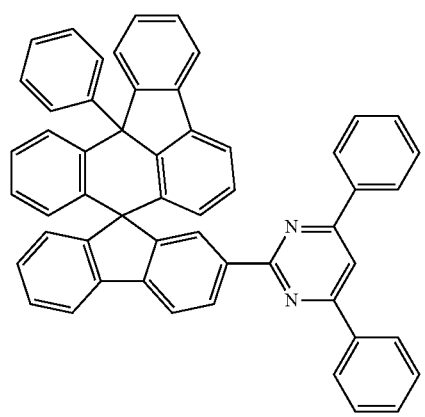
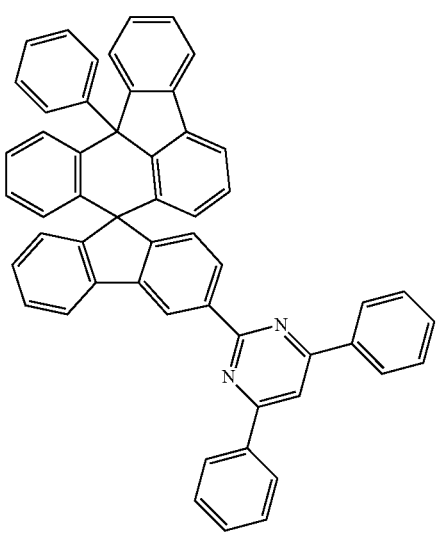
-continued
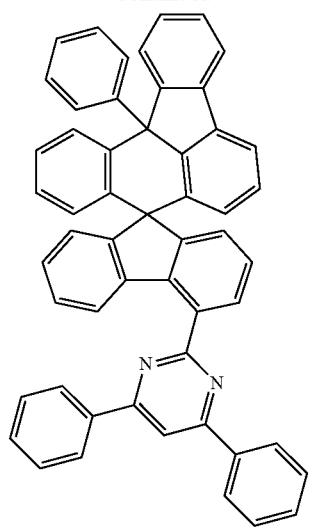
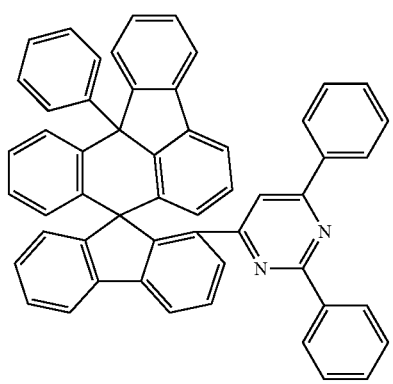
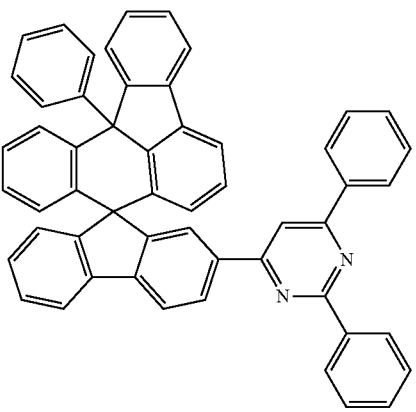

-continued
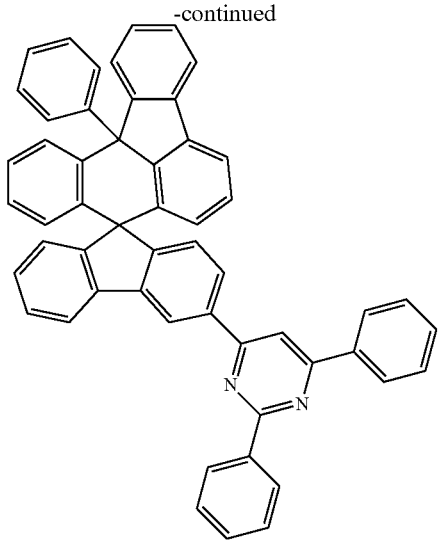
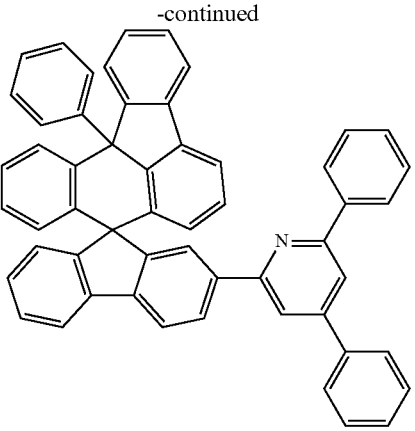
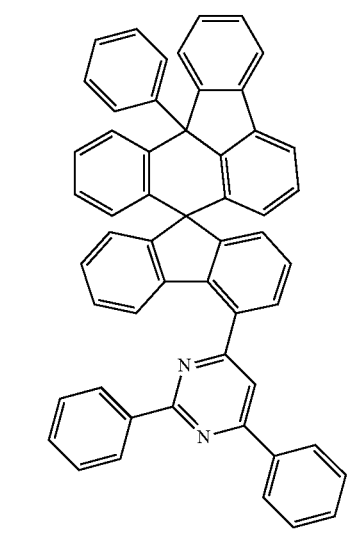
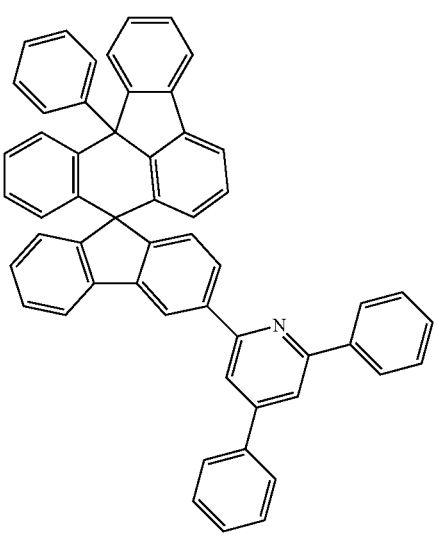
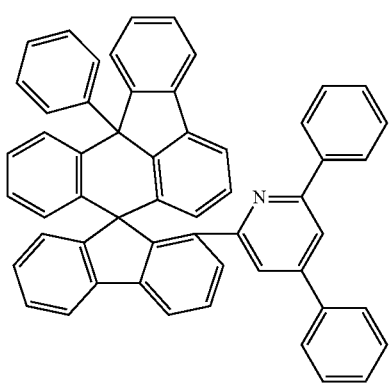
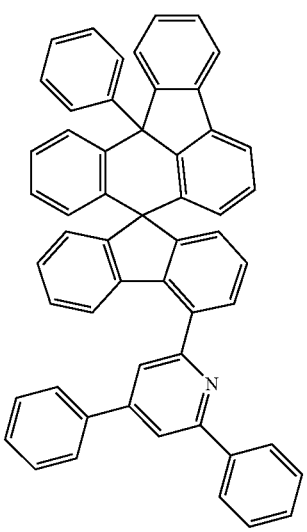

25
-continued
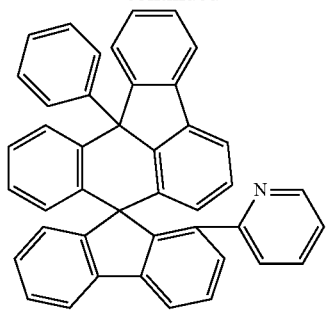
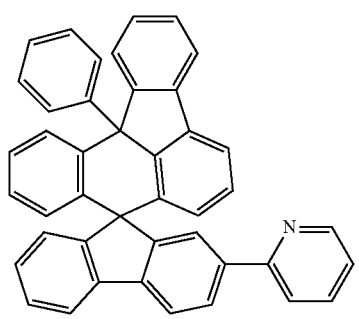
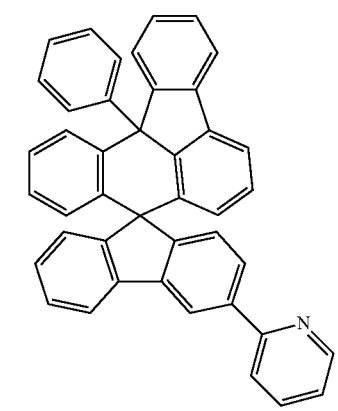
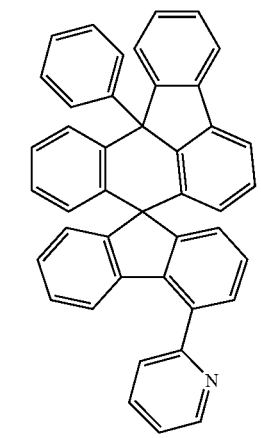
26
-continued
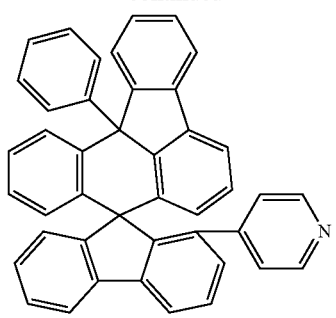
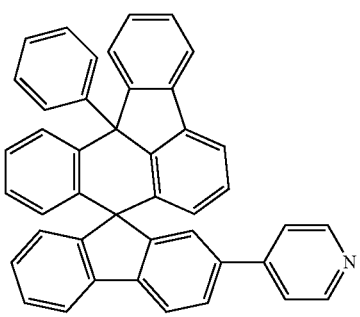
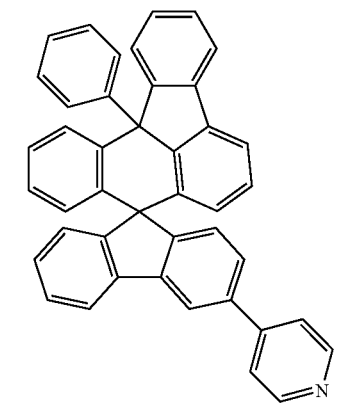
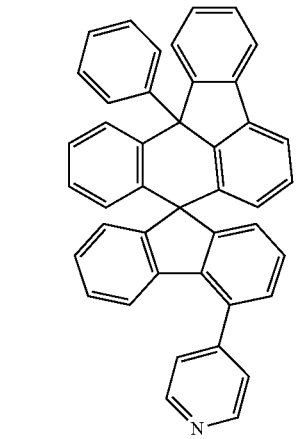

-continued
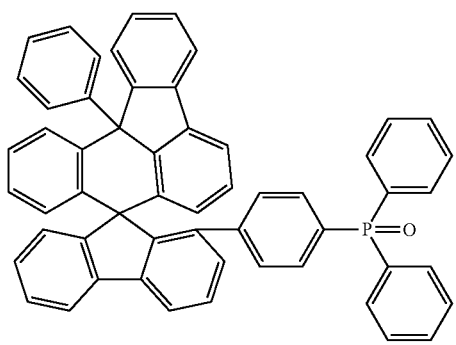
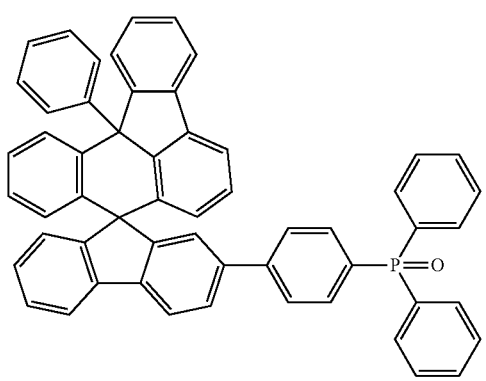
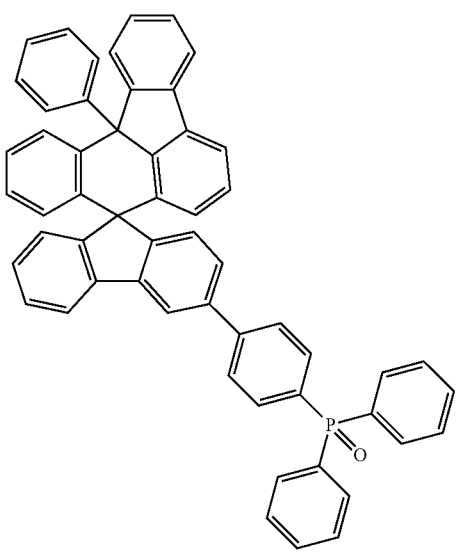
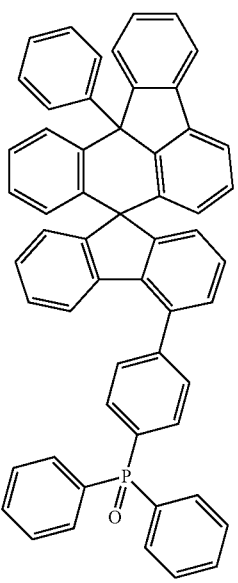
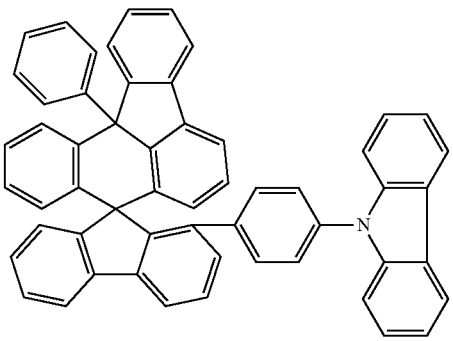

-continued
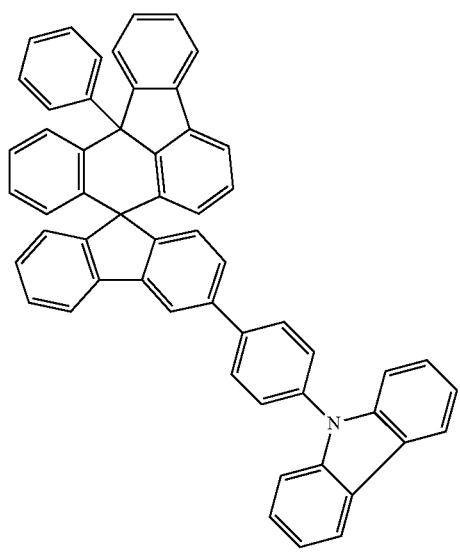
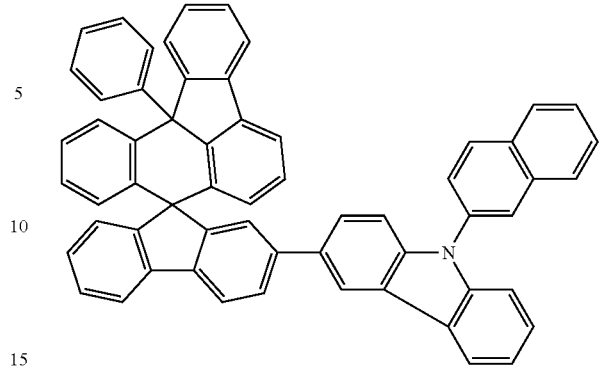
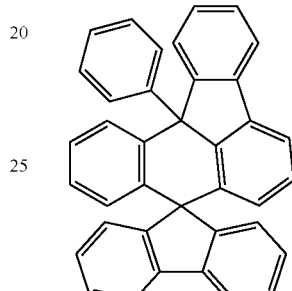
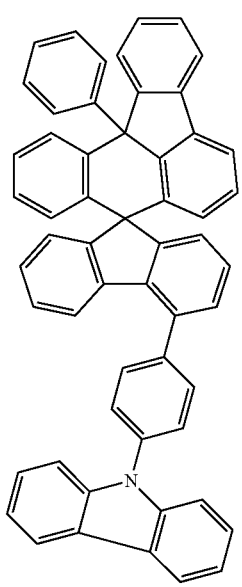
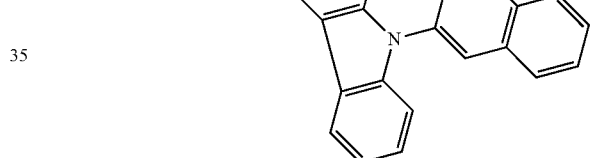
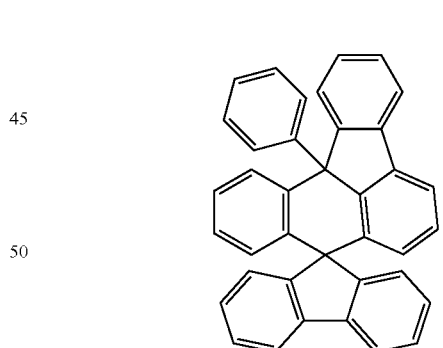
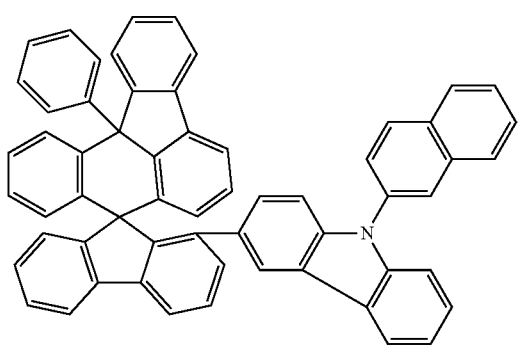
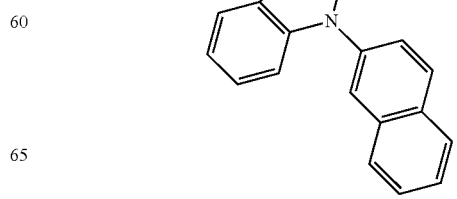

31
-continued
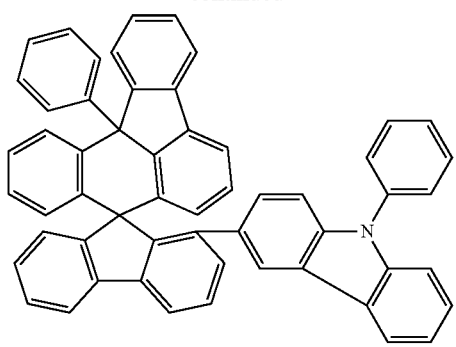
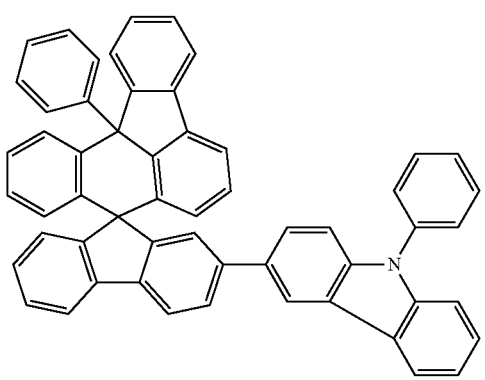
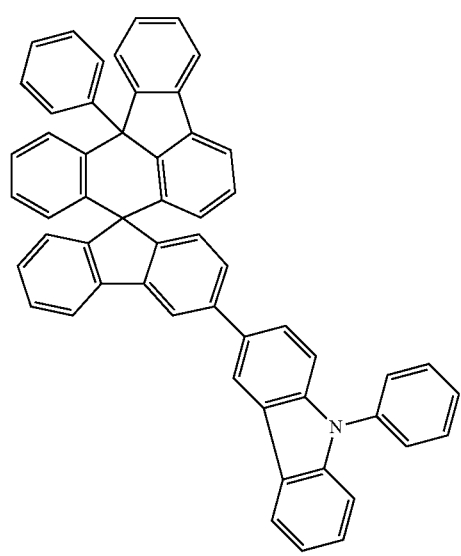
32
-continued
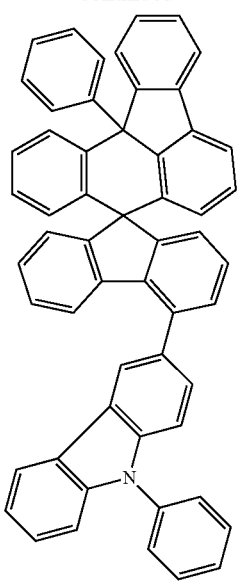
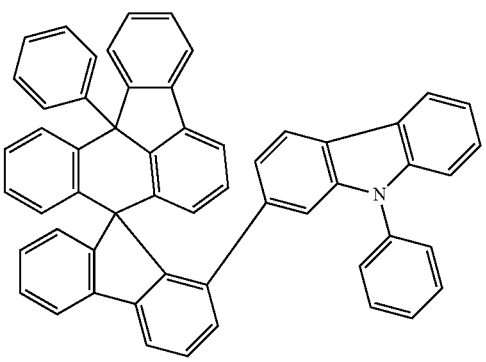
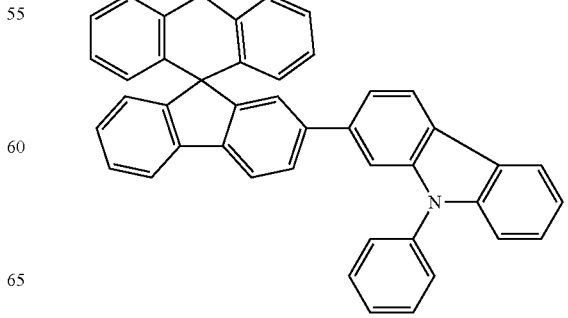

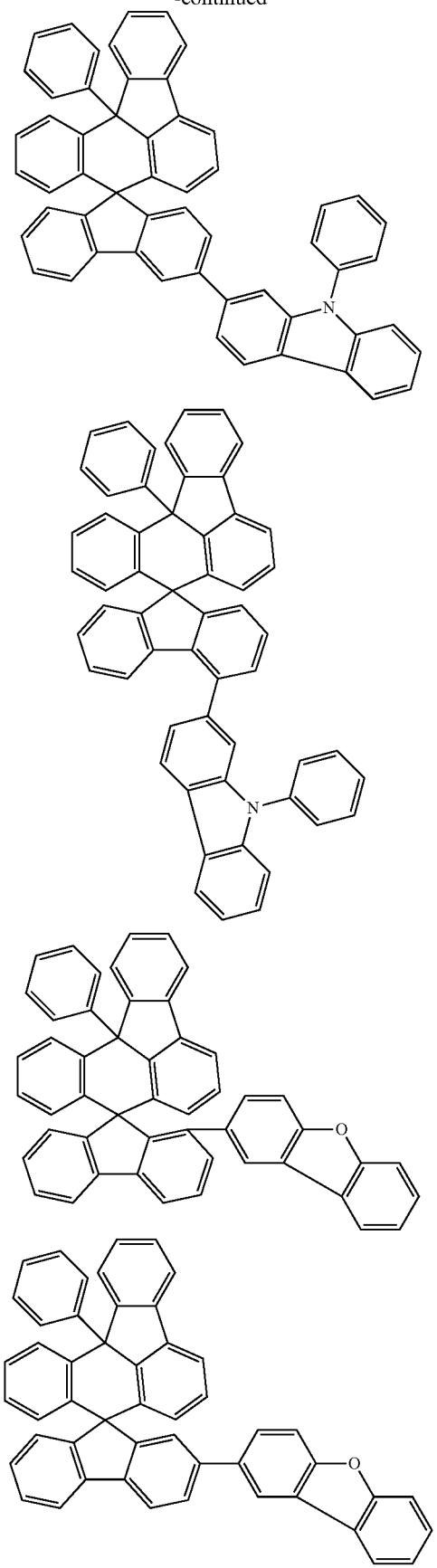
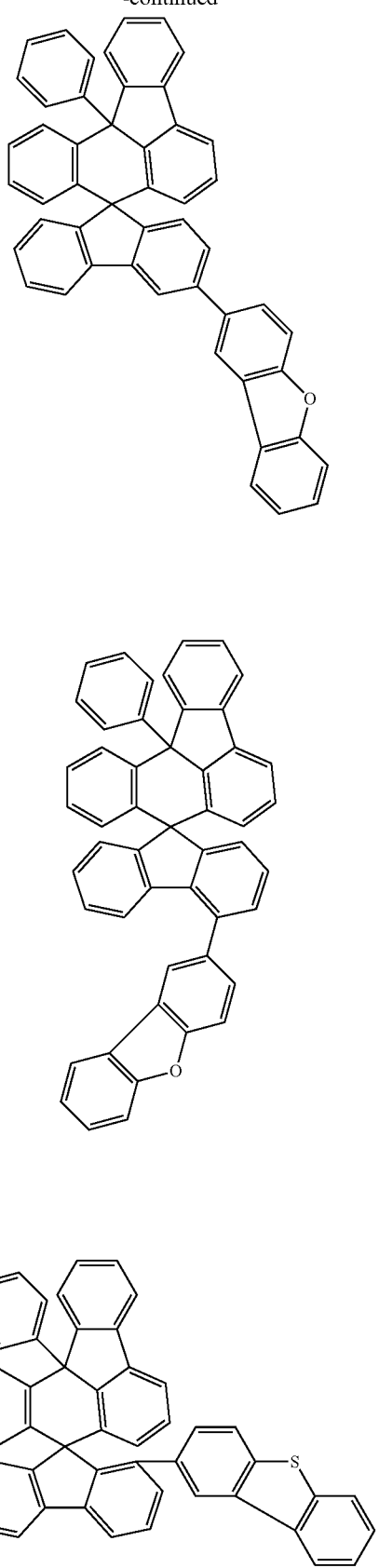

35
-continued
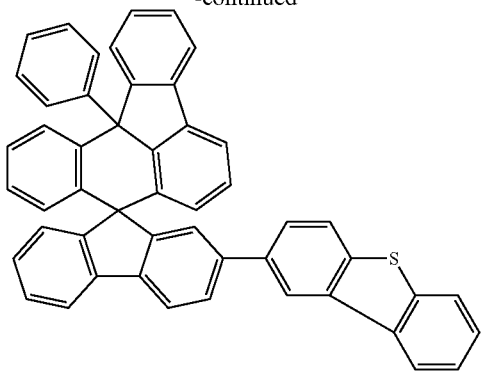
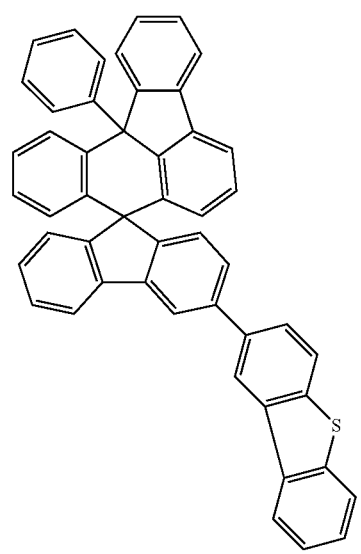
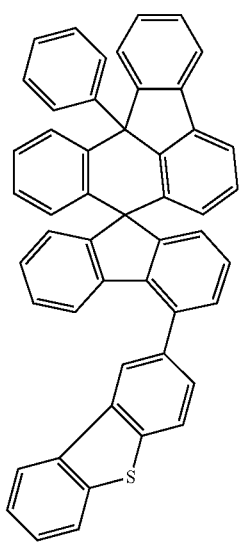
36
-continued
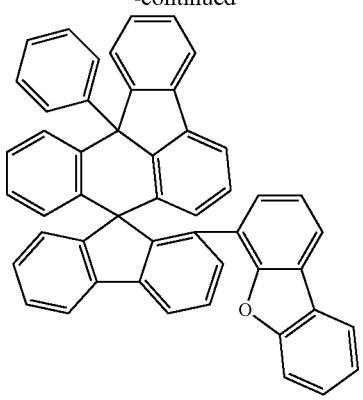
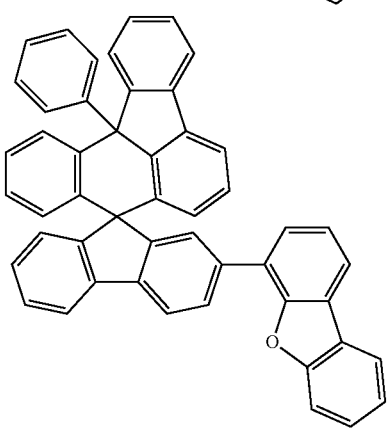
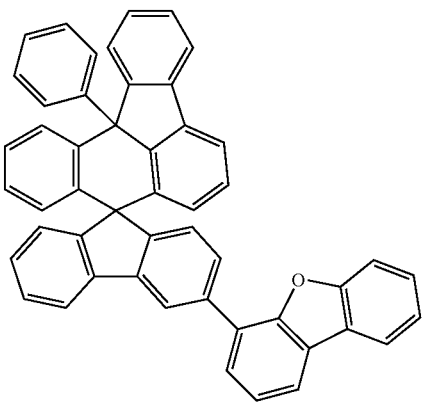
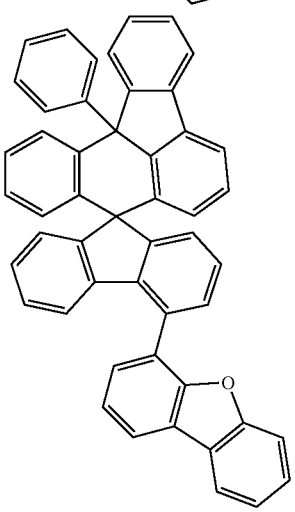

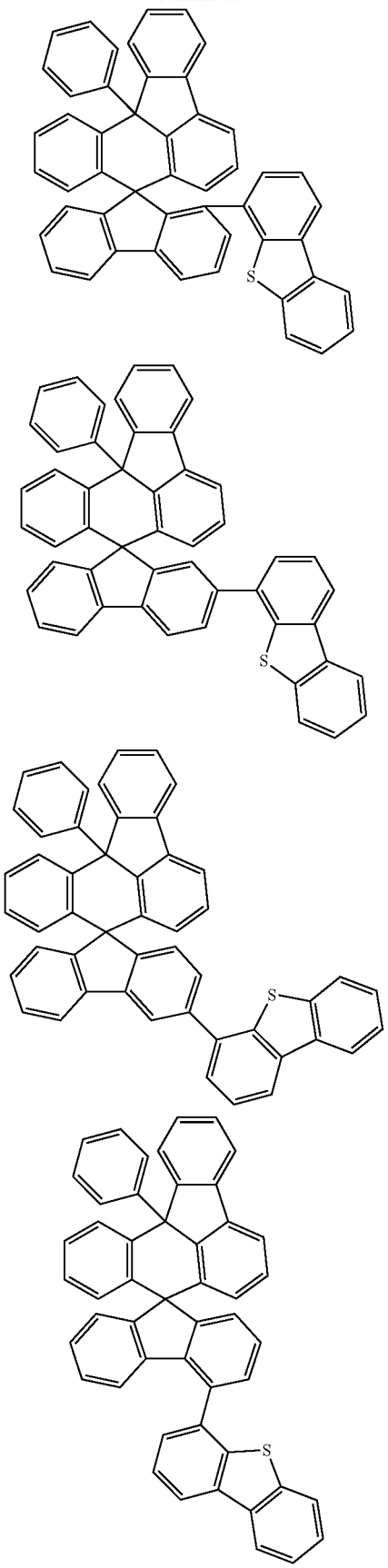

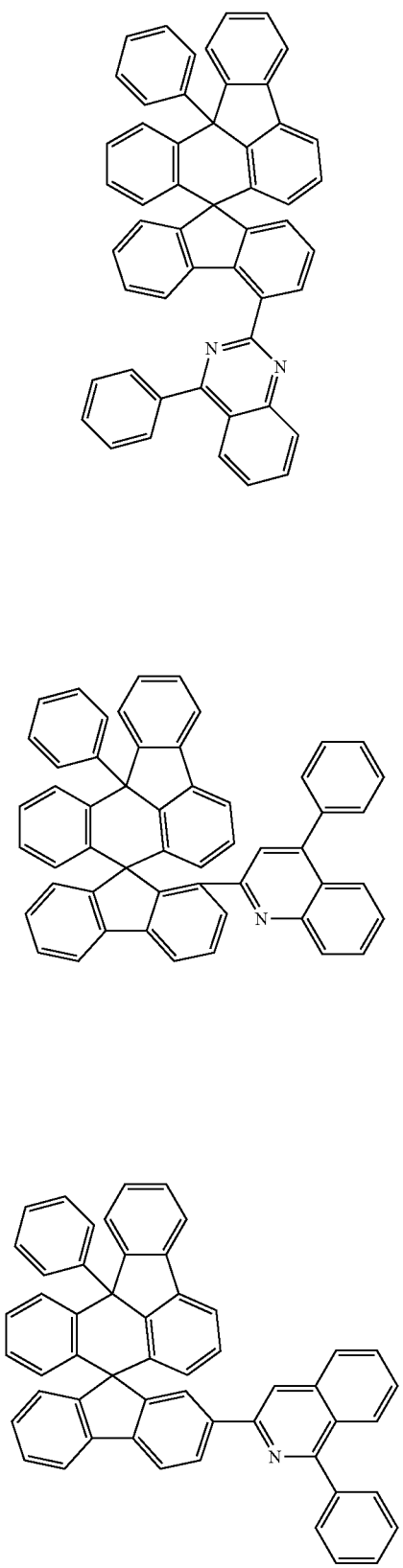
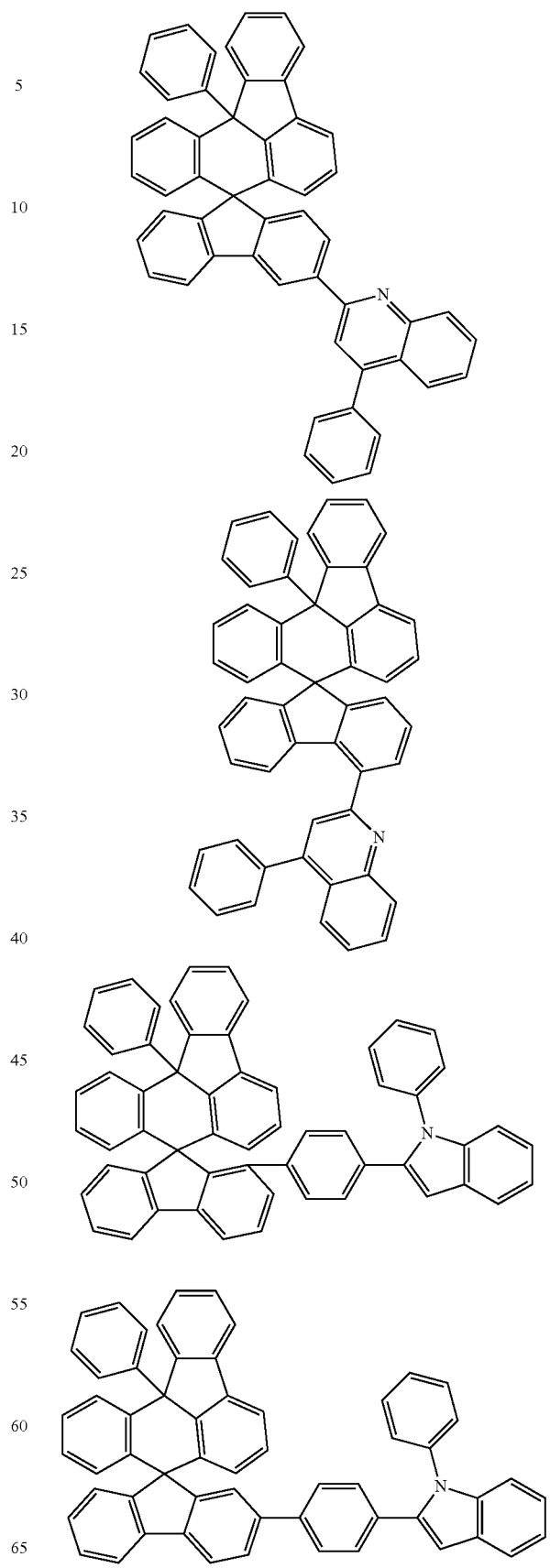

41
-continued
42
-continued
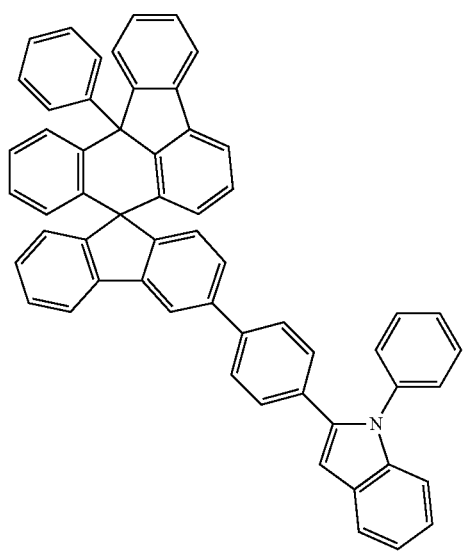
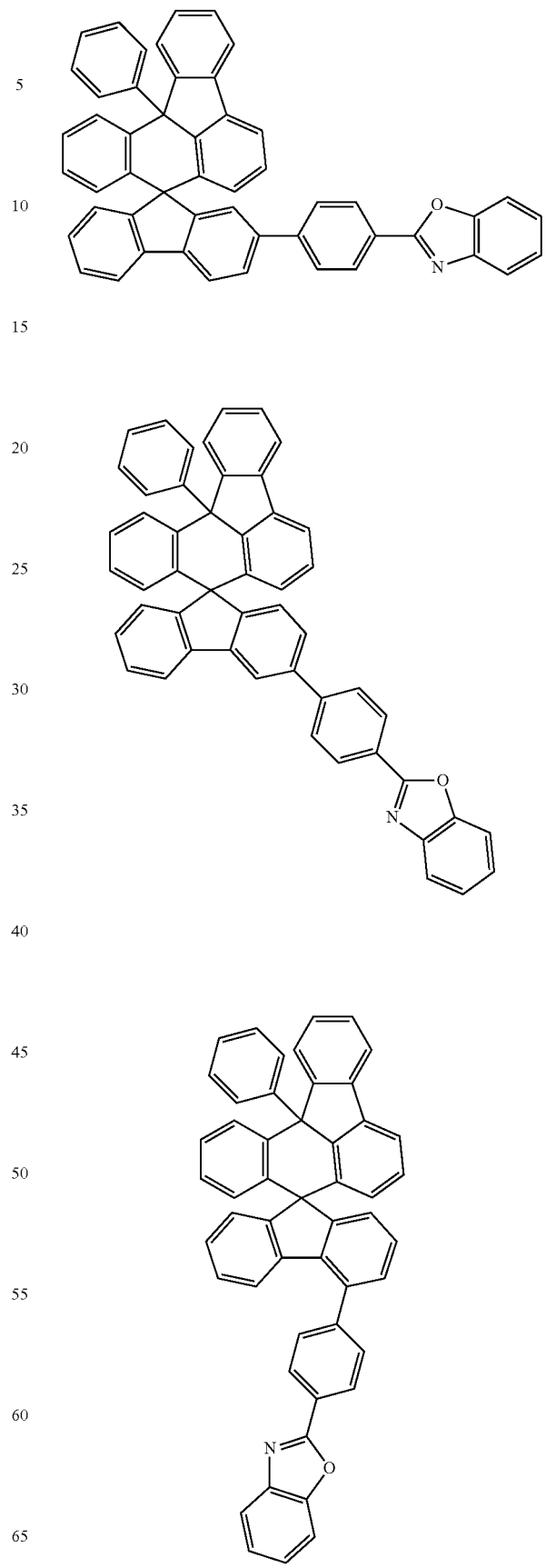

-continued
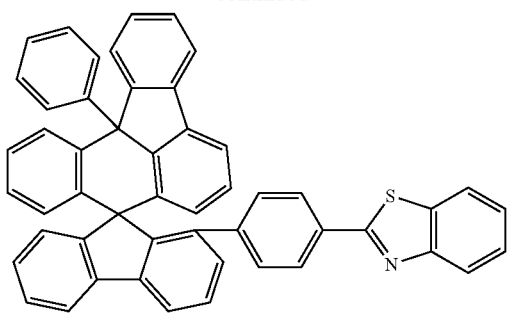
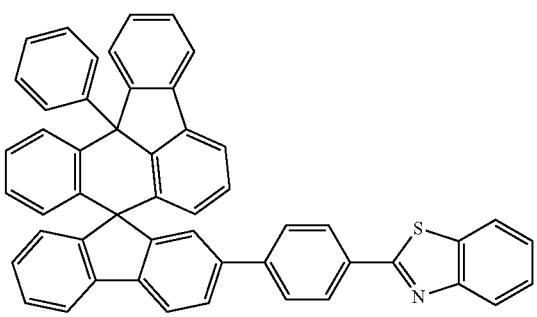
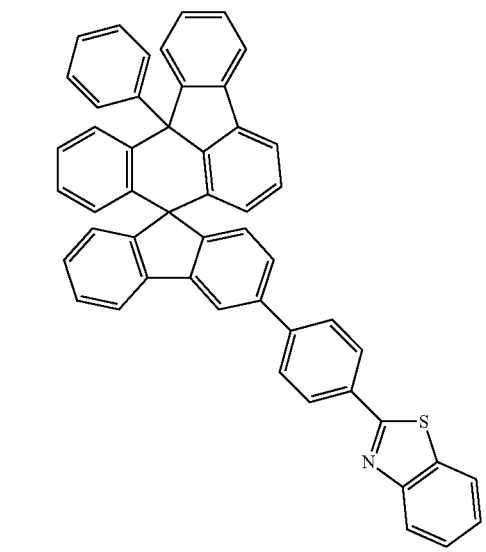
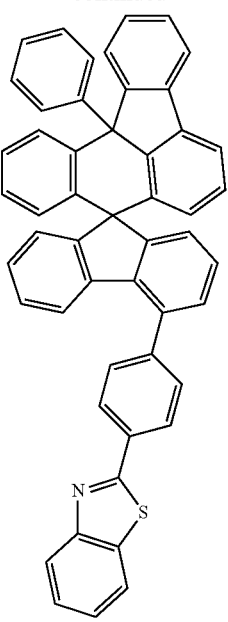
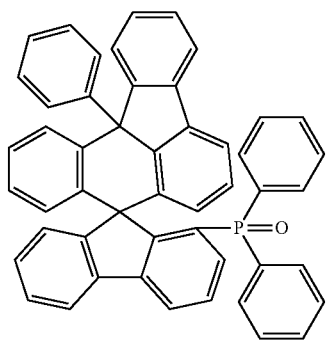
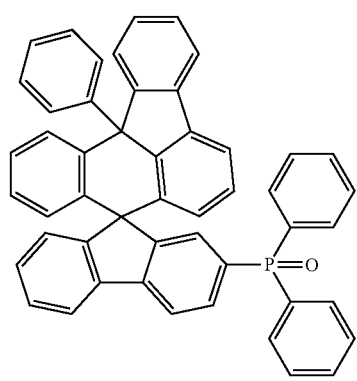

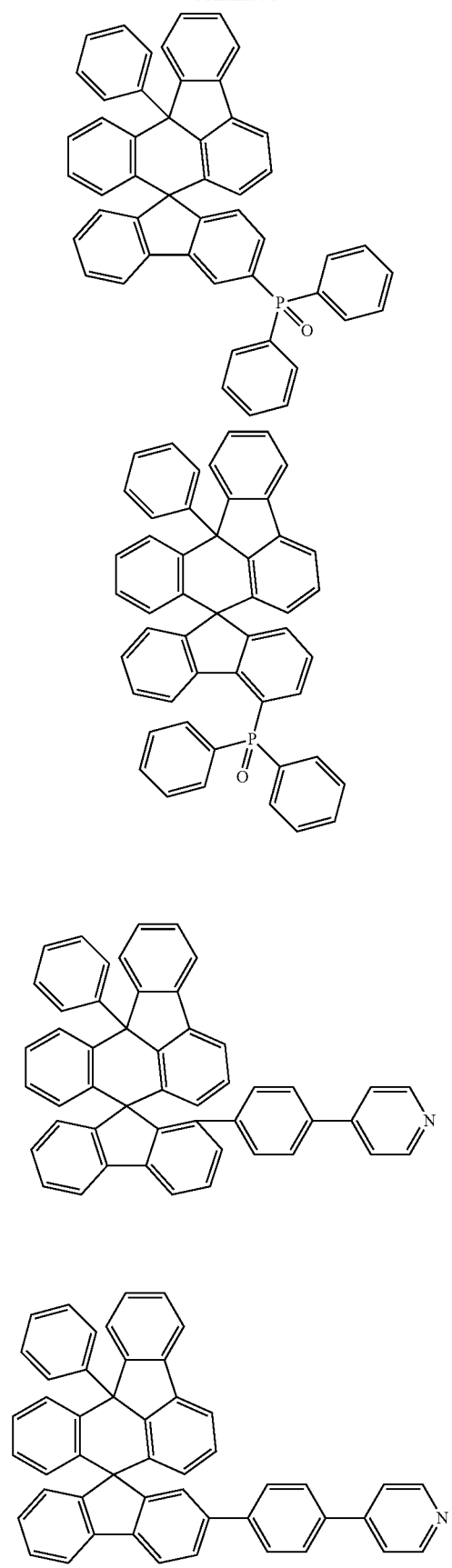

47
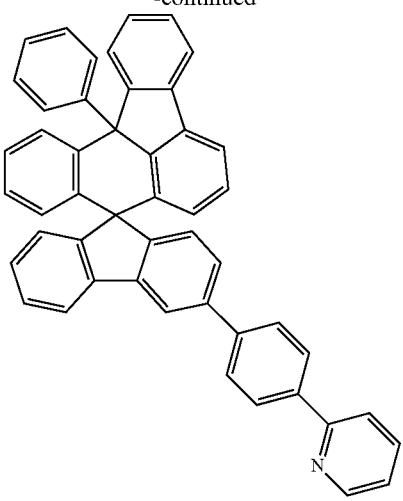
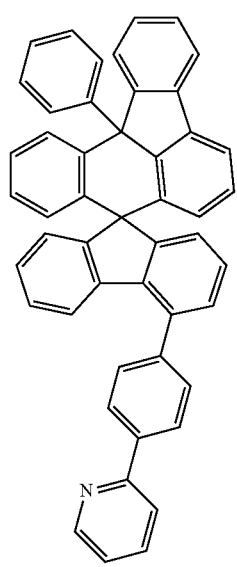
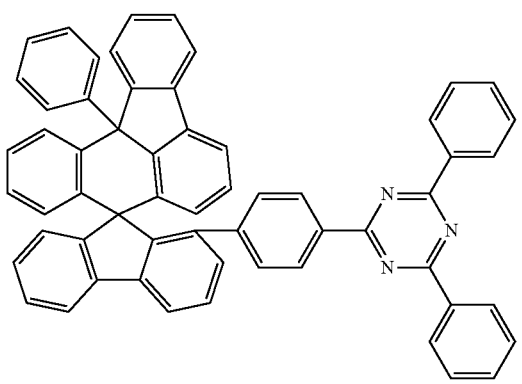
48
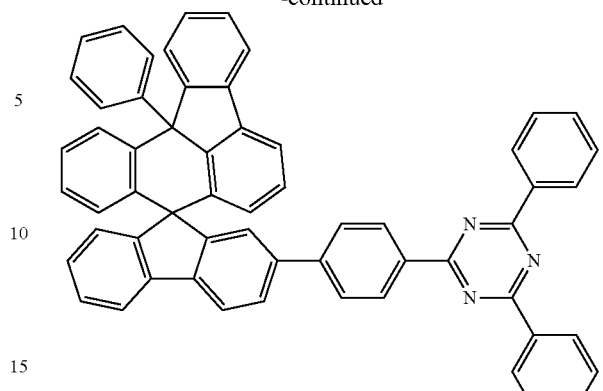
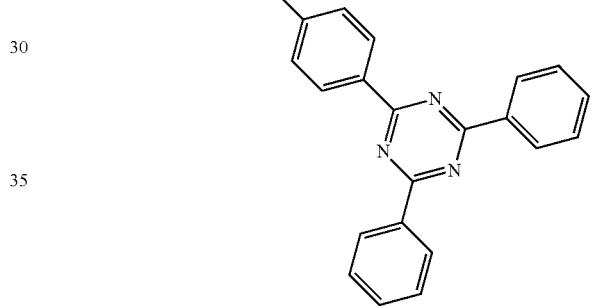
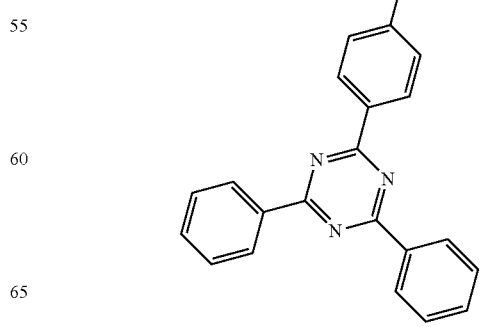

49
-continued
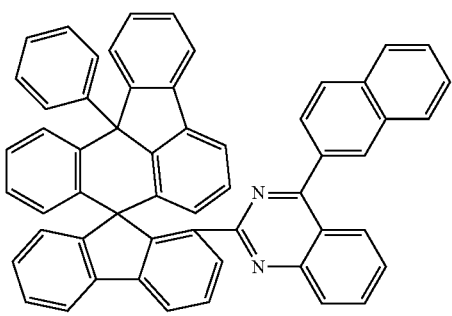
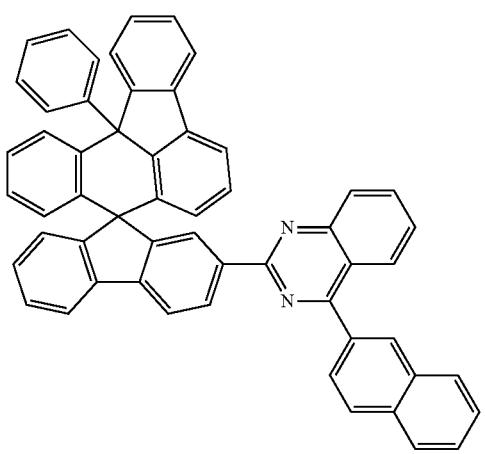
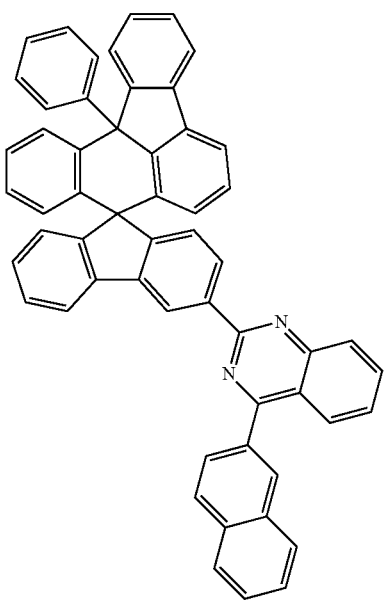
50
-continued
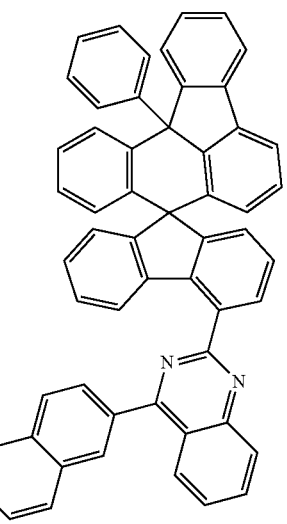
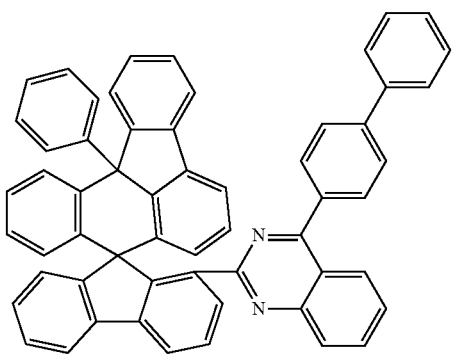
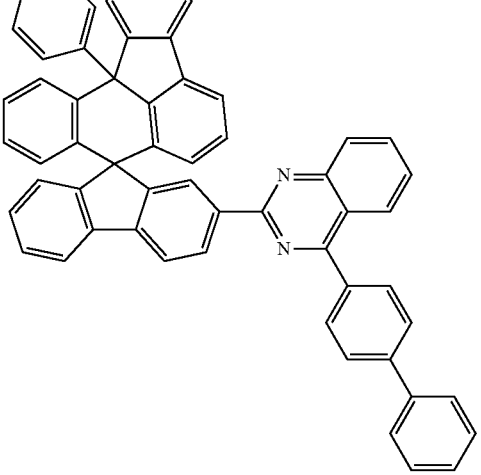

51
-continued
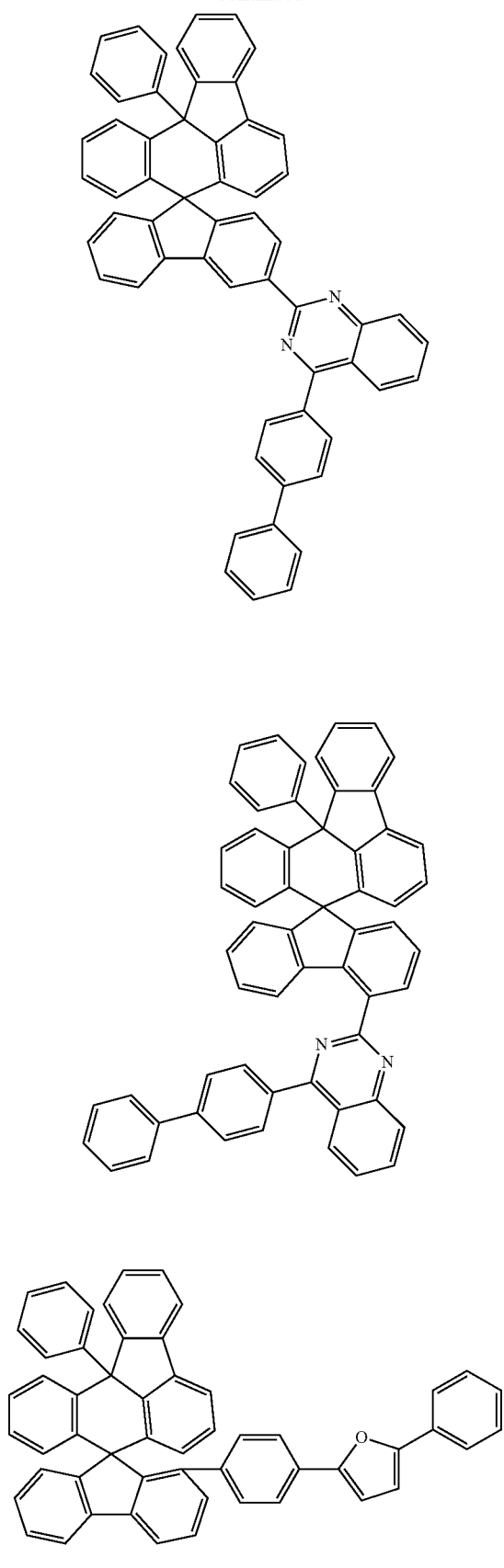
52
-continued
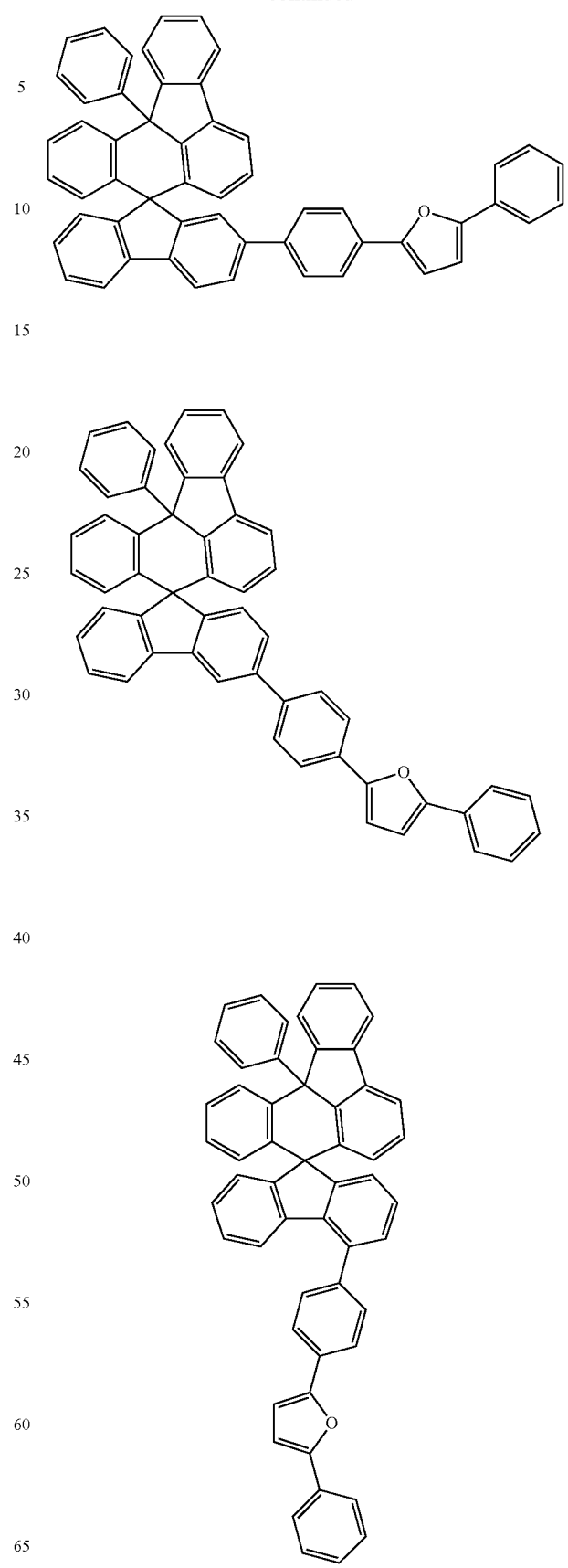

53
-continued
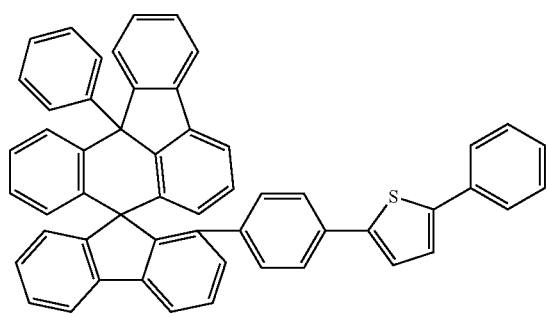
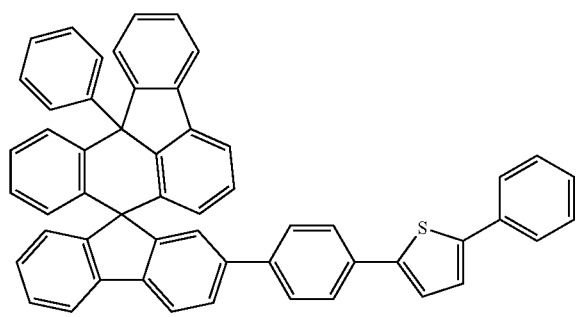
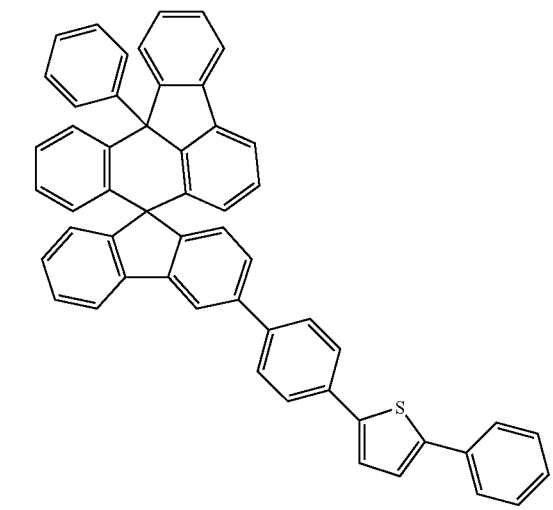
54
-continued
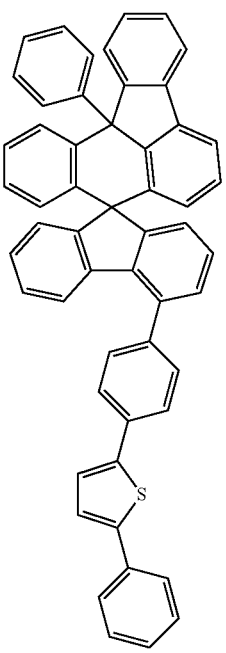
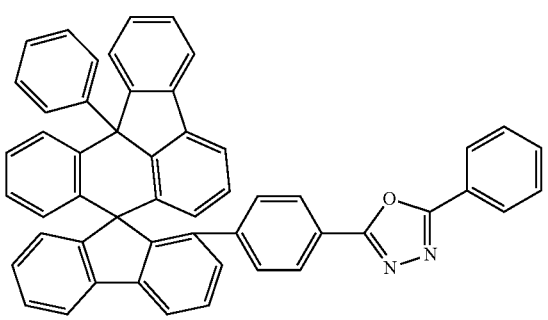
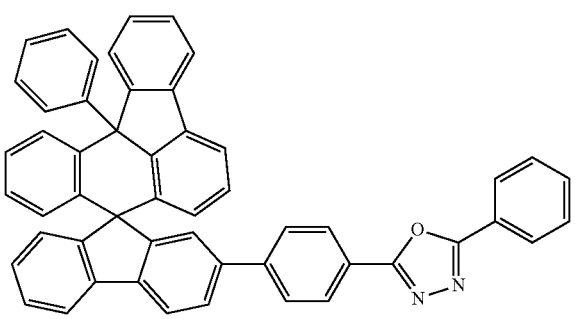

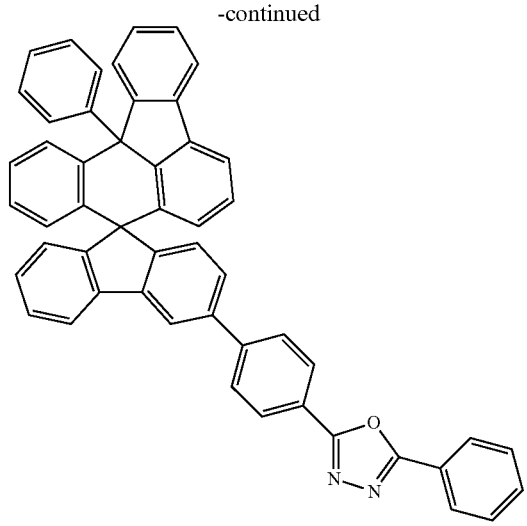
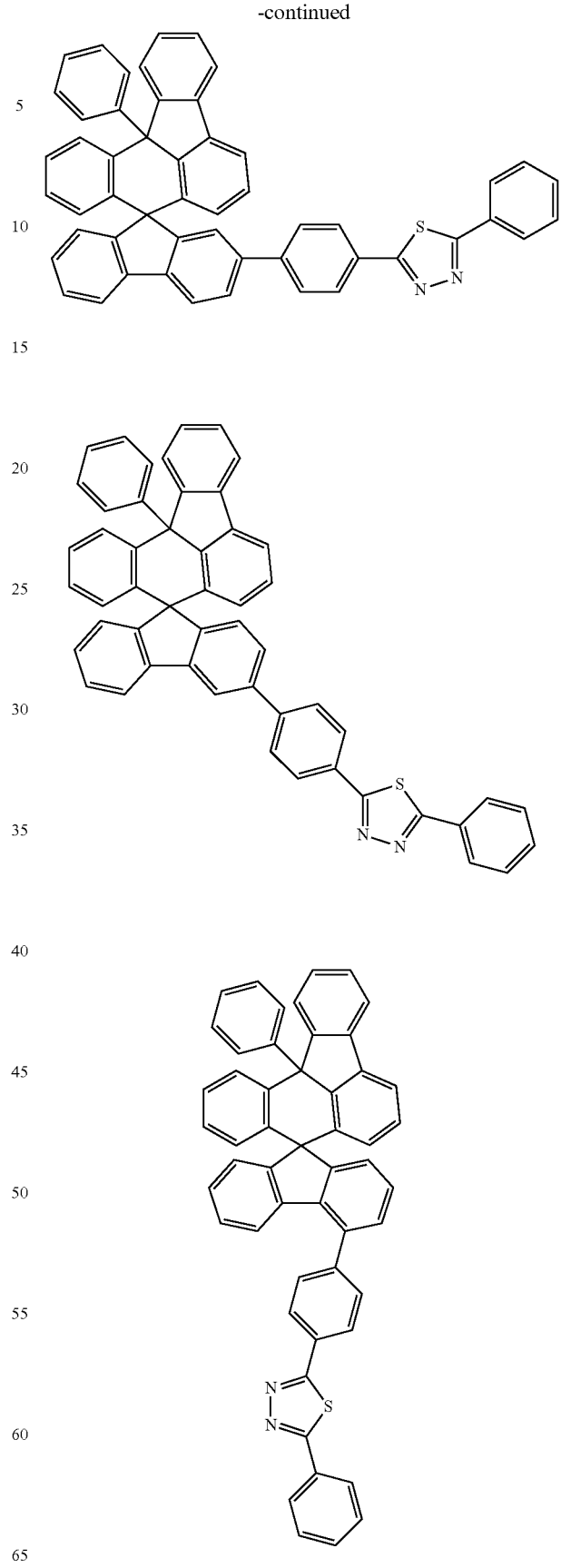

57
-continued
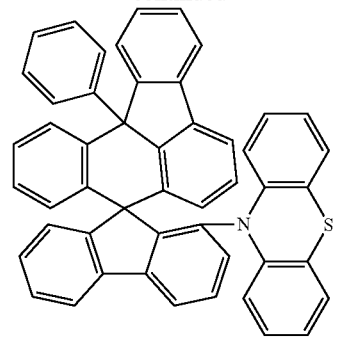
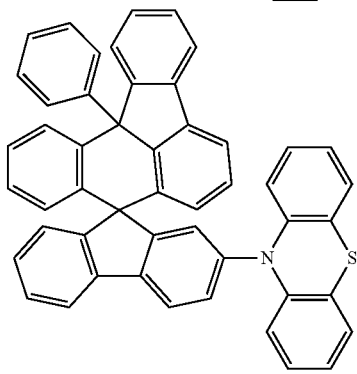
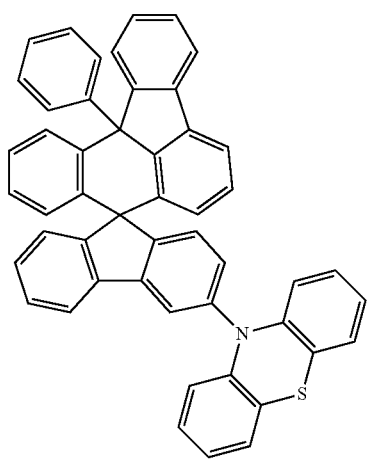
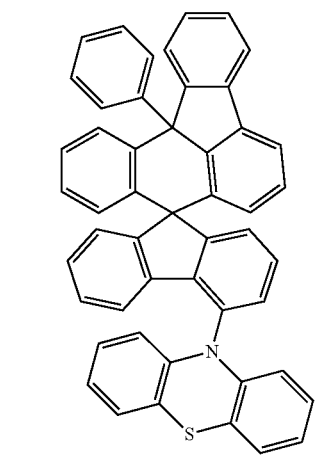
58
-continued
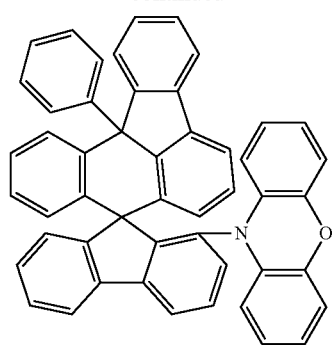
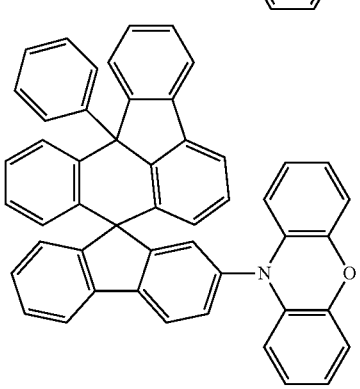
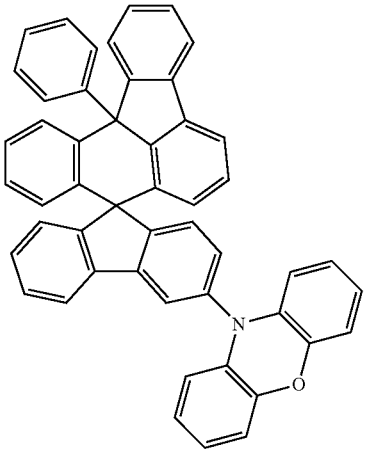
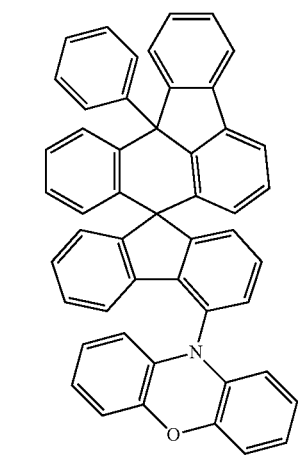

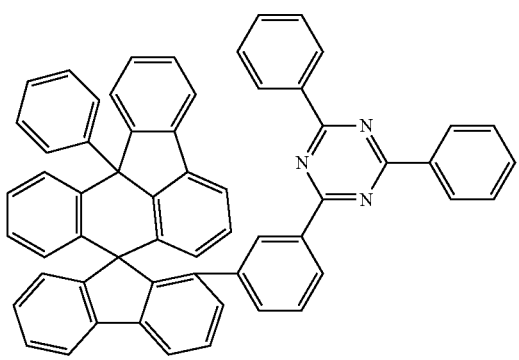
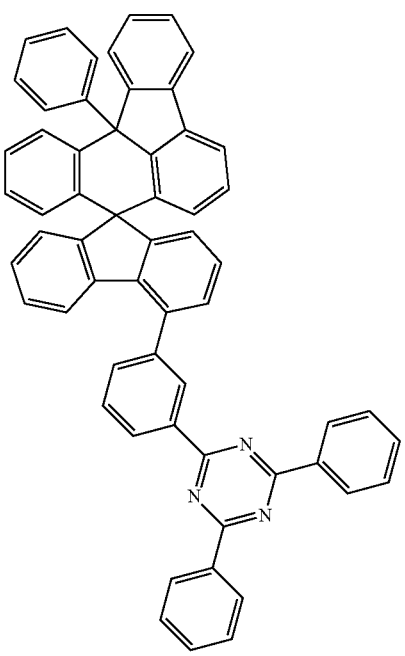
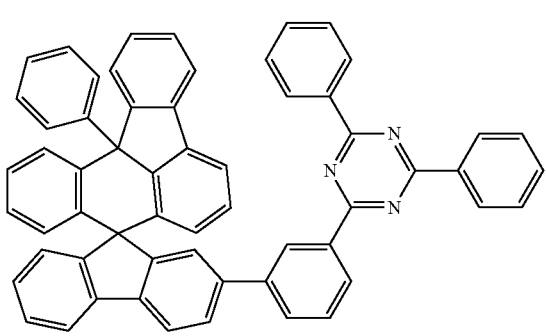
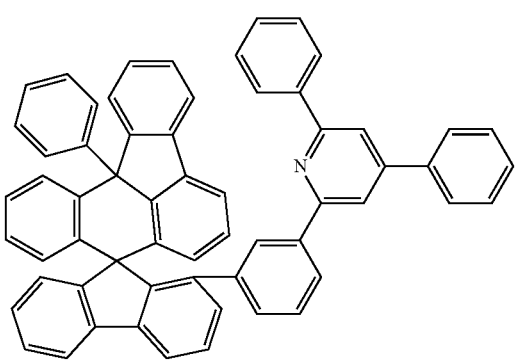
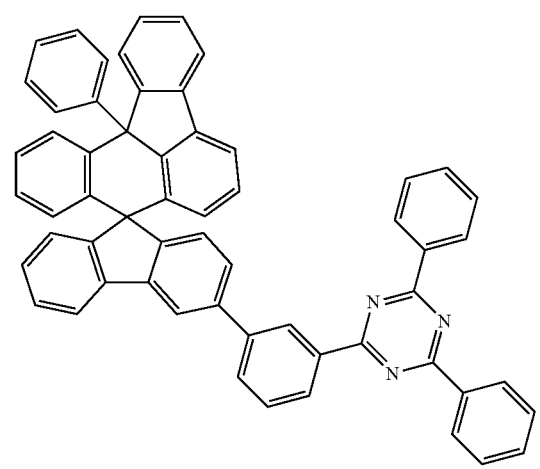
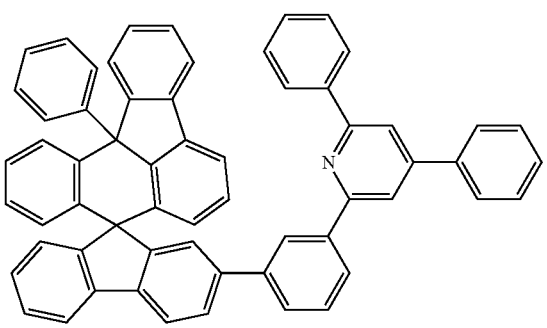

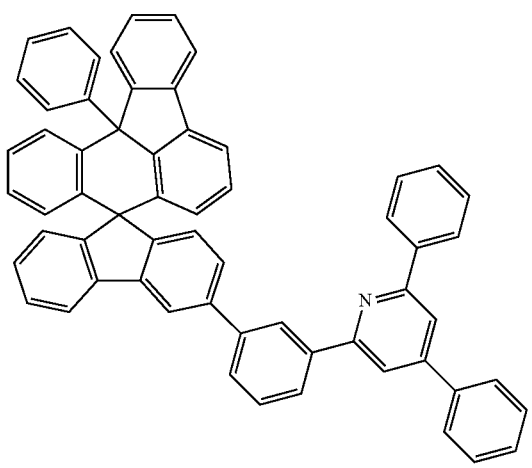
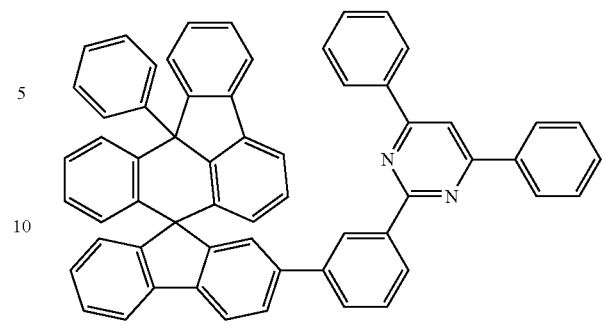
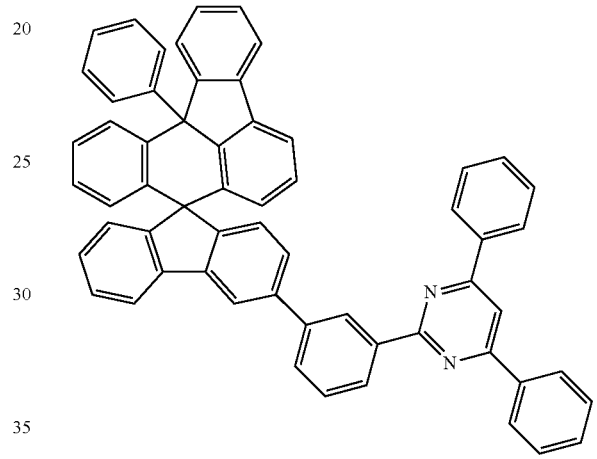
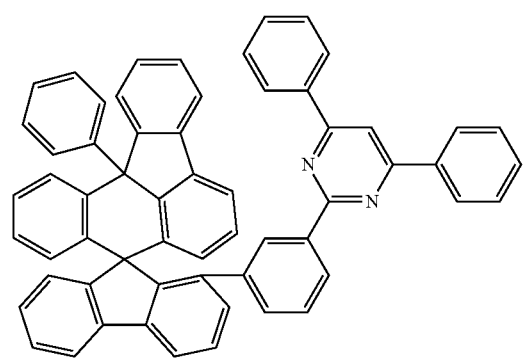
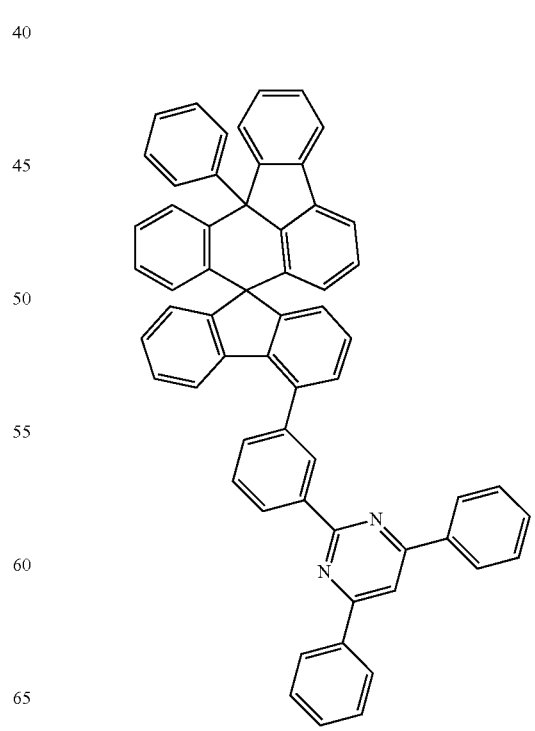

-continued
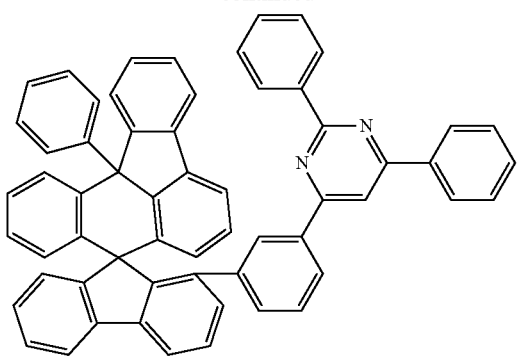
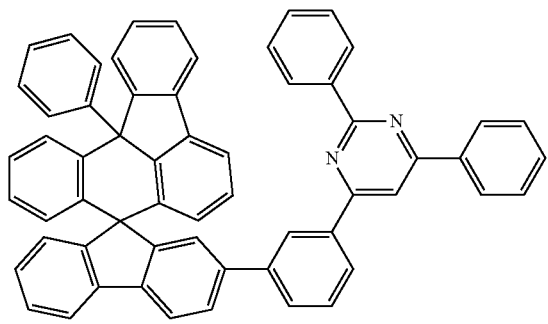
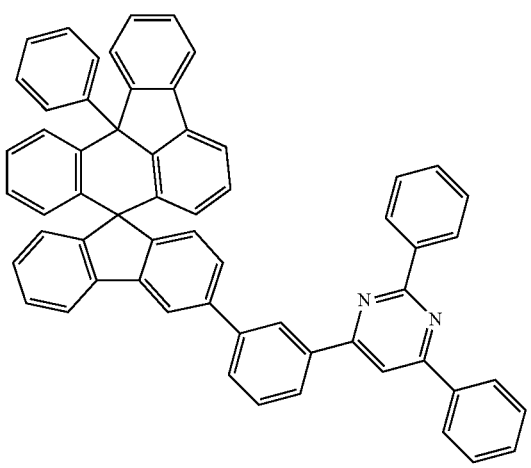
-continued
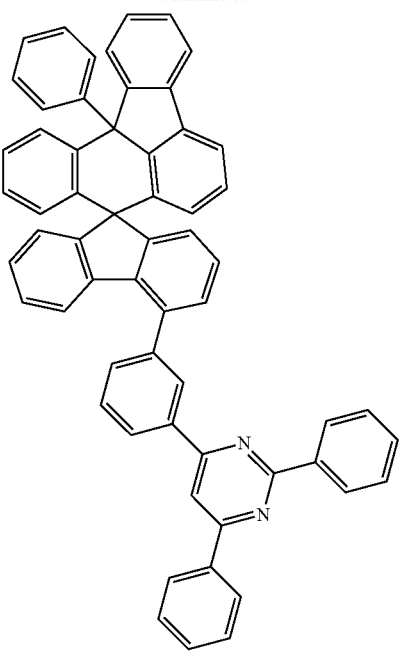
The compound represented by Chemical Formula 1 may be prepared based on preparation examples described below.
According to one embodiment, the compound represented by Chemical Formula 1 may be prepared through steps of the following Reaction Formulae 1-1 and 1-2.
[Reaction Formula 1-1]
(Compounds A, A-1, B, B-1, C, C-1, D, D-1)
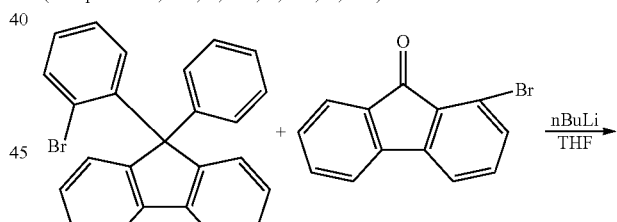
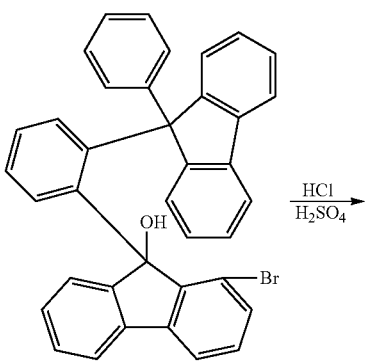

65
-continued
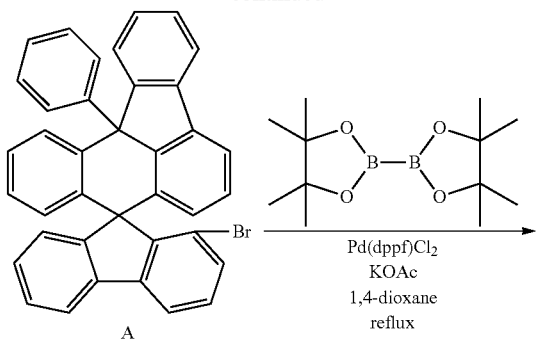
A
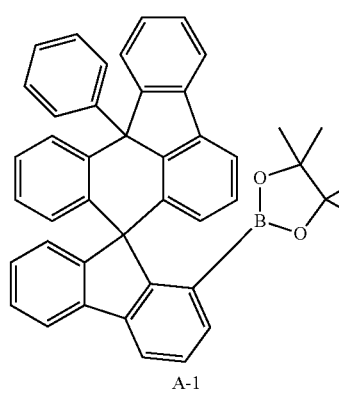
A-1
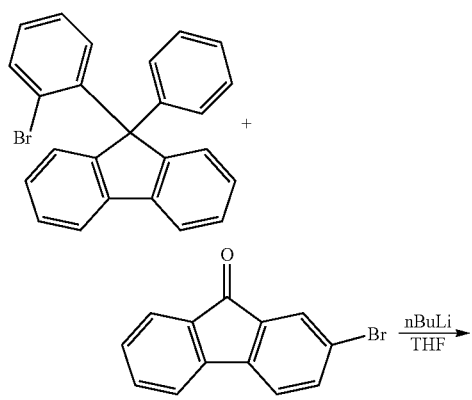
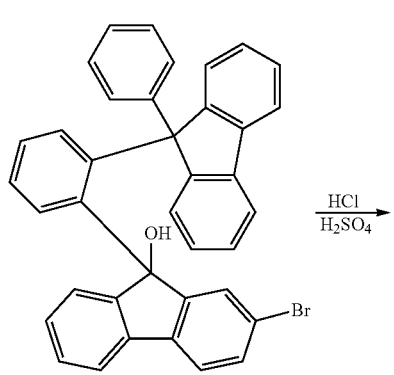
66
-continued
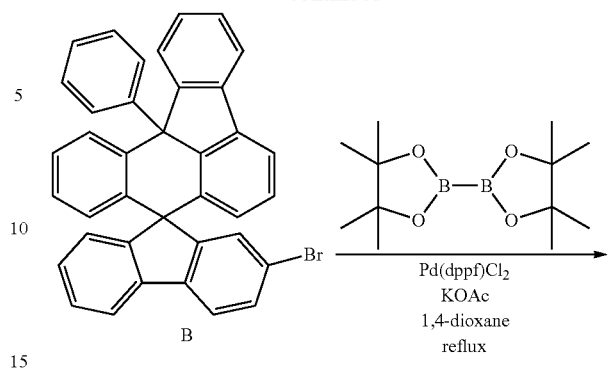
B
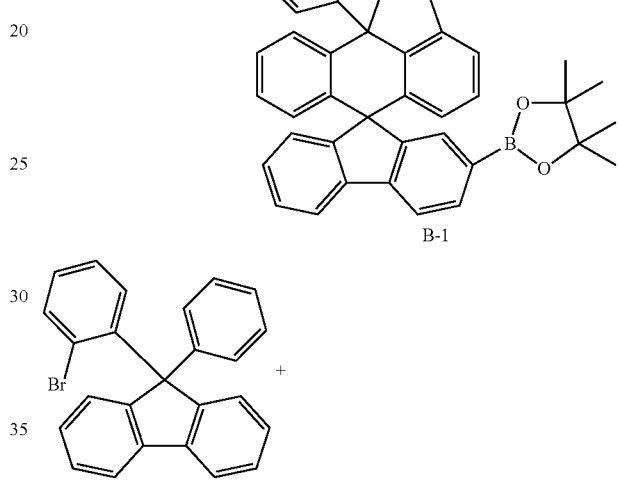
B-1
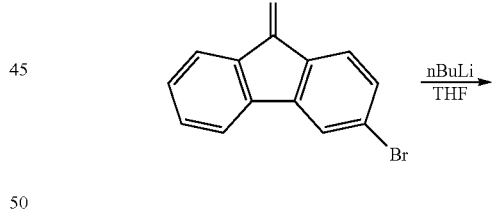
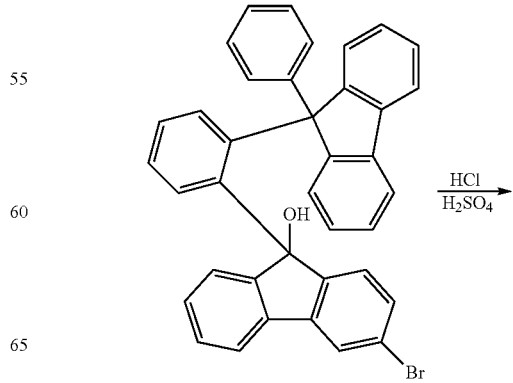

67
-continued
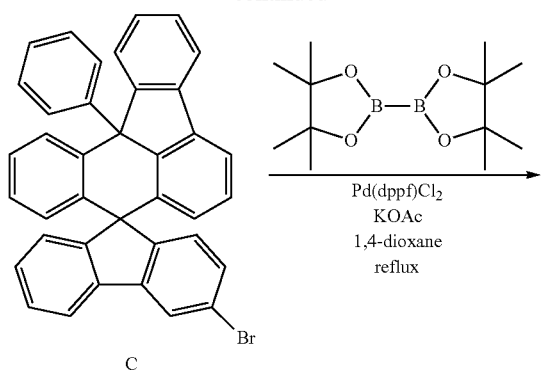
68
-continued
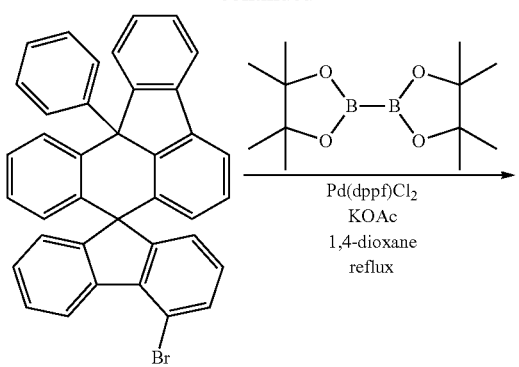
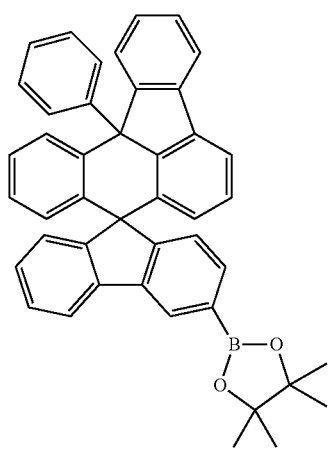
C-1
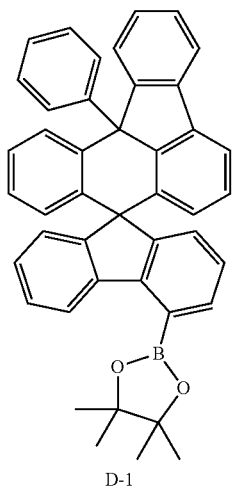
D-1
[Reaction Formula 1-2]
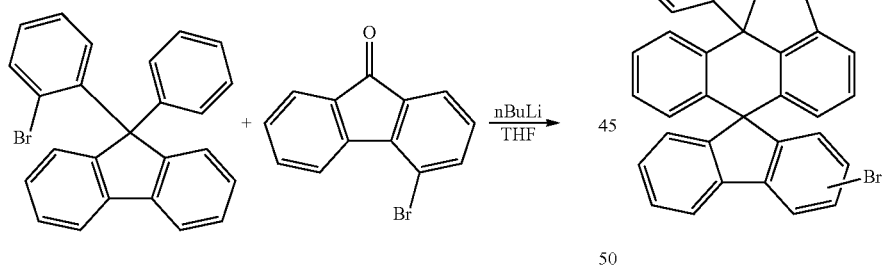
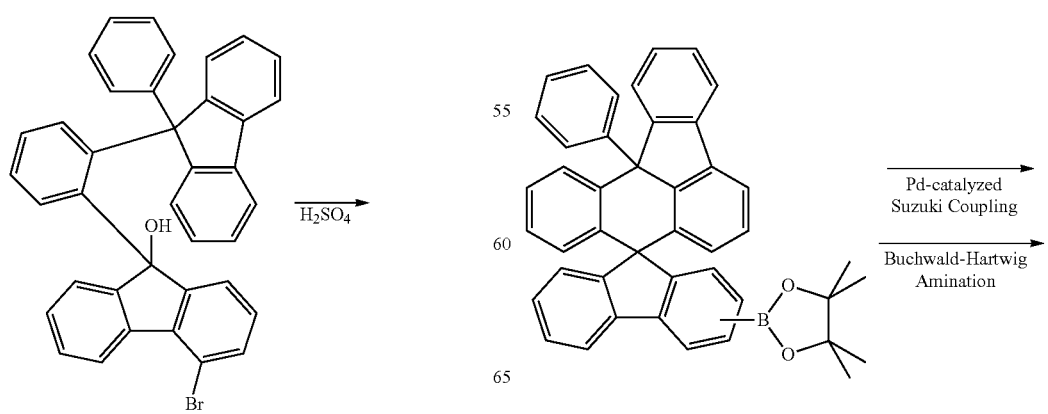

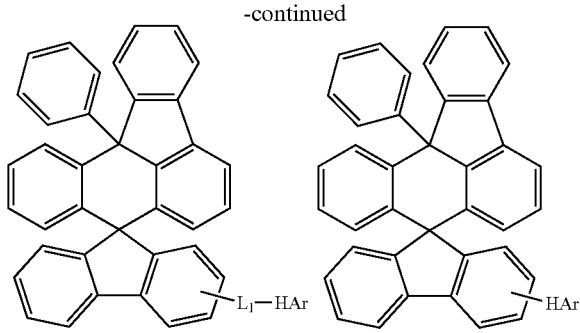

In the reaction formulae, definitions of L1 and HAr are the same as those described above.

Those skilled in the art may modify the reaction conditions, reagents and starting materials described in the reaction formulae described above using technologies known in the art, and may further introduce substituents as necessary.

In addition, the present specification provides an organic light emitting device including the compound represented by Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the organic material layer includes a hole injection layer, a hole transfer layer or a layer carrying out hole injection and transfer at the same time, and the hole injection layer, the hole transfer layer, or the layer carrying out hole injection and transfer at the same time includes the compound of Chemical Formula 1.

In another embodiment, the organic material layer includes a light emitting layer, and the light emitting layer includes the compound of Chemical Formula 1. According to one embodiment, the compound of Chemical Formula 1 performs a role of a host of the light emitting layer, and in this case, the light emitting layer may further include a dopant. As the dopant, those known in the art may be used, and for example, phosphorescent dopants, specifically, iridium-based dopants may be used therewith. As the iridium-based dopant, Ir(ppy)$_3$, [(piq)$_2$Ir(acac)] and the like may be used.

In one embodiment of the present specification, the organic material layer includes an electron suppression layer, and the electron suppression layer includes the compound of Chemical Formula 1.

In one embodiment of the present specification, the electron transfer layer, the electron injection layer, or the layer carrying out electron transfer and electron injection at the same time includes the compound of Chemical Formula 1.

In another embodiment, the organic material layer includes a light emitting layer and an electron transfer layer, and the electron transfer layer includes the compound of Chemical Formula 1.

The electron transfer layer may further include an n-type dopant as necessary. As the n-type dopant, those known in the art may be used, and for example, Li complexes, specifically, LiQ, may be used.

According to one embodiment of the present specification, the organic material layer includes a light emitting layer, and the light emitting layer includes a compound represented by the following Chemical Formula 1-A.

[Chemical Formula 1-A]

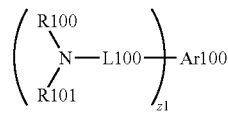

In Chemical Formula 1-A, z1 is an integer of 1 or greater, and when z1 is 2 or greater, structures in the parentheses are the same as or different from each other, Ar100 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, L100 is a direct bond; a substituted or unsubstituted arylene group; or a substituted or unsubstituted heteroarylene group, R100 and R101 are the same as or different from each other, and each independently a substituted or unsubstituted aryl group; a substituted or unsubstituted alkyl group; a substituted or unsubstituted silyl group; a substituted or unsubstituted arylalkyl group; or a substituted or unsubstituted heterocyclic group, or may bond to each other to form a substituted or unsubstituted ring.

According to one embodiment of the present specification, the light emitting layer includes the compound represented by Chemical Formula 1-A as a dopant of the light emitting layer.

According to one embodiment of the present specification, L100 is a direct bond.

According to one embodiment of the present specification, z1 is 2.

According to one embodiment of the present specification, Ar100 is a divalent pyrene group unsubstituted or substituted with deuterium, a methyl group, an ethyl group, an iso-propyl group or a tert-butyl group; or a divalent chrysene group unsubstituted or substituted with deuterium, a methyl group, an ethyl group, an iso-propyl group or a tert-butyl group.

According to one embodiment of the present specification, Ar100 is a divalent pyrene group unsubstituted or substituted with deuterium, a methyl group, an ethyl group, an iso-propyl group or a tert-butyl group.

According to one embodiment of the present specification, Ar100 is a divalent pyrene group.

According to one embodiment of the present specification, R100 and R101 are the same as or different from each other, and each independently a substituted or unsubstituted aryl group having 6 to 60 carbon atoms; or a substituted or unsubstituted heterocyclic group having 2 to 60 carbon atoms.

According to one embodiment of the present specification, R100 and R101 are the same as or different from each other, and each independently an aryl group having 6 to 60 carbon atoms unsubstituted or substituted with deuterium, an alkyl group, a nitrile group, an aryl group, an alkylsilyl group or an alkylgermanium group; or a heterocyclic group having 2 to 60 carbon atoms unsubstituted or substituted with deuterium, an alkyl group, a nitrile group, an aryl group, an alkylsilyl group or an alkylgermanium group.

According to one embodiment of the present specification, R100 and R101 are the same as or different from each other, and each independently an aryl group having 6 to 60 carbon atoms unsubstituted or substituted with deuterium, a methyl group, an ethyl group, an iso-propyl group, a tert-butyl group, a nitrile group, a phenyl group, a trimethylsilyl group or a trimethylgermanium group; or a heterocyclic group having 2 to 60 carbon atoms unsubstituted or substituted with deuterium, a methyl group, an ethyl group, an iso-propyl group, a tert-butyl group, a nitrile group, a phenyl group, a trimethylsilyl group or a trimethylgermanium group.

According to one embodiment of the present specification, R100 and R101 are the same as or different from each other, and each independently a phenyl group unsubstituted or substituted with deuterium, a methyl group, an ethyl group, an iso-propyl group, a tert-butyl group, a nitrile group, a phenyl group, a trimethylsilyl group or a trimethylgermanium group; a biphenyl group unsubstituted or substituted with deuterium, a methyl group, an ethyl group, an iso-propyl group, a tert-butyl group, a nitrile group, a phenyl group, a trimethylsilyl group or a trimethylgermanium group; a terphenyl group unsubstituted or substituted with deuterium, a methyl group, an ethyl group, an iso-propyl group, a tert-butyl group, a nitrile group, a phenyl group, a trimethylsilyl group or a trimethylgermanium group; or a dibenzofuran group unsubstituted or substituted with deuterium, a methyl group, an ethyl group, an iso-propyl group, a tert-butyl group, a nitrile group, a phenyl group, a trimethylsilyl group or a trimethylgermanium group.

According to one embodiment of the present specification, R100 and R101 are the same as or different from each other, and each independently a phenyl group unsubstituted or substituted with a trimethylgermanium group.

According to one embodiment of the present specification, R100 is a phenyl group.

According to one embodiment of the present specification, R101 is a phenyl group substituted with a trimethylgermanium group.

According to one embodiment of the present specification, Chemical Formula 1-A may be selected from among the following compounds.

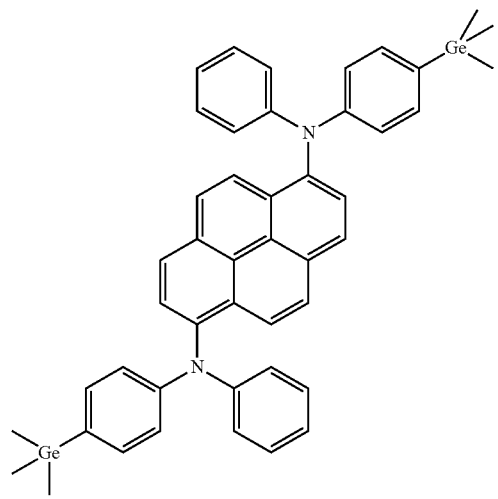

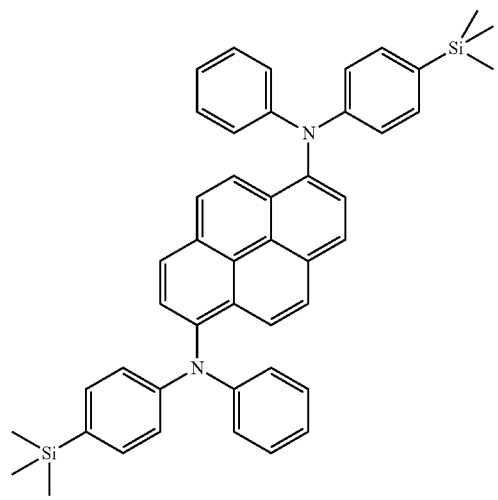

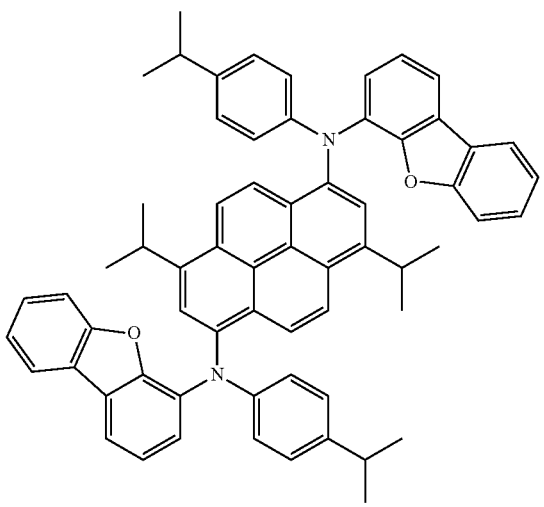

73
-continued
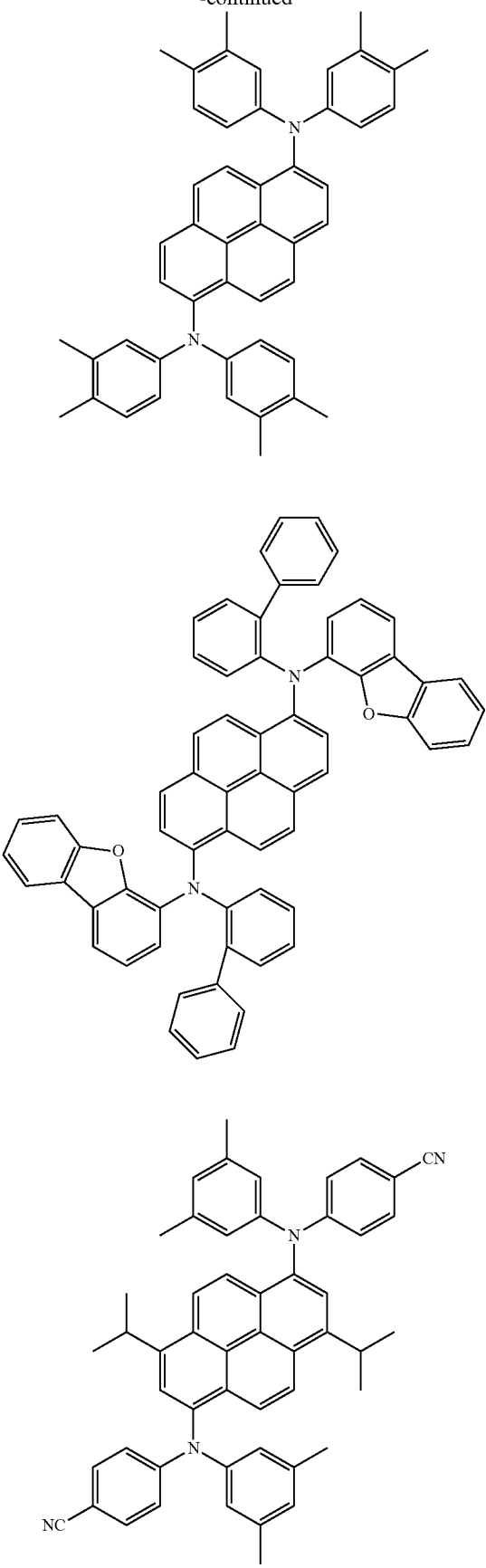
74
-continued
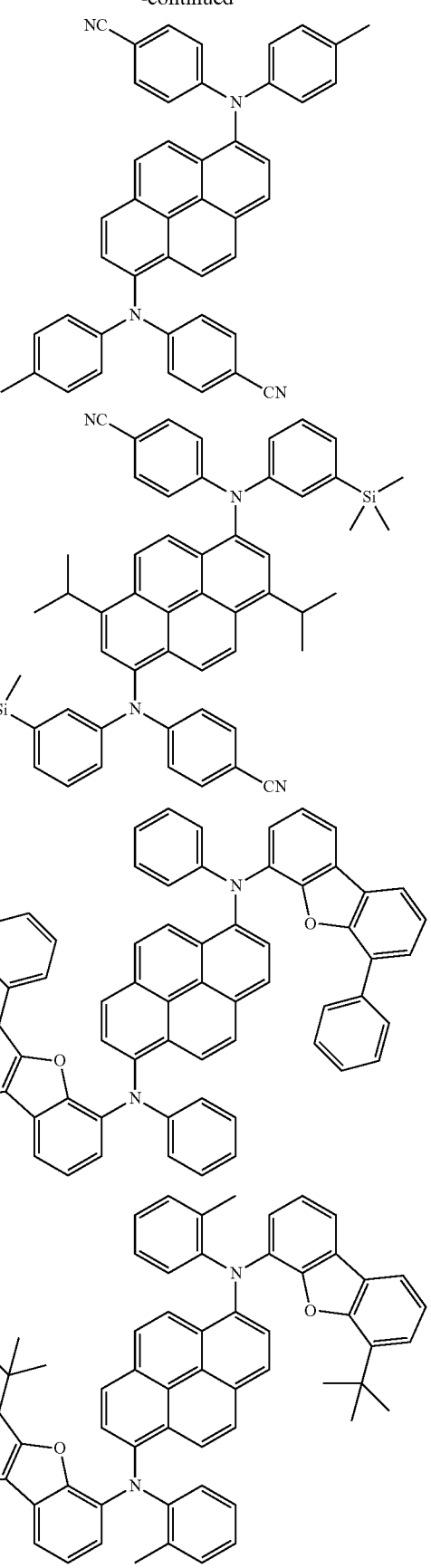

-continued

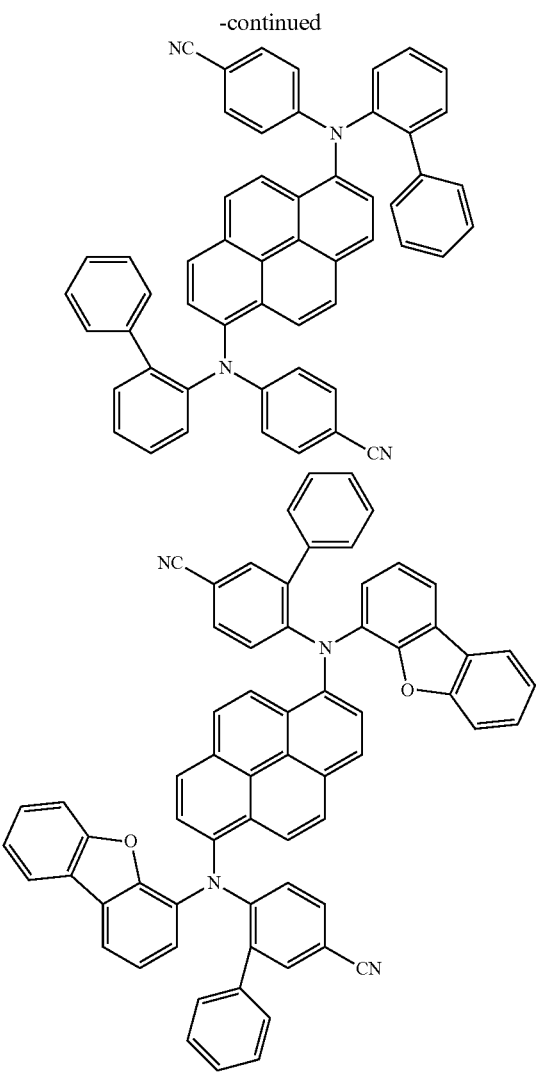

According to one embodiment of the present specification, the organic material layer includes a light emitting layer, and the light emitting layer includes a compound represented by the following Chemical Formula 1-B.

[Chemical Formula 1-B]

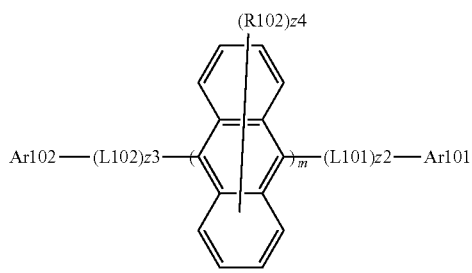

In Chemical Formula 1-B,

Ar101 and Ar102 are the same as or different from each other, and each independently a substituted or unsubstituted aryl group; or a substituted or unsubstituted heterocyclic group, L101 and L102 are the same as or different from each other, and each independently a direct bond; a substituted or unsubstituted arylene group; or a substituted or unsubstituted heteroarylene group, R102 is hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, z2 and z3 are the same as or different from each other and each independently an integer of 1 or 2, z4 is an integer of 0 to 8, and when z2 to z4 are 2 or greater, substituents in the parentheses are the same as or different from each other, m is an integer of 1 or greater, and when m is an integer of 2 or greater, substituents in the parentheses are the same as or different from each other.

According to one embodiment of the present specification, the light emitting layer includes the compound represented by Chemical Formula 1-B as a host of the light emitting layer.

According to one embodiment of the present specification, Ar101 and Ar102 are the same as or different from each other, and each independently a substituted or unsubstituted aryl group having 6 to 60 carbon atoms; or a substituted or unsubstituted heterocyclic group having 2 to 60 carbon atoms.

According to one embodiment of the present specification, Ar101 and Ar102 are the same as or different from each other, and each independently an aryl group having 6 to 60 carbon atoms unsubstituted or substituted with an alkyl group, an aryl group or a heterocyclic group; or a heterocyclic group having 2 to 60 carbon atoms unsubstituted or substituted with an alkyl group, an aryl group or a heterocyclic group.

According to one embodiment of the present specification, Ar101 and Ar102 are the same as or different from each other, and each independently a phenyl group unsubstituted or substituted with an aryl group or a heterocyclic group; a biphenyl group unsubstituted or substituted with an aryl group or a heterocyclic group; a terphenyl group unsubstituted or substituted with an aryl group or a heterocyclic group; a naphthyl group unsubstituted or substituted with an aryl group or a heterocyclic group; a fluorene group unsubstituted or substituted with an alkyl group, an aryl group or a heterocyclic group; a phenanthrene group unsubstituted or substituted with an aryl group or a heterocyclic group; or a triphenylene group unsubstituted or substituted with an aryl group or a heterocyclic group.

According to one embodiment of the present specification, Ar101 and Ar102 are the same as or different from each other, and each independently a phenyl group; a biphenyl group; a terphenyl group; a naphthyl group; a fluorene group unsubstituted or substituted with a methyl group or a phenyl group; a phenanthrene group; or a triphenylene group.

According to one embodiment of the present specification, Ar101 is a 2-naphthyl group.

According to one embodiment of the present specification, Ar102 is a phenyl group.

According to one embodiment of the present specification, L101 and L102 are the same as or different from each other, and each independently a direct bond; a phenylene group; or a naphthylene group.

According to one embodiment of the present specification, L101 is a phenylene group.

According to one embodiment of the present specification, L102 is a direct bond.

According to one embodiment of the present specification, z2 is 1.

According to one embodiment of the present specification, z3 is 1.

According to one embodiment of the present specification, R102 is hydrogen.

According to one embodiment of the present specification, m is 1.

According to one embodiment of the present specification, m is 2.

According to one embodiment of the present specification, Chemical Formula 1-B may be selected from among the following compounds.

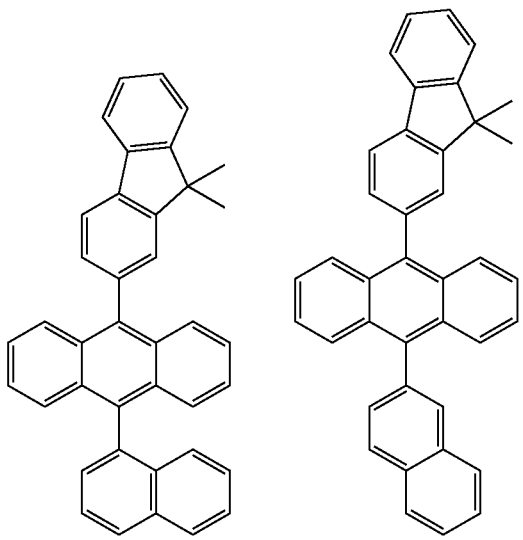

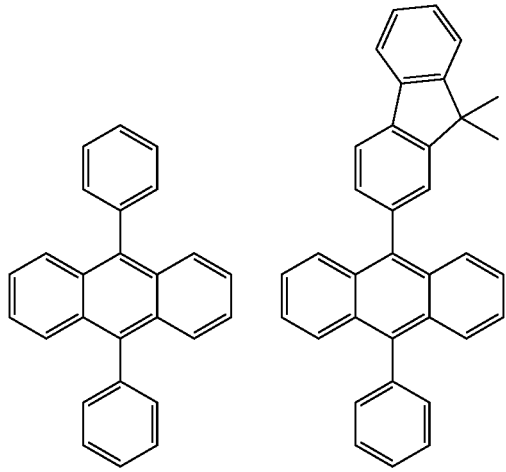

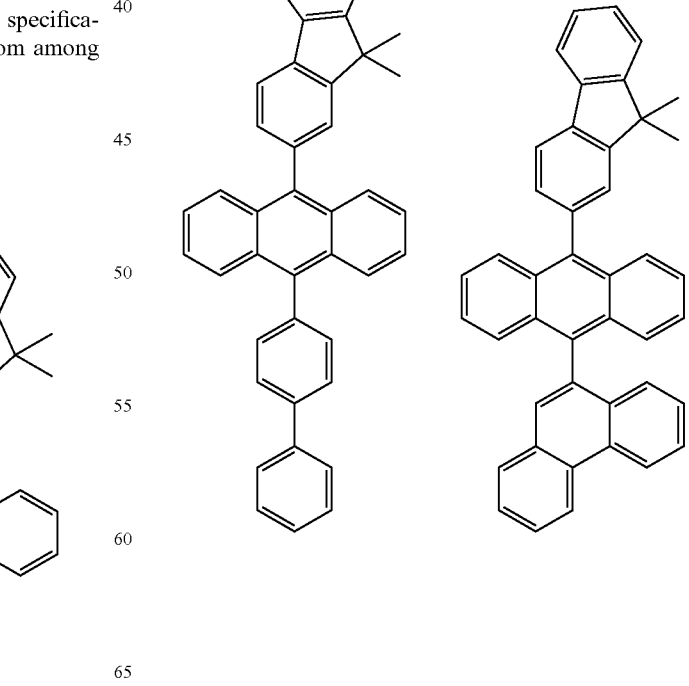

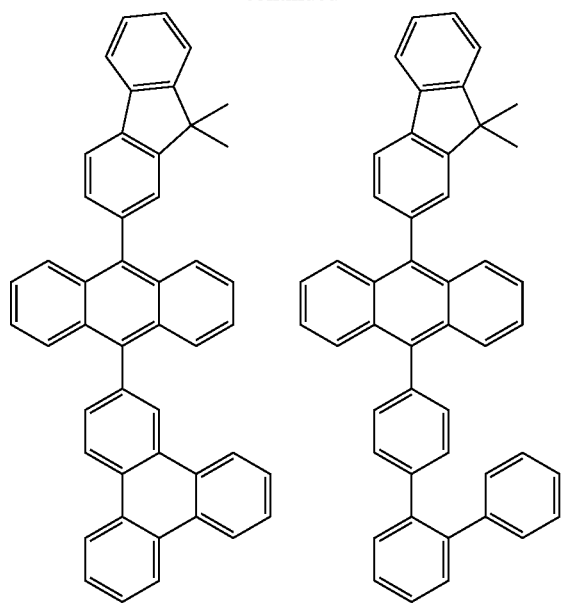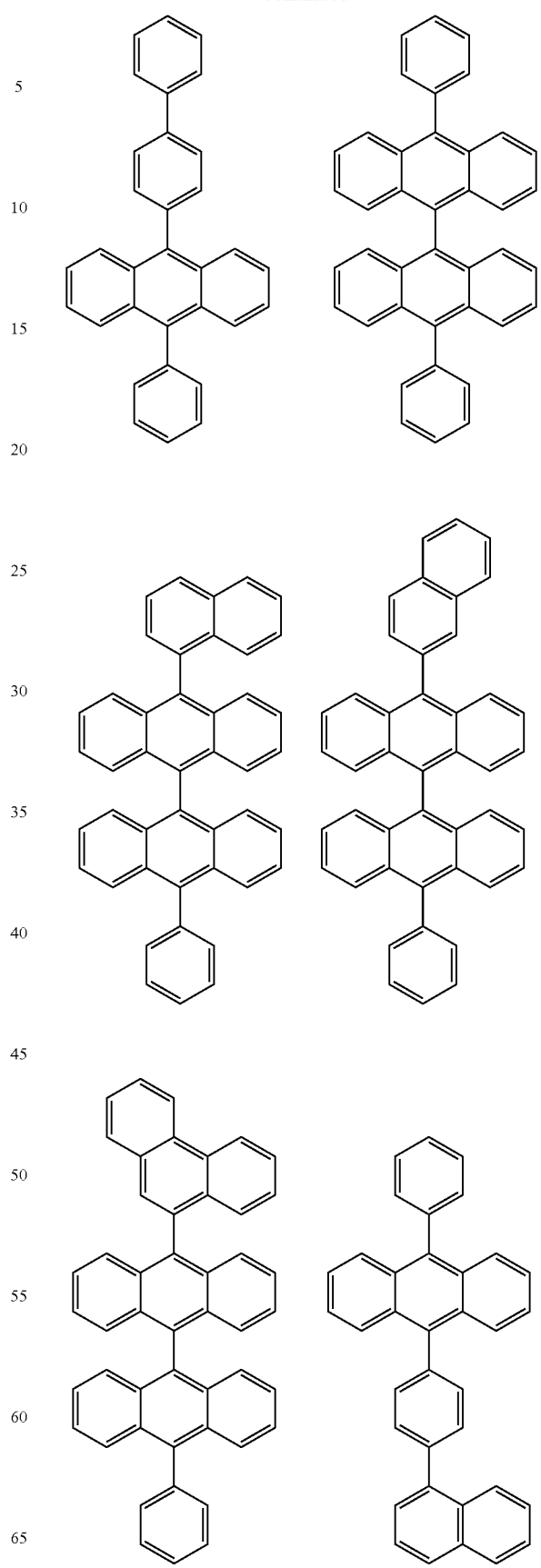

-continued
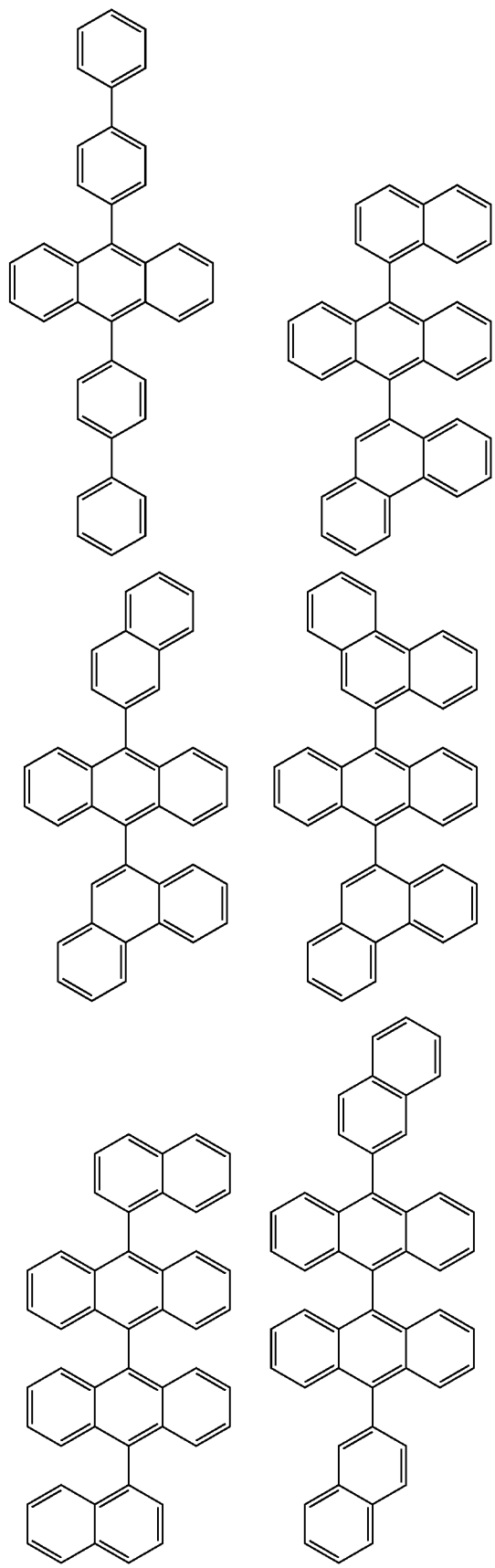
-continued
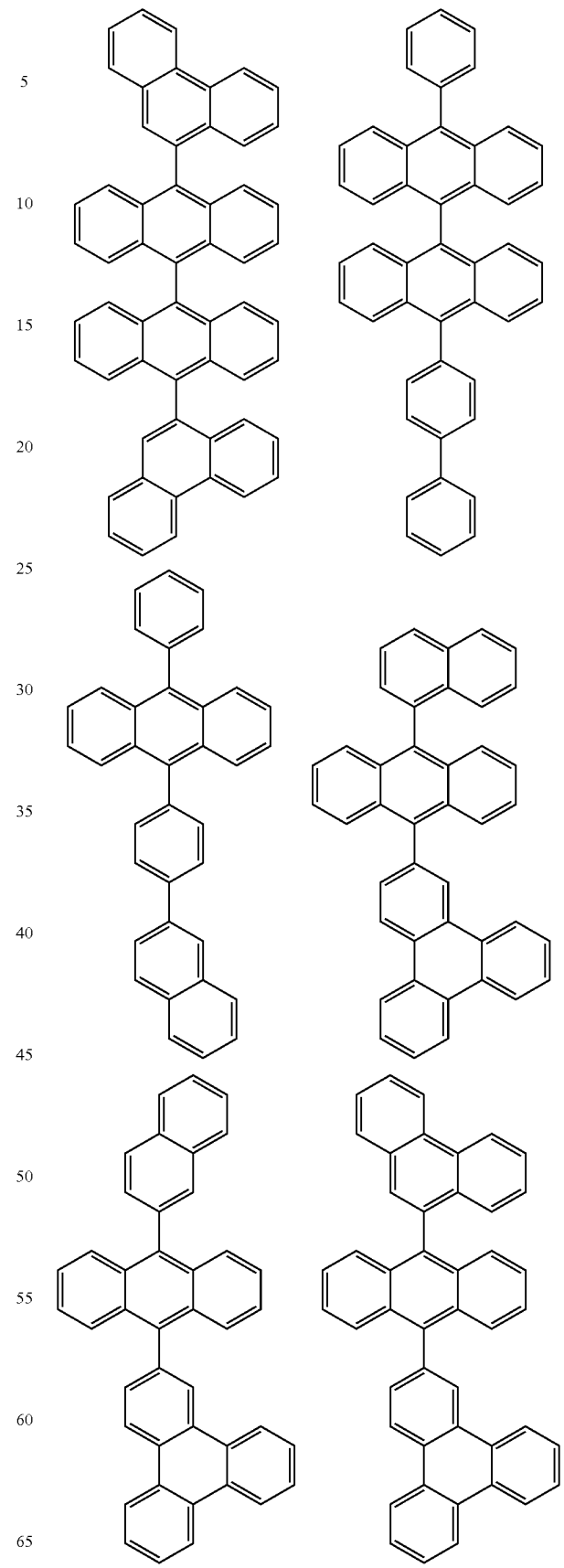

-continued
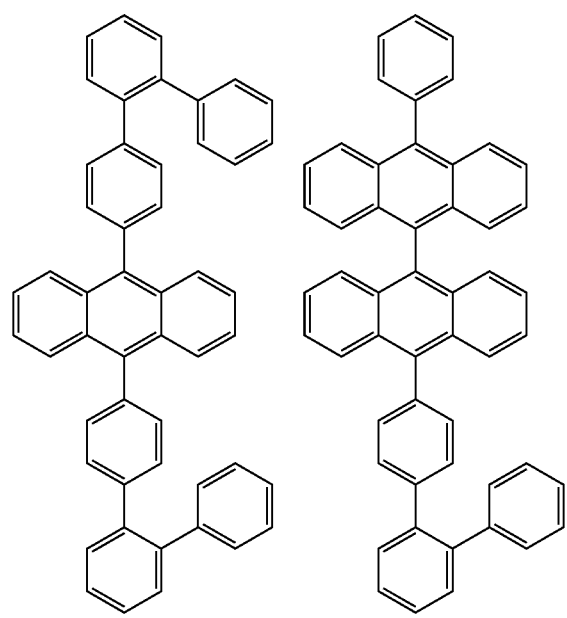
-continued
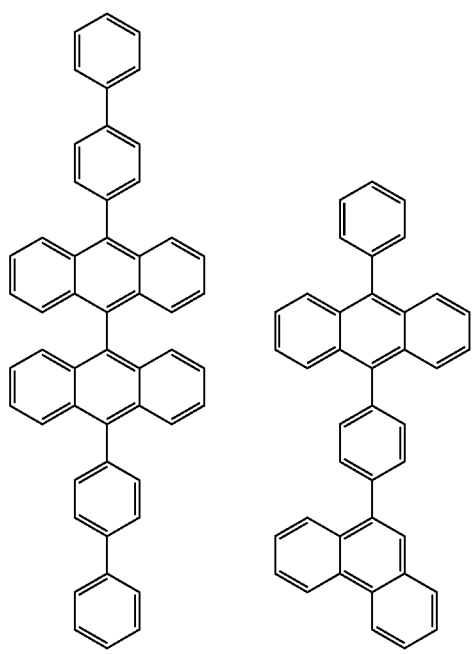
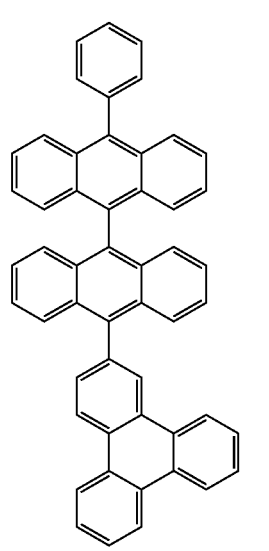
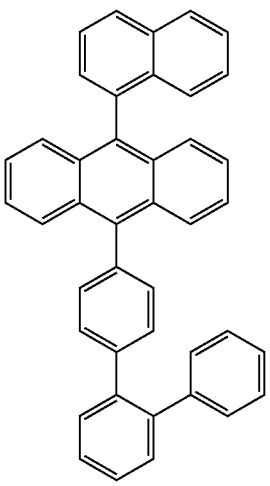

-continued
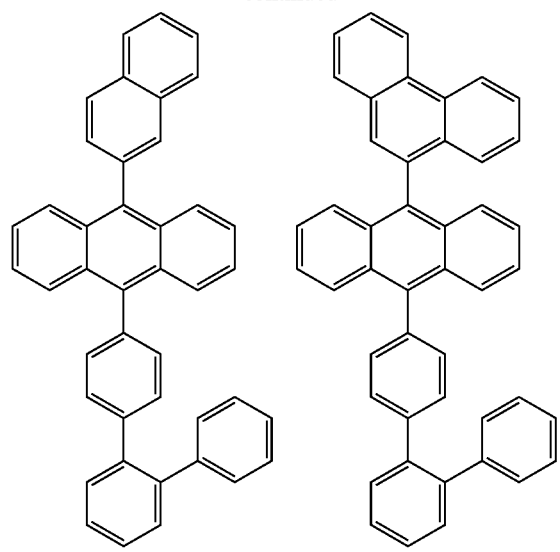
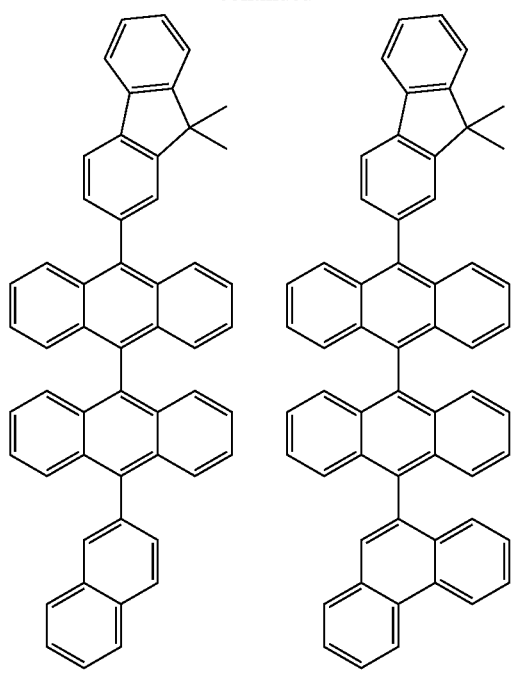
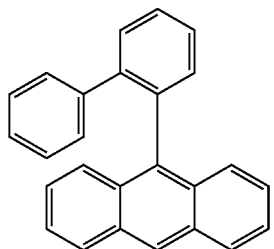
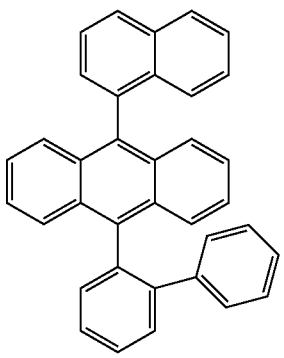
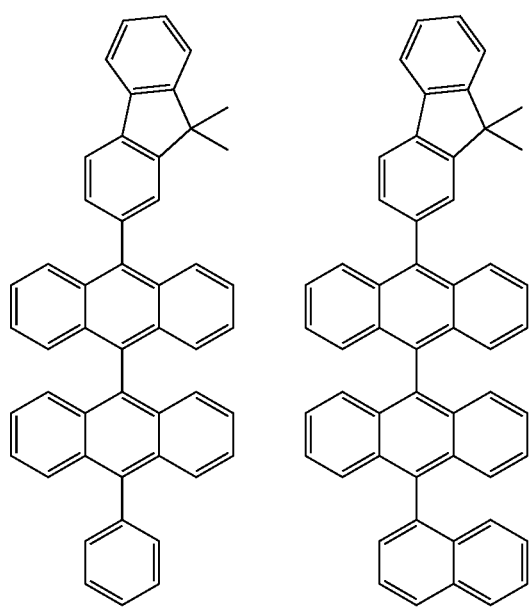

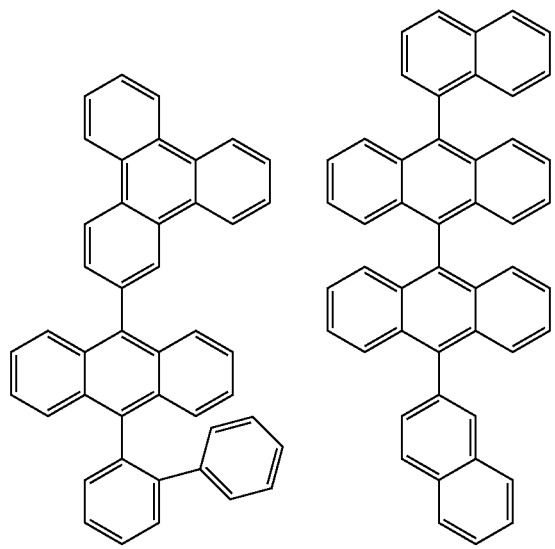
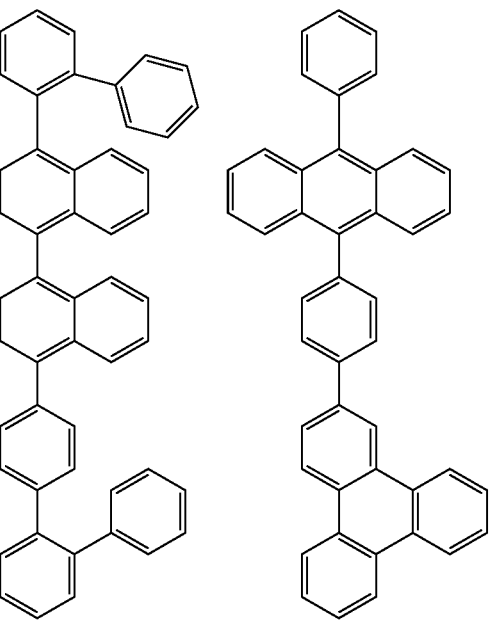
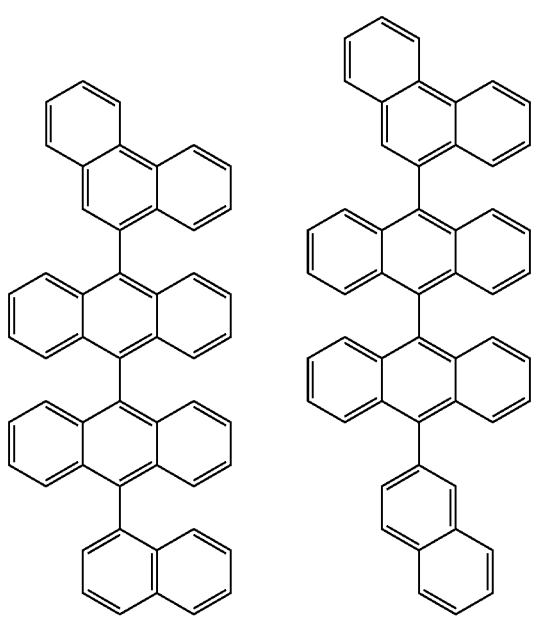
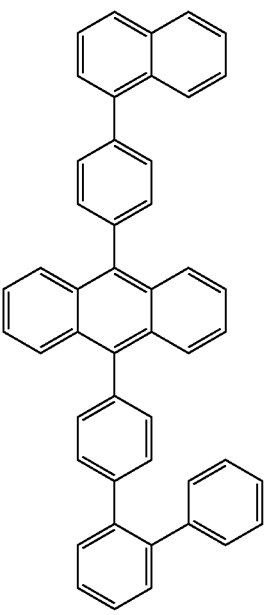

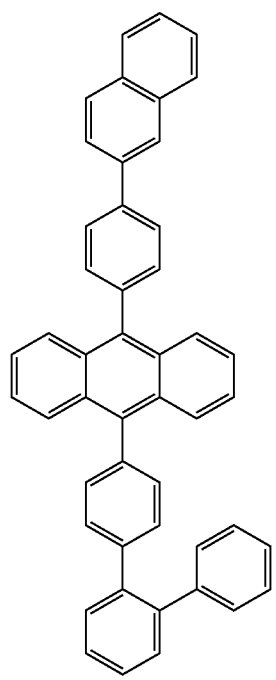 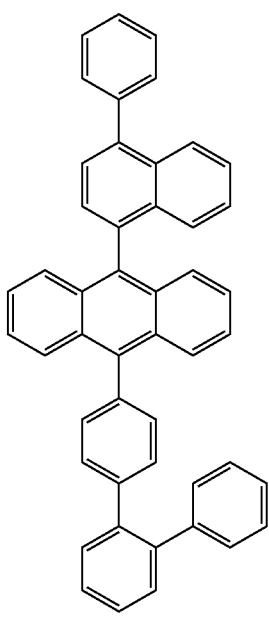 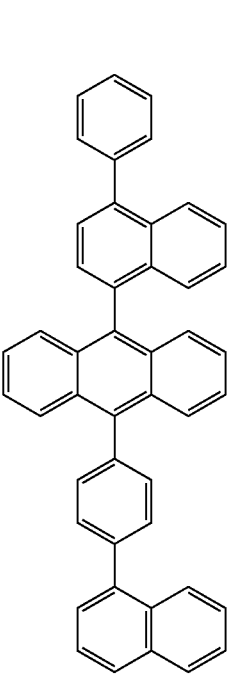 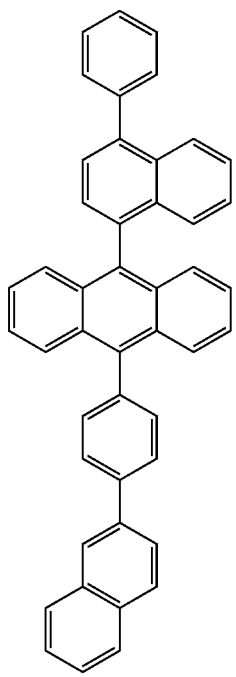
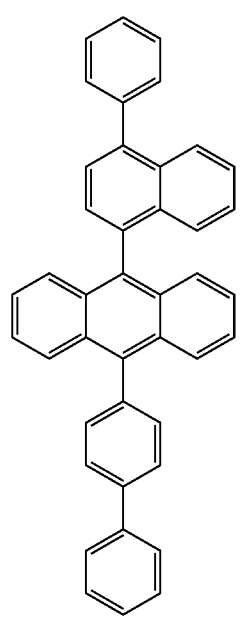 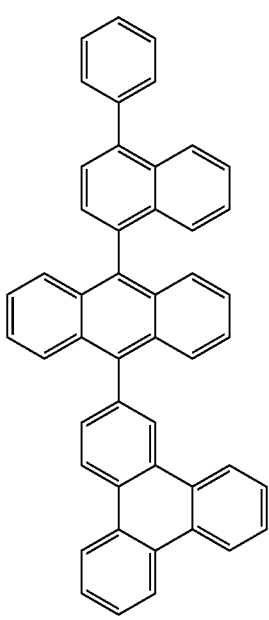 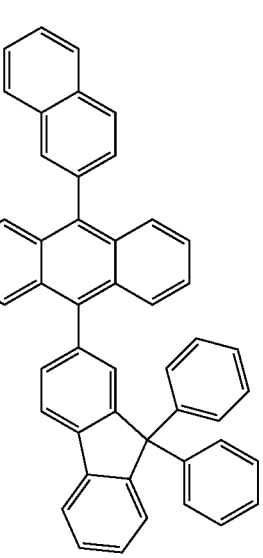 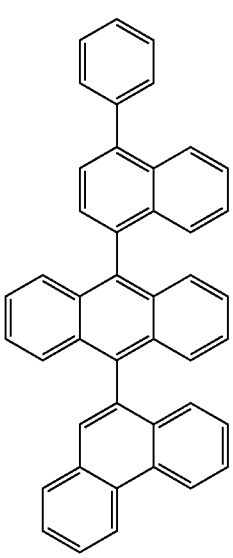

-continued

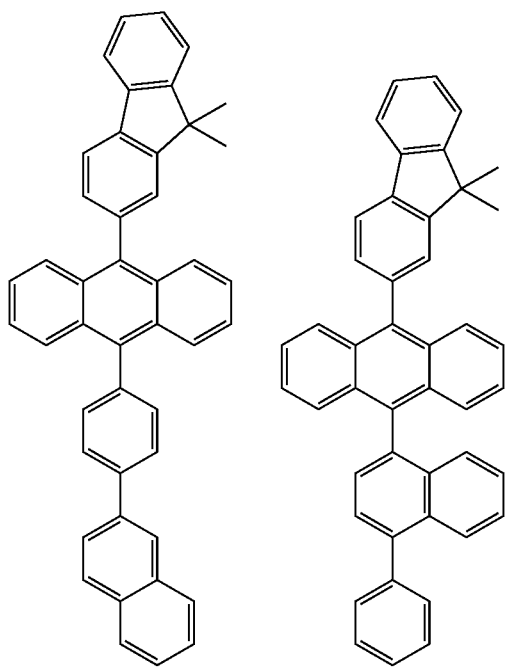

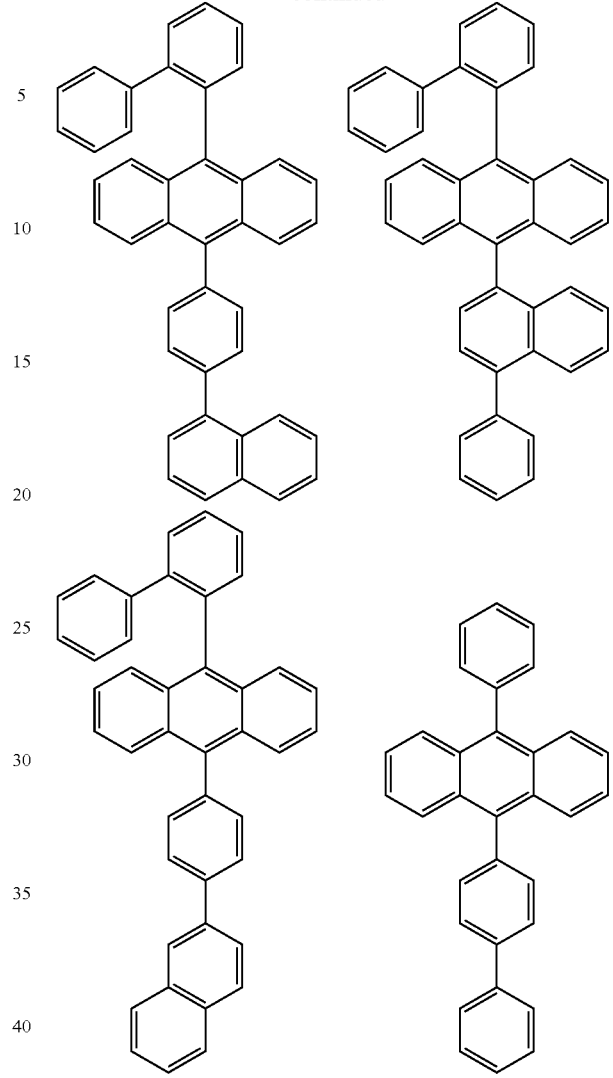

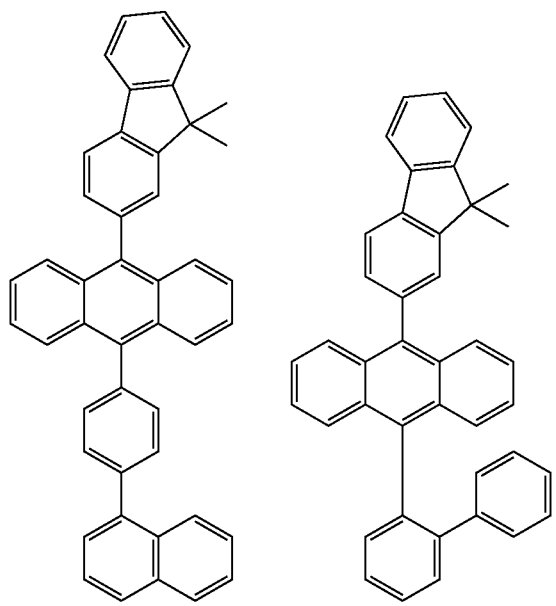

According to one embodiment of the present specification, the organic material layer includes a light emitting layer, the light emitting layer includes the compound represented by Chemical Formula 1-A as a dopant of the light emitting layer, and includes the compound represented by Chemical Formula 1-B as a host of the light emitting layer.

One embodiment of the present specification provides an organic light emitting device including a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the compound having a spiro structure. In one embodiment, as the two or more organic material layers, two or more may be selected from the group consisting of an electron transfer layer, an electron injection layer, a layer carrying out electron transfer and electron injection at the same time, and a hole blocking layer.

In one embodiment of the present specification, the organic material layer includes two or more electron transfer layers, and at least one of the two or more electron transfer layers includes the compound having a spiro structure.

Specifically, in one embodiment of the present specification, the compound having a spiro structure the compound may be included in one of the two or more electron transfer layers, or may be included in each of the two or more electron transfer layers.

In addition, in one embodiment of the present specification, when the compound having a spiro structure is included in each of the two or more electron transfer layers, materials other than the compound having a spiro structure may be the same as or different from each other.

In another embodiment, the organic light emitting device may be an organic light emitting device having a structure of consecutively laminating an anode, one or more organic material layers and a cathode on a substrate (normal type).

In another embodiment, the organic light emitting device may be an organic light emitting device having a reverse structure of consecutively laminating a cathode, one or more organic material layers and an anode on a substrate (inverted type).

For example, structures of an organic light emitting device according to one embodiment of the present specification are illustrated in FIG. 1 and FIG. 2.

FIG. 1 illustrates an organic light emitting device formed with a substrate (1), an anode (2), a light emitting layer (3) and a cathode (4). In such a structure, the compound may be included in the light emitting layer.

FIG. 2 illustrates an organic light emitting device formed with a substrate (1), an anode (2), a hole injection layer (5), a hole transfer layer (6), a light emitting layer (3), an electron transfer layer (7) and a cathode (4). In such a structure, the compound may be included in one or more layers of the hole injection layer, the hole transfer layer, the light emitting layer and the electron transfer layer.

The organic light emitting device of the present specification may be manufactured using materials and methods known in the art, except that one or more layers of the organic material layers include the compound of the present specification, that is, the compound of Chemical Formula 1.

When the organic light emitting device includes a plurality of organic material layers, the organic material layers may be formed with materials the same as or different from each other.

The organic light emitting device of the present specification may be manufactured using materials and methods known in the art, except that one or more layers of the organic material layers include the compound of Chemical Formula 1, that is, the compound represented by Chemical Formula 1.

For example, the organic light emitting device of the present specification may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, the compound of Chemical Formula 1 may be formed into the organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may be manufactured by consecutively depositing a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material capable of being used in the present disclosure include metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(0-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

Preparation of the compound represented by Chemical Formula 1, and manufacture of the organic light emitting device including the same will be specifically described with reference to the following examples. However, the following examples are for illustrative purposes only, and the scope of the present specification is not limited thereto.

Preparation Example 1

Compound Synthesis of the Following Compound 1

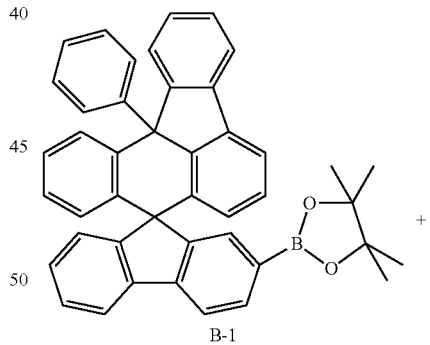

B-1

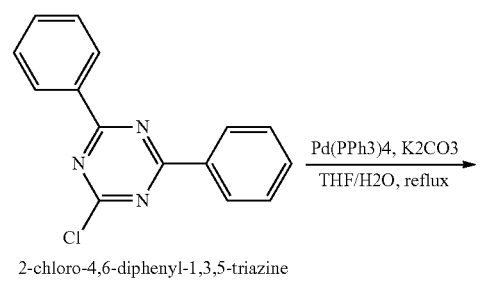

2-chloro-4,6-diphenyl-1,3,5-triazine

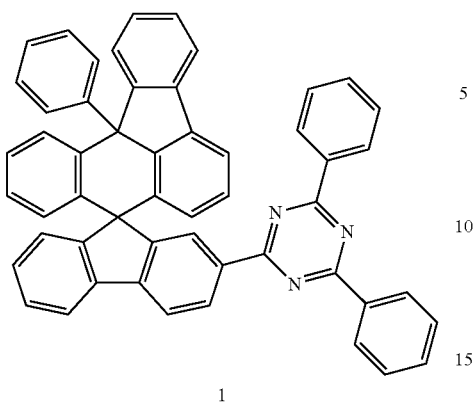

1

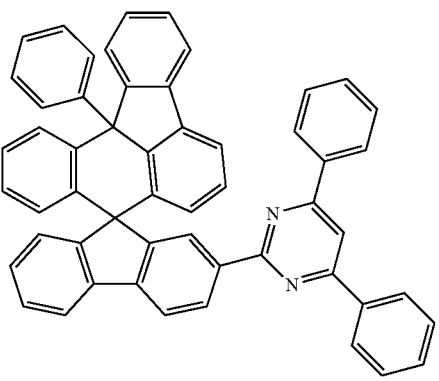

2

After completely dissolving Compound B-1 (10.0 g, 16.50 mmol) and 2-chloro-4,6-diphenyl-1,3,5-triazine (5.31 g, 18.98 mmol) in 230 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 5 hours. The temperature was lowered to room temperature, the water layer was removed, and the result was dried with anhydrous magnesium sulfate, vacuum concentrated, and then recrystallized with 270 ml of ethyl acetate to prepare Compound 1 (10.36 g, 88%).

MS $[M+H]^+=712$

After completely dissolving Compound B-1 (10.0 g, 16.50 mmol) and 2-chloro-4,6-diphenylpyrimidine (5.31 g, 18.98 mmol) in 250 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 4 hours. The temperature was lowered to room temperature, the water layer was removed, and the result was dried with anhydrous magnesium sulfate, vacuum concentrated, and then recrystallized with 230 ml of ethyl acetate to prepare Compound 2 (9.78 g, 83%).

MS $[M+H]^+=711$

Preparation Example 2

Compound Synthesis of the Following Compound 2

Preparation Example 3

Compound Synthesis of the Following Compound 3

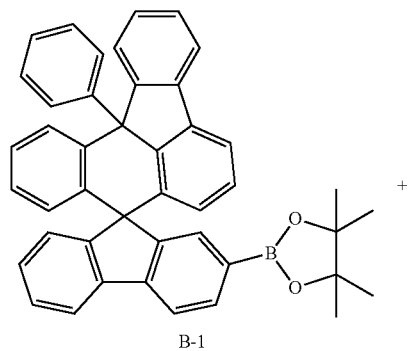

B-1

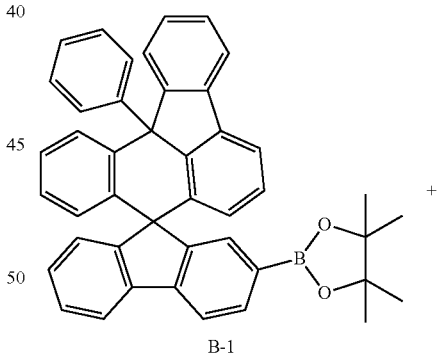

B-1

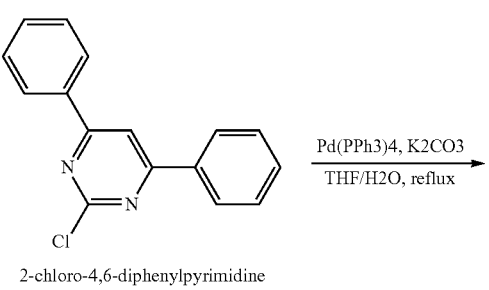

2-chloro-4,6-diphenylpyrimidine

Pd(PPh3)4, K2CO3
THF/H2O, reflux →

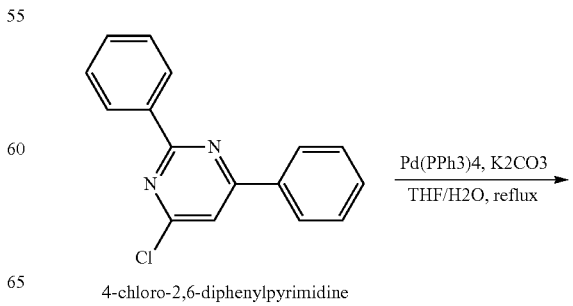

4-chloro-2,6-diphenylpyrimidine

Pd(PPh3)4, K2CO3
THF/H2O, reflux →

-continued

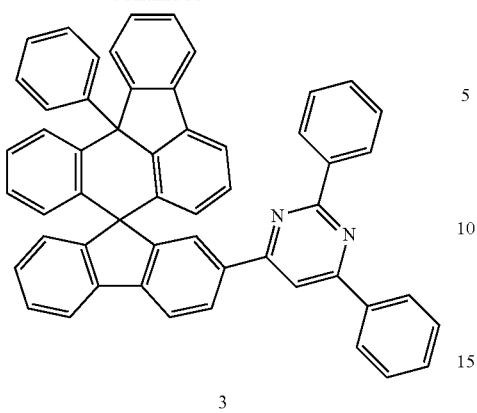

3

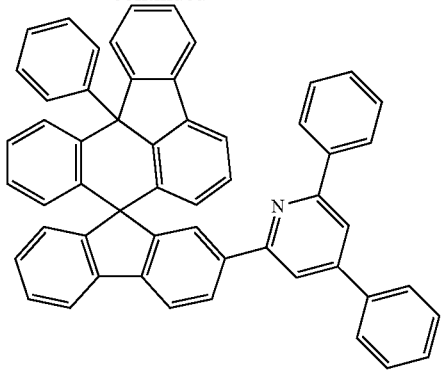

4

After completely dissolving Compound B-1 (10.0 g, 16.50 mmol) and 4-chloro-2,6-diphenylpyrimidine (5.31 g, 18.98 mmol) in 260 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 3 hours. The temperature was lowered to room temperature, the water layer was removed, and the result was dried with anhydrous magnesium sulfate, vacuum concentrated, and then recrystallized with 240 ml of ethyl acetate to prepare Compound 3 (8.65 g, 74%).

MS[M+H]$^+$=711

After completely dissolving Compound B-1 (10.0 g, 16.50 mmol) and 2-chloro-4,6-diphenylpyridine (3.1 g, 18.98 mmol) in 280 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 2 hours. The temperature was lowered to room temperature, the water layer was removed, and the result was dried with anhydrous magnesium sulfate, vacuum concentrated, and then recrystallized with 280 ml of ethyl acetate to prepare Compound 4 (7.74 g, 66%).

MS[M+H]$^+$=710

Preparation Example 4

Compound Synthesis of the Following Compound 4

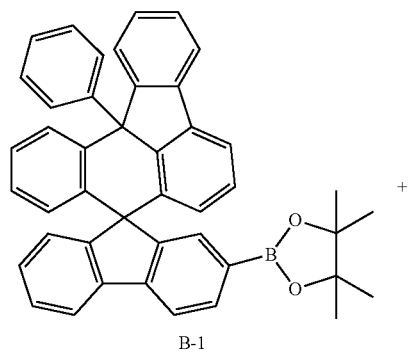

B-1

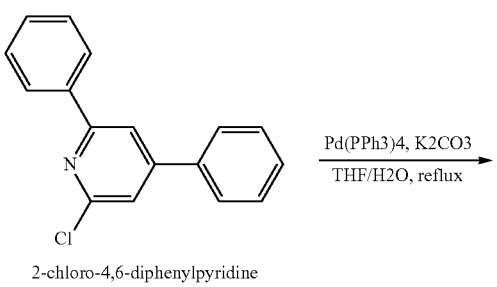

2-chloro-4,6-diphenylpyridine

Pd(PPh3)4, K2CO3
THF/H2O, reflux

Preparation Example 5

Compound Synthesis of the Following Compound 5

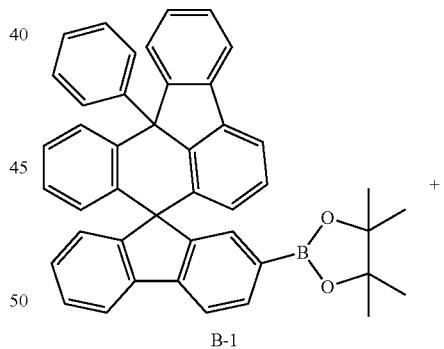

B-1

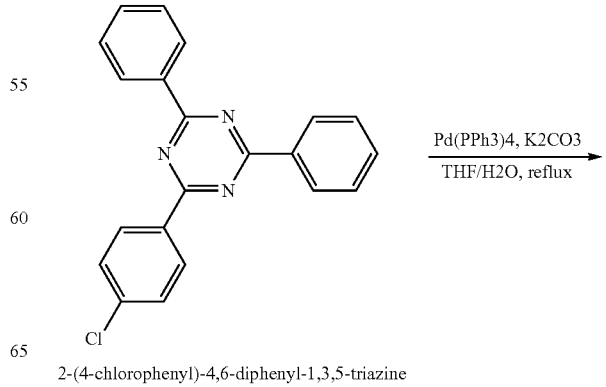

2-(4-chlorophenyl)-4,6-diphenyl-1,3,5-triazine

Pd(PPh3)4, K2CO3
THF/H2O, reflux

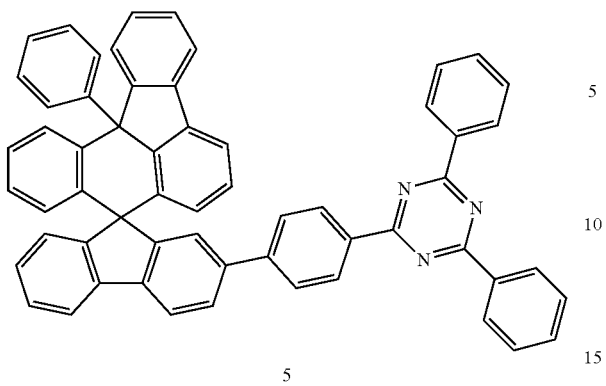

5

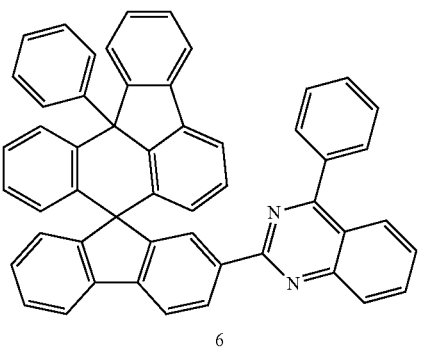

6

After completely dissolving Compound B-1 (10.0 g, 16.50 mmol) and 2-(4-chlorophenyl)-4,6-diphenyl-1,3,5-triazine (6.51 g, 18.98 mmol) in 250 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 5 hours. The temperature was lowered to room temperature, the water layer was removed, and the result was dried with anhydrous magnesium sulfate, vacuum concentrated, and then recrystallized with 300 ml of ethyl acetate to prepare Compound 5 (10.36 g, 88%).

MS[M+H]$^+$=788

Preparation Example 6

Compound Synthesis of the Following Compound 6

After completely dissolving Compound B-1 (10.0 g, 16.50 mmol) and 2-chloro-4-phenylquinazoline (4.57 g, 18.98 mmol) in 250 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 6 hours. The temperature was lowered to room temperature, the water layer was removed, and the result was dried with anhydrous magnesium sulfate, vacuum concentrated, and then recrystallized with 230 ml of ethyl acetate to prepare Compound 6 (9.95 g, 74%).

MS[M+H]$^+$=685

Preparation Example 7

Compound Synthesis of the Following Compound 7

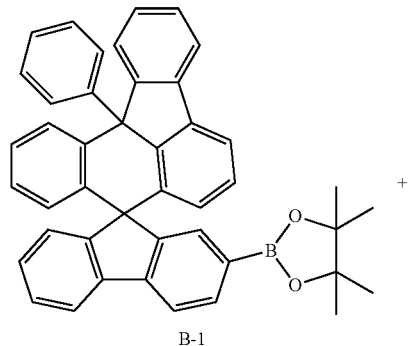

B-1

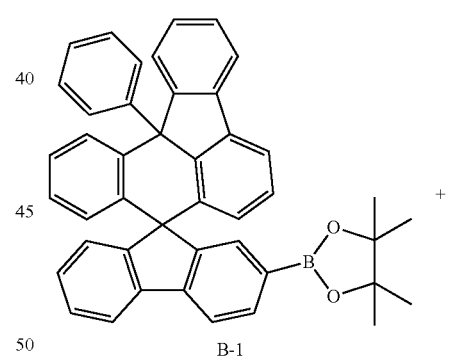

B-1

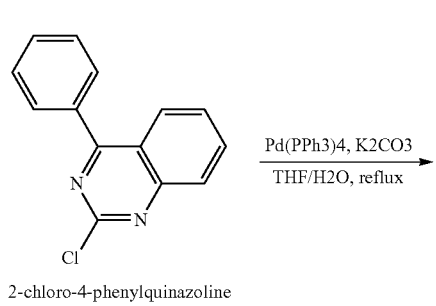

2-chloro-4-phenylquinazoline

Pd(PPh3)4, K2CO3
THF/H2O, reflux

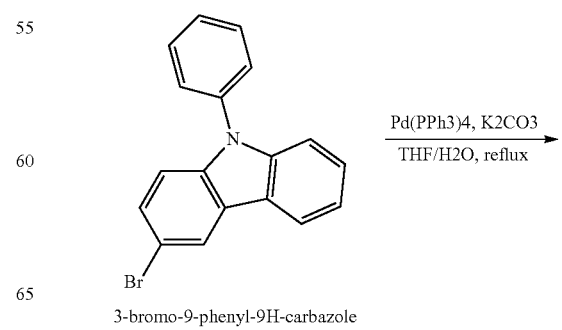

3-bromo-9-phenyl-9H-carbazole

Pd(PPh3)4, K2CO3
THF/H2O, reflux

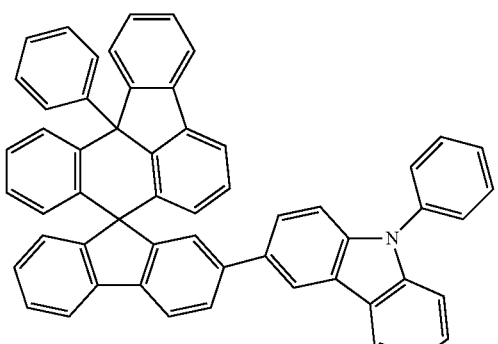

7

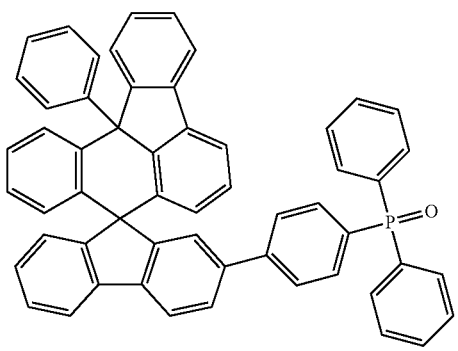

8

After completely dissolving Compound B-1 (10.0 g, 16.50 mmol) and 3-bromo-9-phenyl-9H-carbazole (6.09 g, 18.98 mmol) in 250 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 6 hours. The temperature was lowered to room temperature, the water layer was removed, and the result was dried with anhydrous magnesium sulfate, vacuum concentrated, and then recrystallized with 230 ml of ethyl acetate to prepare Compound 7 (12.05 g, 85%).

MS[M+H]$^+$=722

After completely dissolving Compound B-1 (10.0 g, 16.50 mmol) and (4-bromophenyl)diphenylphosphine oxide (7.71 g, 18.98 mmol) in 250 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 4 hours. The temperature was lowered to room temperature, the water layer was removed, and the result was dried with anhydrous magnesium sulfate, vacuum concentrated, and then recrystallized with 310 ml of ethyl acetate to prepare Compound 8 (13.97 g, 94%).

MS[M+H]$^+$=757

Preparation Example 8

Compound Synthesis of the Following Compound 8

Preparation Example 9

Compound Synthesis of the Following Compound 9

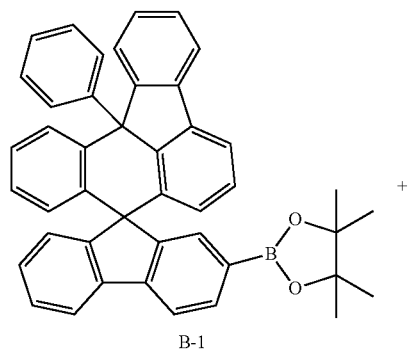

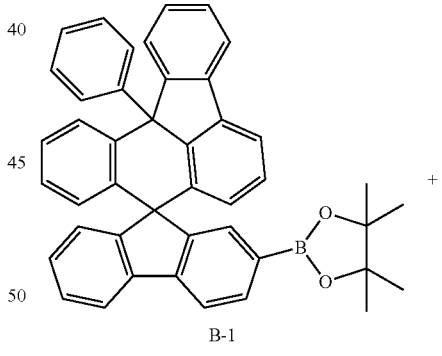

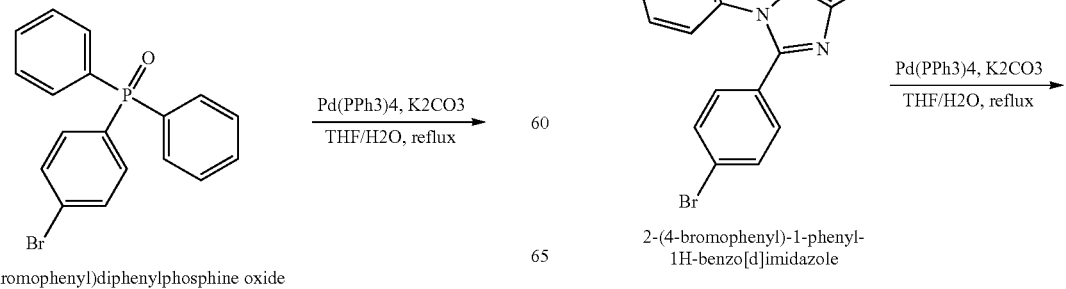

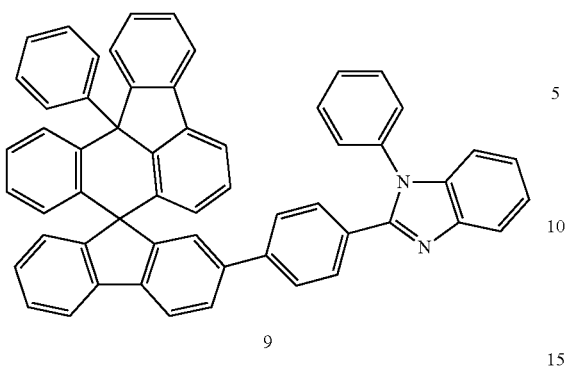

9

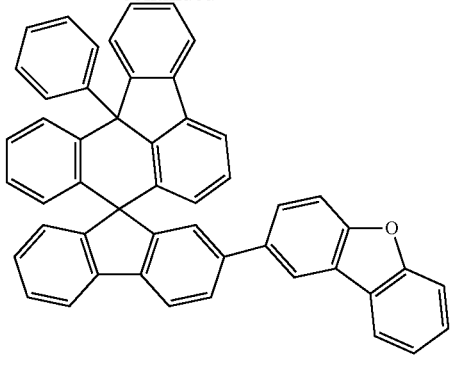

10

After completely dissolving Compound B-1 (10.0 g, 16.50 mmol) and 2-(4-bromophenyl)-1-phenyl-1H-benzo[d]imidazole (7.71 g, 18.98 mmol) in 250 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 4 hours. The temperature was lowered to room temperature, the water layer was removed, and the result was dried with anhydrous magnesium sulfate, vacuum concentrated, and then recrystallized with 310 ml of ethyl acetate to prepare Compound 9 (12.24 g, 83%).

MS[M+H]$^+$=749

Preparation Example 10

Compound Synthesis of the Following Compound 10

After completely dissolving Compound B-1 (10.0 g, 16.50 mmol) and 2-bromodibenzo[b,d]furan (4.69 g, 18.98 mmol) in 290 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 3 hours. The temperature was lowered to room temperature, the water layer was removed, and the result was dried with anhydrous magnesium sulfate, vacuum concentrated, and then recrystallized with 230 ml of ethyl acetate to prepare Compound 10 (7.53 g, 59%).

MS[M+H]$^+$=647

Preparation Example 11

Compound Synthesis of the Following Compound 11

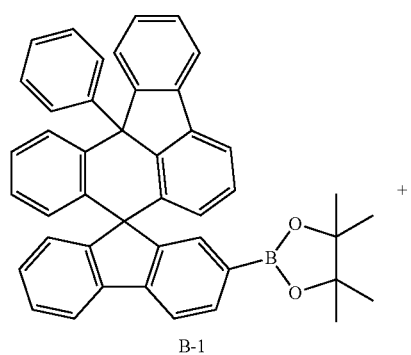

B-1

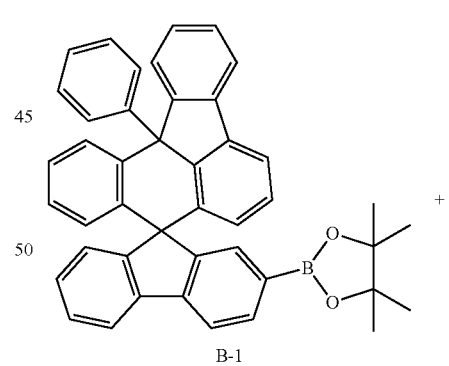

B-1

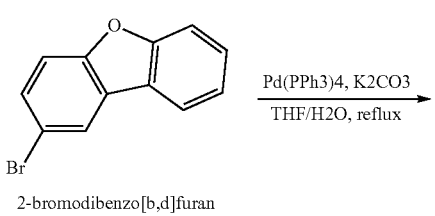

2-bromodibenzo[b,d]furan

Pd(PPh3)4, K2CO3
THF/H2O, reflux →

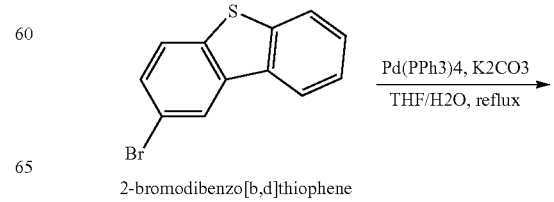

2-bromodibenzo[b,d]thiophene

Pd(PPh3)4, K2CO3
THF/H2O, reflux →

11

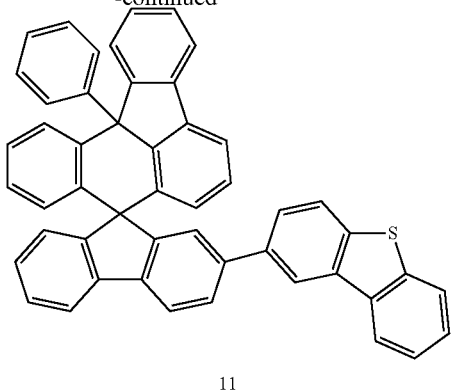

After completely dissolving Compound B-1 (10.0 g, 16.50 mmol) and 2-bromodibenzo[b,d]thiophene (4.99 g, 18.98 mmol) in 290 ml of tetrahydrofuran in a 500 ml round bottom flask under nitrogen atmosphere, an aqueous 2 M potassium carbonate solution (125 ml) and then tetrakis-(triphenylphosphine)palladium (0.19 g, 0.17 mmol) were added thereto, and the result was heated and stirred for 3 hours. The temperature was lowered to room temperature, the water layer was removed, and the result was dried with anhydrous magnesium sulfate, vacuum concentrated, and then recrystallized with 230 ml of ethyl acetate to prepare Compound 11 (7.53 g, 59%).

MS[M+H]$^+$=663

<Preparation Example 12> to <Preparation Example 22>

12

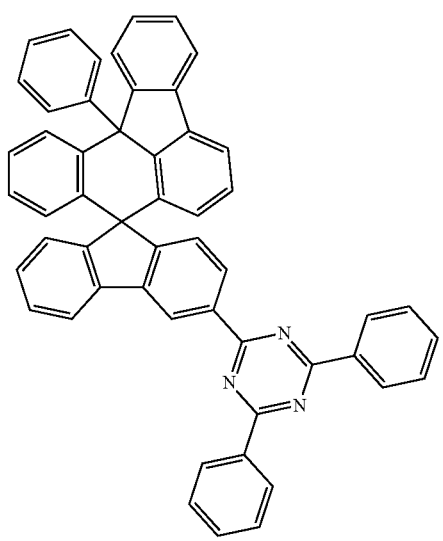

13

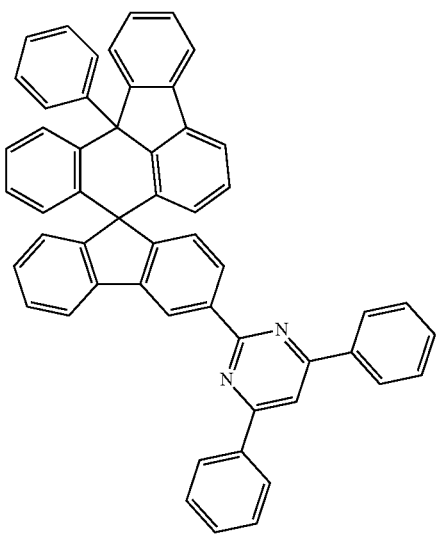

14

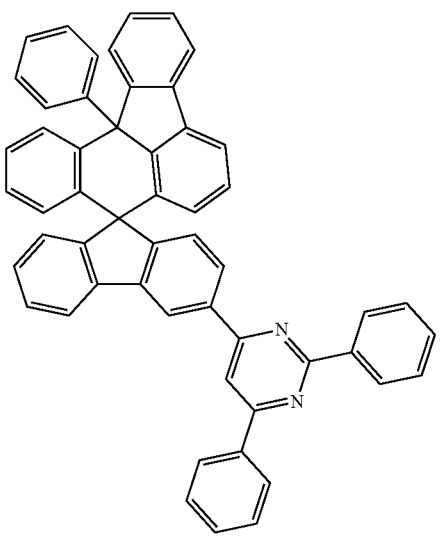

15

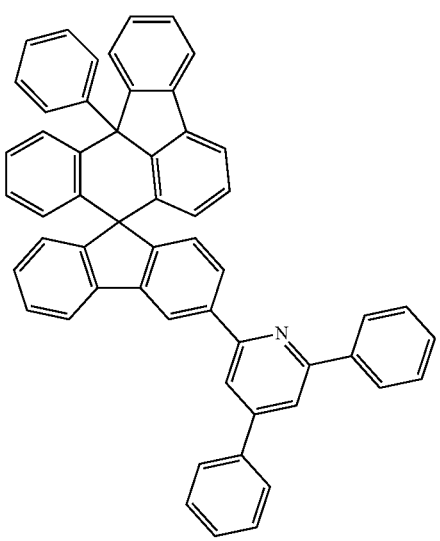

16
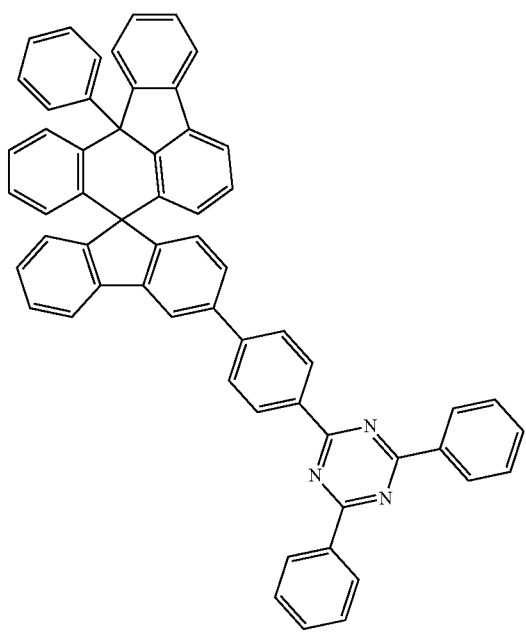
17
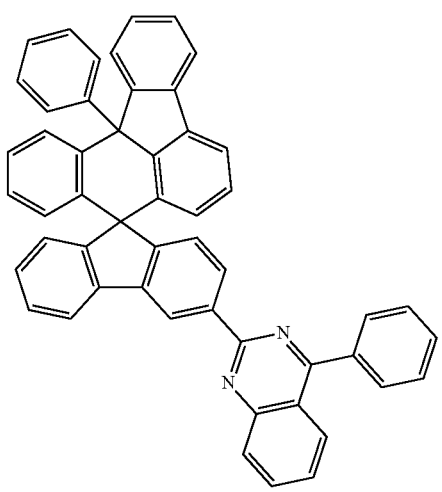
18
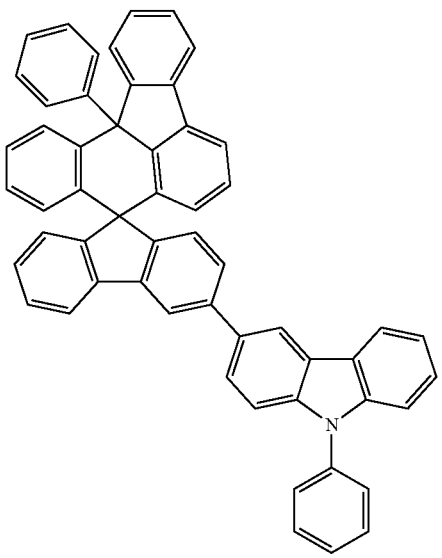
19
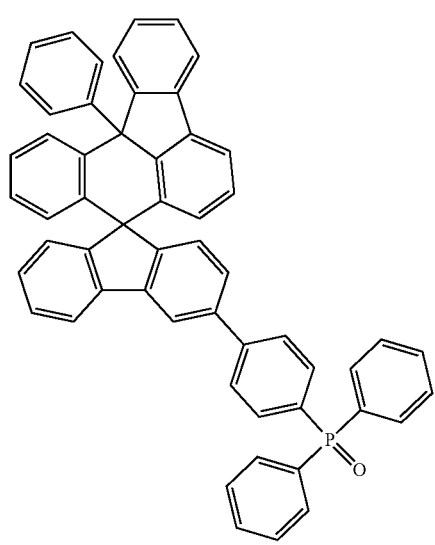
20
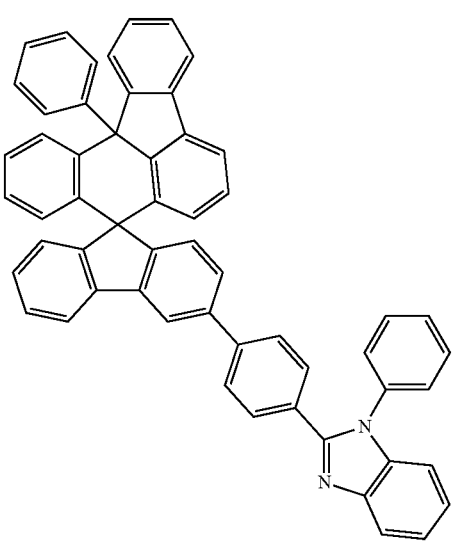

-continued
21
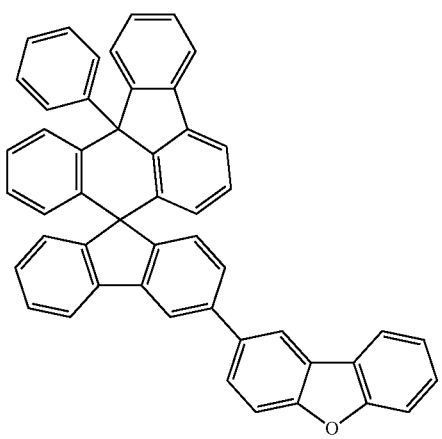
22
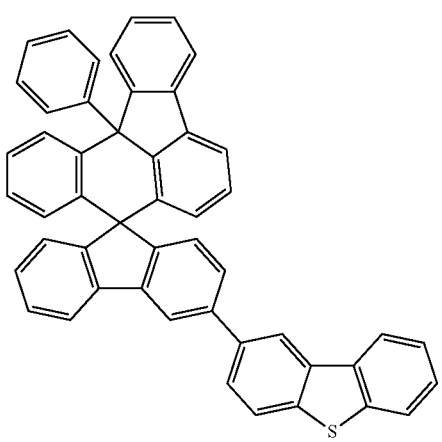
Compounds 12, 13, 14, 15, 16, 17, 18, 19, 20, 21 and 22 were prepared in the same manner as in Preparation Examples 1 to 11 except that Compound C-1 was used as the staring material instead of Compound B-1.
TABLE 1
| Compound | MS [M + H]$^+$ |
|---|---|
| 12 | 712 |
| 13 | 711 |
| 14 | 711 |
| 15 | 710 |
| 16 | 788 |
| 17 | 685 |
| 18 | 722 |
| 19 | 757 |
| 20 | 749 |
| 21 | 647 |
| 22 | 663 |
<Preparation Example 23> to <Preparation Example 33>
23
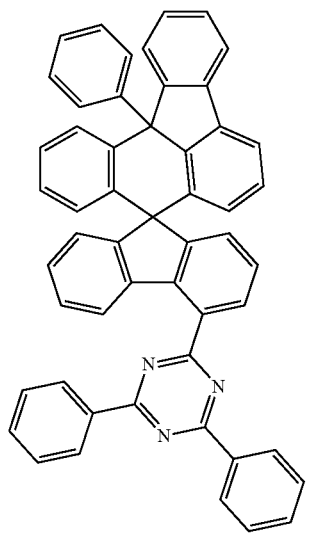
24
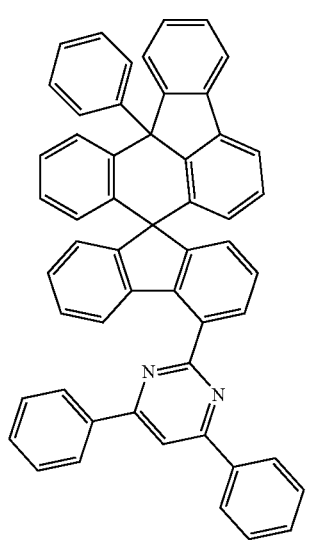
25
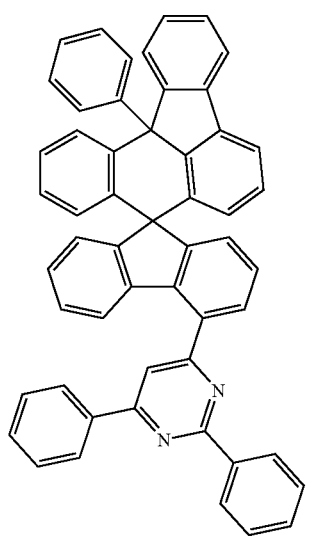

26
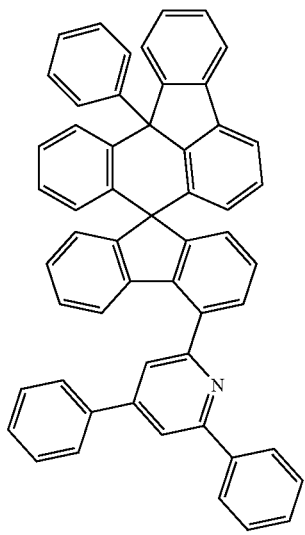
27
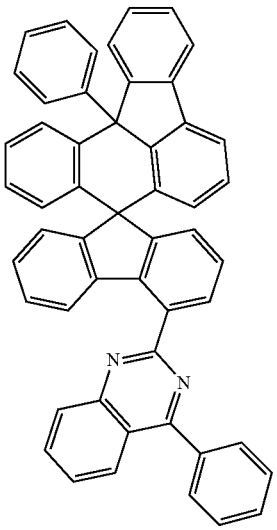
28
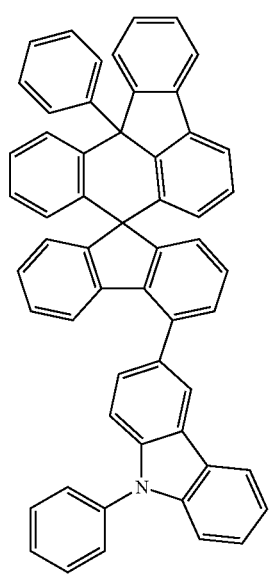
29
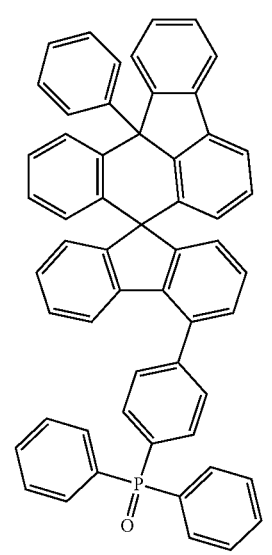
30

31 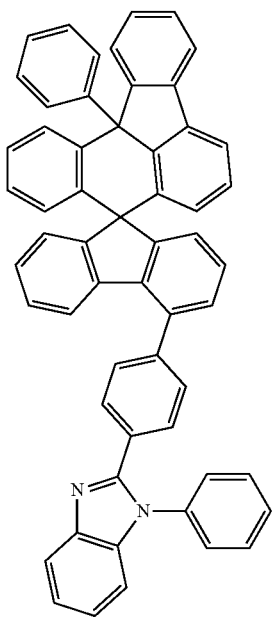
33 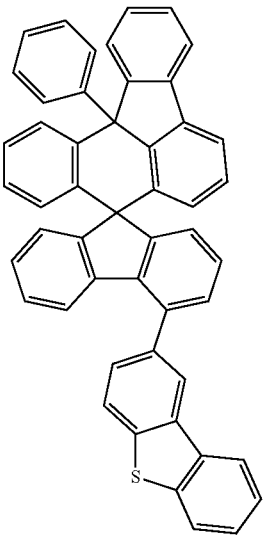
Compounds 23, 24, 25, 26, 27, 28, 29, 30, 31, 32 and 33 were prepared in the same manner as in Preparation Examples 1 to 11 except that Compound D-1 was used as the staring material instead of Compound B-1.
TABLE 2
| Compound | MS [M + H]+ |
|---|---|
| 23 | 712 |
| 24 | 711 |
| 25 | 711 |
| 26 | 710 |
| 27 | 788 |
| 28 | 685 |
| 29 | 722 |
| 30 | 757 |
| 31 | 749 |
| 32 | 647 |
| 33 | 663 |
<Preparation Example 34> to <Preparation Example 44>
32 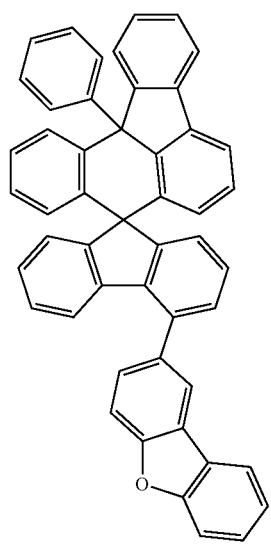
34 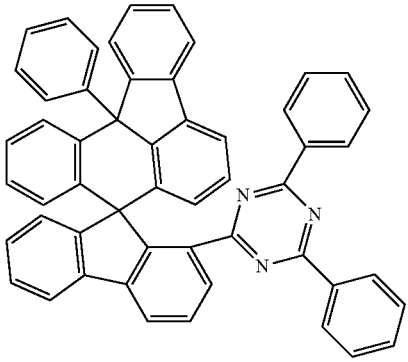

117
-continued
35
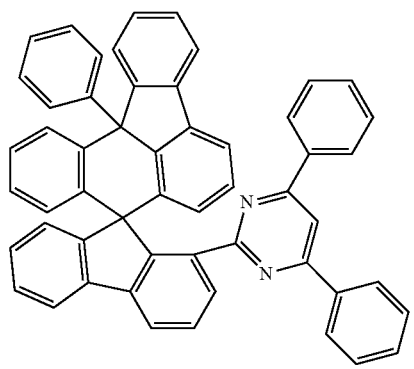
36
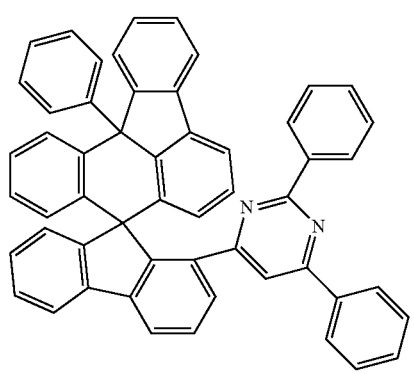
37
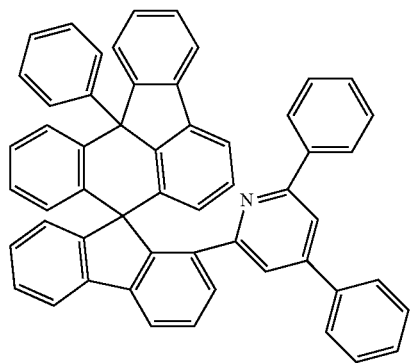
38
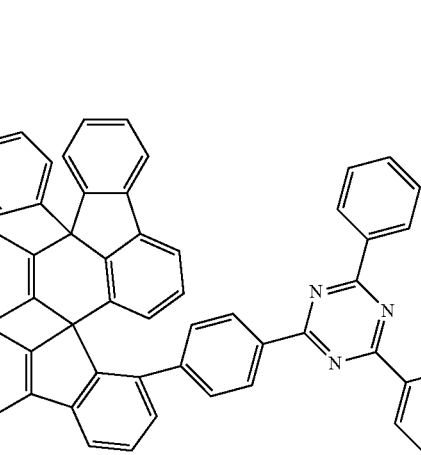
118
-continued
39
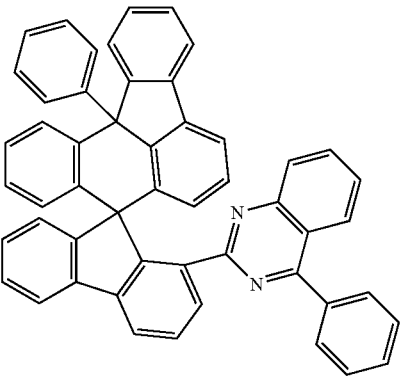
40
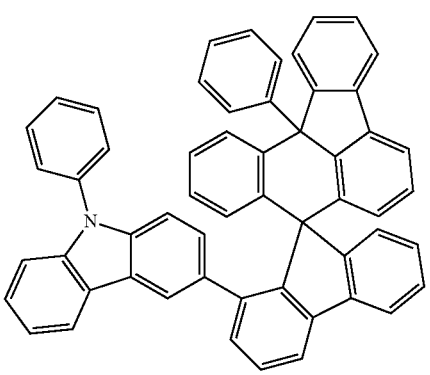
41
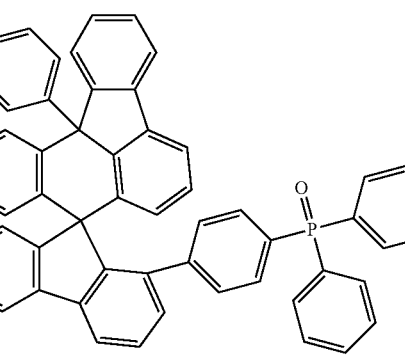
42
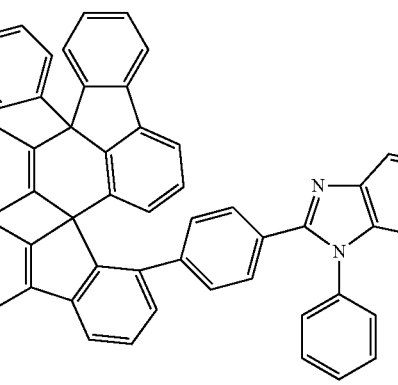

-continued

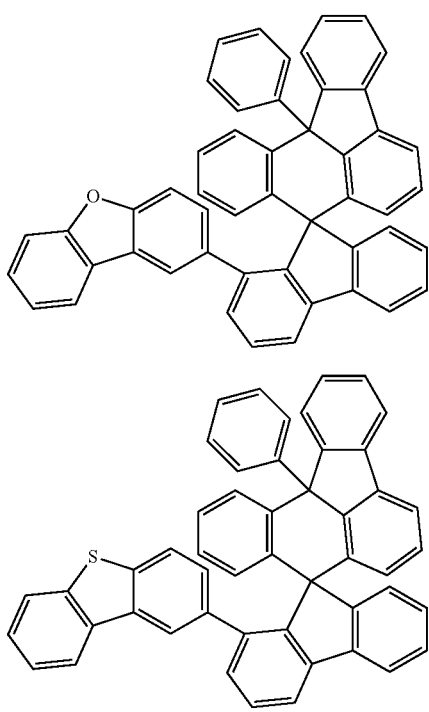

43

44

Compounds 34, 35, 36, 37, 38, 39, 40, 41, 42, 43 and 44 were prepared in the same manner as in Preparation Examples 1 to 11 except that Compound A-1 was used as the staring material instead of Compound B-1.

TABLE 3

| Compound | MS [M + H]+ |
|---|---|
| 34 | 712 |
| 35 | 711 |
| 36 | 711 |
| 37 | 710 |
| 38 | 788 |
| 39 | 685 |
| 40 | 722 |
| 41 | 757 |
| 42 | 749 |
| 43 | 647 |
| 44 | 663 |

Example 1

The compounds synthesized in the synthesis examples were high-purity sublimation purified using commonly known methods, and then a green organic light emitting device was manufactured using a method as below.

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic light emitting device was manufactured by forming a light emitting element in the order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) on the transparent ITO electrode prepared as above using CBP as a host.

Structures of the m-MTDATA, the TCTA, the Ir(ppy)$_3$, the CBP and the BCP are as follows.

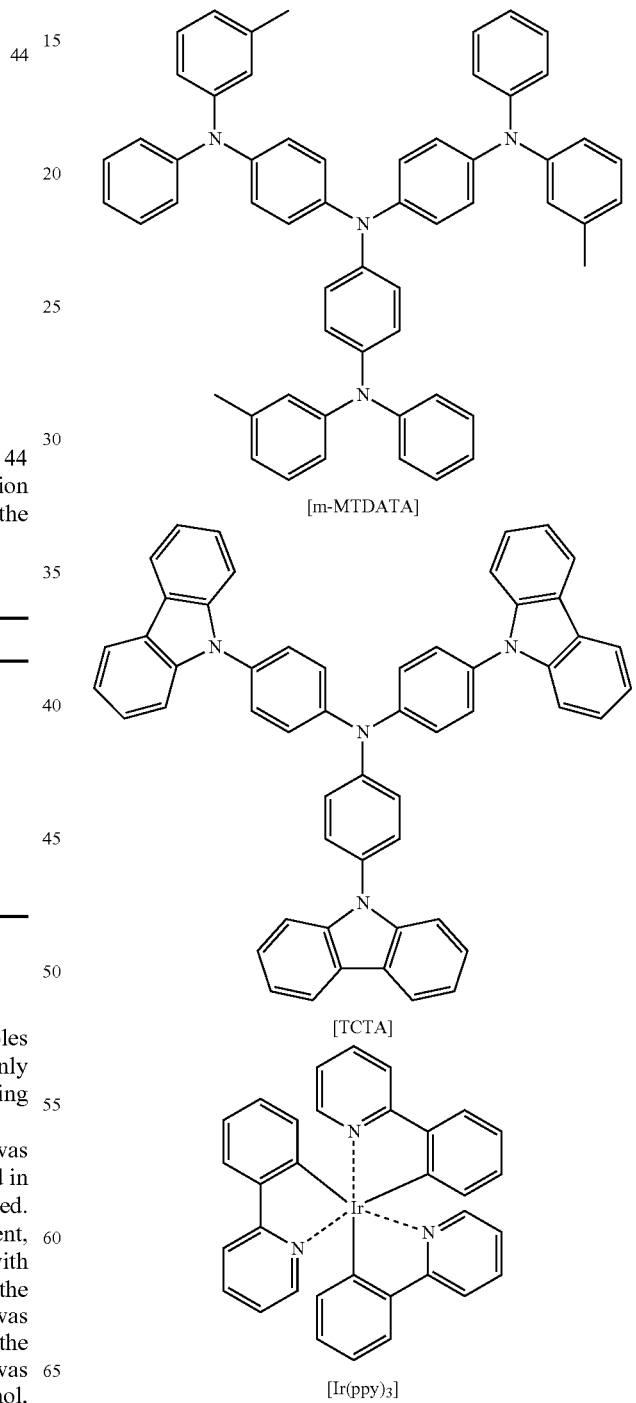

[m-MTDATA]

[TCTA]

[Ir(ppy)$_3$]

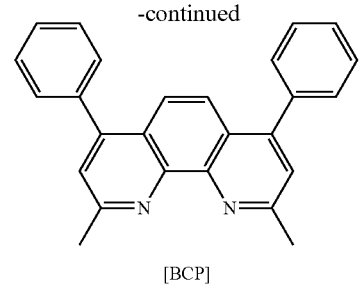

[BCP]

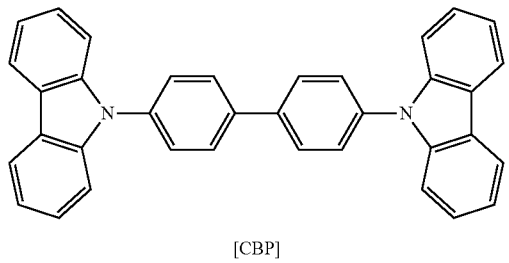

[CBP]

Example 1-1

An organic light emitting device was manufactured in the same manner as in Example 1 except that Compound 1 was used instead of CBP.

Example 1-2

An organic light emitting device was manufactured in the same manner as in Example 1 except that Compound 2 was used instead of CBP.

Example 1-3

An organic light emitting device was manufactured in the same manner as in Example 1 except that Compound 3 was used instead of CBP.

Example 1-4

An organic light emitting device was manufactured in the same manner as in Example 1 except that Compound 4 was used instead of CBP.

Example 1-5

An organic light emitting device was manufactured in the same manner as in Example 1 except that Compound 5 was used instead of CBP.

Example 1-6

An organic light emitting device was manufactured in the same manner as in Example 1 except that Compound 12 was used instead of CBP.

Example 1-7

An organic light emitting device was manufactured in the same manner as in Example 1 except that Compound 13 was used instead of CBP.

Example 1-8

An organic light emitting device was manufactured in the same manner as in Example 1 except that Compound 14 was used instead of CBP.

Example 1-9

An organic light emitting device was manufactured in the same manner as in Example 1 except that Compound 15 was used instead of CBP.

Example 1-10

An organic light emitting device was manufactured in the same manner as in Example 1 except that Compound 16 was used instead of CBP.

Example 1-11

An organic light emitting device was manufactured in the same manner as in Example 1 except that Compound 23 was used instead of CBP.

Example 1-12

An organic light emitting device was manufactured in the same manner as in Example 1 except that Compound 24 was used instead of CBP.

Example 1-13

An organic light emitting device was manufactured in the same manner as in Example 1 except that Compound 25 was used instead of CBP.

Example 1-14

An organic light emitting device was manufactured in the same manner as in Example 1 except that Compound 26 was used instead of CBP.

Example 1-15

An organic light emitting device was manufactured in the same manner as in Example 1 except that Compound 27 was used instead of CBP.

Example 1-16

An organic light emitting device was manufactured in the same manner as in Example 1 except that Compound 34 was used instead of CBP.

Example 1-17

An organic light emitting device was manufactured in the same manner as in Example 1 except that Compound 35 was used instead of CBP.

Example 1-18

An organic light emitting device was manufactured in the same manner as in Example 1 except that Compound 36 was used instead of CBP.

Example 1-19

An organic light emitting device was manufactured in the same manner as in Example 1 except that Compound 37 was used instead of CBP.

Example 1-20

An organic light emitting device was manufactured in the same manner as in Example 1 except that Compound 38 was used instead of CBP.

When a current was applied to the organic light emitting devices manufactured in Example 1, and Examples 1-1 to 1-20, results of Table 4 were obtained.

TABLE 4

| | Compound (Host) | Voltage (V@10 mA/cm$^2$) | Efficiency (cd/A@10 mA/cm$^2$) | EL Peak (nm) |
|---|---|---|---|---|
| Example 1 | CBP | 7.45 | 38.12 | 516 |
| Example 1-1 | Compound 1 | 6.30 | 43.53 | 517 |
| Example 1-2 | Compound 2 | 6.32 | 43.14 | 517 |
| Example 1-3 | Compound 3 | 6.31 | 43.32 | 517 |
| Example 1-4 | Compound 4 | 6.22 | 44.45 | 518 |
| Example 1-5 | Compound 5 | 6.30 | 43.31 | 517 |
| Example 1-6 | Compound 12 | 6.23 | 44.63 | 517 |
| Example 1-7 | Compound 13 | 6.31 | 43.02 | 516 |
| Example 1-8 | Compound 14 | 6.32 | 43.24 | 513 |
| Example 1-9 | Compound 15 | 6.22 | 44.38 | 516 |
| Example 1-10 | Compound 16 | 6.31 | 43.82 | 516 |
| Example 1-11 | Compound 23 | 6.32 | 43.50 | 517 |
| Example 1-12 | Compound 24 | 6.31 | 43.16 | 516 |
| Example 1-13 | Compound 25 | 6.32 | 43.23 | 516 |
| Example 1-14 | Compound 26 | 6.26 | 44.44 | 516 |
| Example 1-15 | Compound 27 | 6.31 | 43.62 | 516 |
| Example 1-16 | Compound 34 | 6.29 | 44.75 | 516 |
| Example 1-17 | Compound 35 | 6.38 | 43.91 | 516 |
| Example 1-18 | Compound 36 | 6.23 | 44.83 | 517 |
| Example 1-19 | Compound 37 | 6.24 | 44.42 | 516 |
| Example 1-20 | Compound 38 | 6.27 | 44.54 | 517 |

From the test results, it was identified that the green organic light emitting devices of Examples 1-1 to 1-20 using the compounds according to the present disclosure as a host material of the light emitting layer exhibited superior performance in terms of current efficiency and driving voltage compared to the green organic light emitting device of Example 1 using existing CBP. Particularly, it was seen that the compounds having triazine, pyrimidine or pyridine as a substituent were suitable for a green organic light emitting device.

Example 2

The compounds synthesized in the preparation examples were high-purity sublimation purified using commonly known methods, and then a red organic light emitting device was manufactured using a method as below.

An ITO glass was patterned so that a light emitting area became a 2 mm×2 mm size, and then cleaned. After installing the substrate in a vacuum chamber, the base pressure was set at 1×10$^6$ torr, and as organic materials on the ITO, a DNTPD layer (700 Å) and an α-NPB layer (300 Å) were formed, and a light emitting layer was prepared by using CBP as a host (90 wt %) and vacuum depositing (300 Å) the following (piq)$_2$Ir(acac) (10 wt %) as a dopant. Subsequently, an Alq$_3$ layer (350 Å), a LiF layer (5 Å) and an Al layer (1,000 Å) were formed in this order, and properties of the device were measured at 0.4 mA.

Structures of the DNTPD, the α-NPB, the (piq)$_2$Ir(acac) and the Alq$_3$ are as follows.

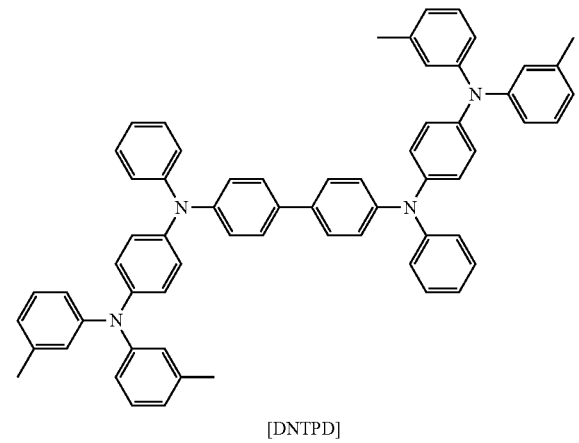

[DNTPD]

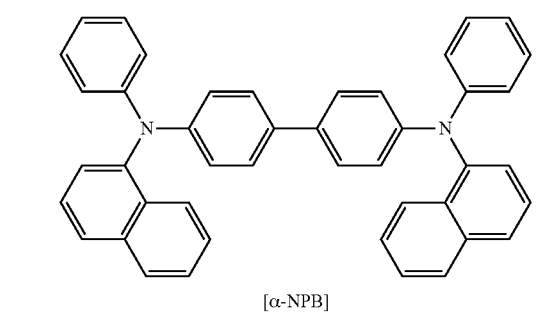

[α-NPB]

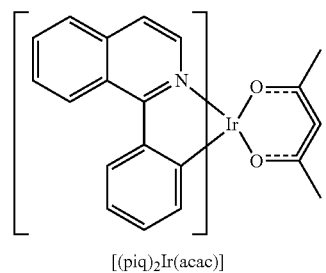

[(piq)$_2$Ir(acac)]

-continued

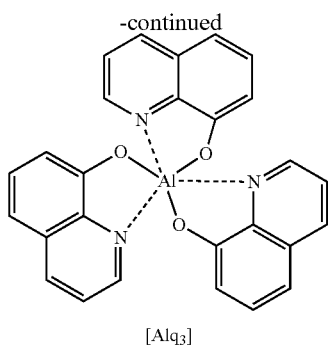

[Alq₃]

<Example 2-1> to <Example 2-4>

Organic light emitting devices were manufactured in the same manner as in Example 2 except that Compounds 7, 18, 29 and 40 prepared in the preparation examples described above were respectively used instead of CBP.

For the organic light emitting devices manufactured according to Examples 2-1 to 2-4, and Example 2, a voltage, current density, luminance, a color coordinate and a lifespan were measured, and the results are shown in the following Table 5. T95 means time taken for the luminance decreasing to 95% of its initial luminance (5000 nit).

TABLE 5

| Category | Compound (Host) | Dopant | Voltage | Luminance (V) | CIEx (cd/m²) | CIEy (cd/m²) | T95 (hr) |
|---|---|---|---|---|---|---|---|
| Example 2-1 | Compound 7 | [(piq)₂Ir(acac)] | 4.3 | 1760 | 0.670 | 0.329 | 465 |
| Example 2-2 | Compound 18 | [(piq)₂Ir(acac)] | 4.2 | 1850 | 0.674 | 0.325 | 415 |
| Example 2-3 | Compound 29 | [(piq)₂Ir(acac)] | 4.1 | 1900 | 0.672 | 0.327 | 390 |
| Example 2-4 | Compound 40 | [(piq)₂Ir(acac)] | 4.3 | 1740 | 0.673 | 0.335 | 475 |
| Example 2 | CBP | [(piq)₂Ir(acac)] | 7.5 | 1220 | 0.679 | 0.339 | 285 |

From the test results, it was identified that the red organic light emitting devices of Examples 2-1 to 2-4 using the compounds represented by Compounds 7, 18, 29 and 40 prepared according to the present disclosure as a host material of the light emitting layer exhibited superior performance in terms of current efficiency, driving voltage and lifespan compared to the red organic light emitting device of Example 2 using existing CBP. Particularly, it was seen that the compounds having carbazole as a substituent were suitable for a red organic light emitting device.

Example 3-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

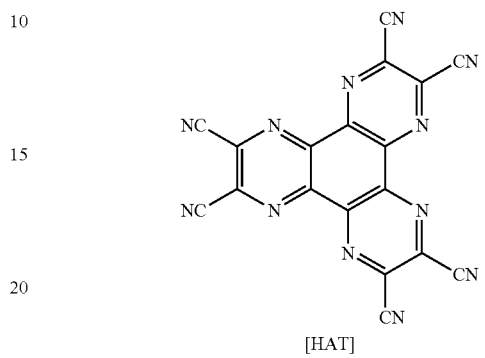

[HAT]

A hole transfer layer was formed on the hole injection layer by vacuum depositing the following compound 4-4'-bis[N-(1-naphthyl)-N-phenylamino]biphenyl (NPB) (400 Å), a material transferring holes.

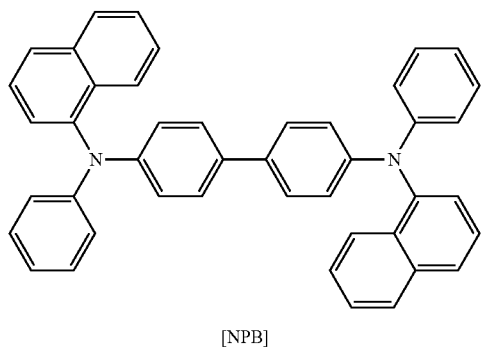

[NPB]

Subsequently, a light emitting layer was formed on the hole transfer layer to a film thickness of 300 Å by vacuum depositing BH and BD shown below in a weight ratio of 25:1.

[BH]

[BD]

[LiQ]

An electron injection and transfer layer was formed on the light emitting layer to a thickness of 300 Å by vacuum depositing the Compound 1 prepared in Preparation Example 1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^7$ torr to $5 \times 10$ torr.

Example 3-2

An experiment was carried out in the same manner as in Example 3-1 except that Compound 5 was used instead of Compound 1 as the electron transfer layer.

Example 3-3

An experiment was carried out in the same manner as in Example 3-1 except that Compound 8 was used instead of Compound 1 as the electron transfer layer.

Example 3-4

An experiment was carried out in the same manner as in Example 3-1 except that Compound 9 was used instead of Compound 1 as the electron transfer layer.

Example 3-5

An experiment was carried out in the same manner as in Example 3-1 except that Compound 12 was used instead of Compound 1 as the electron transfer layer.

Example 3-6

An experiment was carried out in the same manner as in Example 3-1 except that Compound 16 was used instead of Compound 1 as the electron transfer layer.

Example 3-7

An experiment was carried out in the same manner as in Example 3-1 except that Compound 19 was used instead of Compound 1 as the electron transfer layer.

Example 3-8

An experiment was carried out in the same manner as in Example 3-1 except that Compound 20 was used instead of Compound 1 as the electron transfer layer.

Example 3-9

An experiment was carried out in the same manner as in Example 3-1 except that Compound 23 was used instead of Compound 1 as the electron transfer layer.

Example 3-10

An experiment was carried out in the same manner as in Example 3-1 except that Compound 27 was used instead of Compound 1 as the electron transfer layer.

Example 3-11

An experiment was carried out in the same manner as in Example 3-1 except that Compound 30 was used instead of Compound 1 as the electron transfer layer.

Example 3-12

An experiment was carried out in the same manner as in Example 3-1 except that Compound 31 was used instead of Compound 1 as the electron transfer layer.

Example 3-13

An experiment was carried out in the same manner as in Example 3-1 except that Compound 34 was used instead of Compound 1 as the electron transfer layer.

Example 3-14

An experiment was carried out in the same manner as in Example 3-1 except that Compound 38 was used instead of Compound 1 as the electron transfer layer.

Example 3-15

An experiment was carried out in the same manner as in Example 3-1 except that Compound 41 was used instead of Compound 1 as the electron transfer layer.

Example 3-16

An experiment was carried out in the same manner as in Example 3-1 except that Compound 42 was used instead of Compound 1 as the electron transfer layer.

Example 3

An experiment was carried out in the same manner as in Example 3-1 except that the following Compound ET 1 was used instead of Compound 1 as the electron transfer layer.

[ET 1]

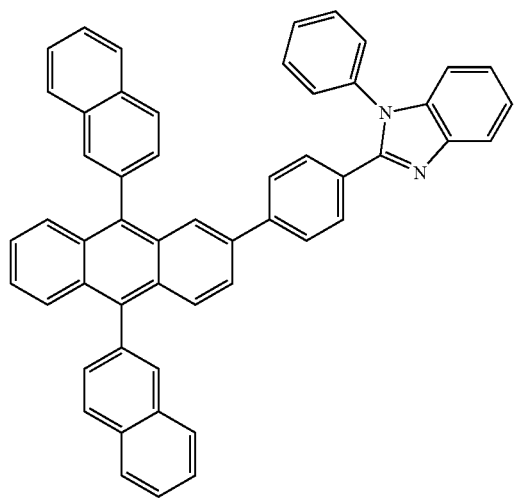

When a current was applied to the organic light emitting devices manufactured in Examples 3-1 to 3-16, and Example 3, results of Table 6 were obtained.

TABLE 6

| Category | Compound (Electron Transfer Layer) | Voltage (V@10 mA/cm$^2$) | Efficiency (cd/A@10 mA/cm$^2$) | EL Peak (nm) |
|---|---|---|---|---|
| Example 3-1 | Compound 1 | 6.28 | 46.93 | 517 |
| Example 3-2 | Compound 5 | 6.36 | 45.24 | 516 |
| Example 3-3 | Compound 8 | 6.35 | 45.79 | 518 |
| Example 3-4 | Compound 9 | 6.29 | 46.15 | 517 |
| Example 3-5 | Compound 12 | 6.38 | 45.31 | 515 |
| Example 3-6 | Compound 16 | 6.33 | 45.63 | 516 |
| Example 3-7 | Compound 19 | 6.39 | 45.62 | 516 |
| Example 3-8 | Compound 20 | 6.37 | 45.64 | 517 |
| Example 3-9 | Compound 23 | 6.24 | 46.68 | 518 |
| Example 3-10 | Compound 27 | 6.38 | 45.83 | 517 |
| Example 3-11 | Compound 30 | 6.36 | 45.24 | 516 |
| Example 3-12 | Compound 31 | 6.44 | 44.94 | 518 |
| Example 3-13 | Compound 34 | 6.35 | 45.22 | 517 |
| Example 3-14 | Compound 38 | 6.33 | 45.75 | 515 |
| Example 3-15 | Compound 41 | 6.15 | 47.16 | 516 |
| Example 3-16 | Compound 42 | 6.24 | 46.34 | 516 |
| Example 3 | ET 1 | 7.45 | 35.52 | 517 |

As seen from Table 6, it was identified that electron transfer and injection abilities were excellent when comparing Examples 3-1 to 3-16, and Example 3. Particularly, it was seen that the compounds having triazine, benzimidazole or arylphosphine oxide as a substituent were suitable as a material of the organic light emitting device.

Hereinbefore, preferred embodiments of the present disclosure (green light emitting layer, red light emitting layer, electron transfer layer) have been described, however, the present disclosure is not limited thereto, and various modifications may be made within the scope of the claims and the detailed descriptions, and the modifications are also included in the scope of the present disclosure.

The invention claimed is:
1. A compound represented by the following Chemical Formula 1:

[Chemical Formula 1]

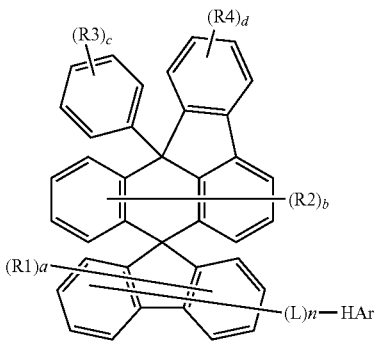

wherein, in Chemical Formula 1,

L is a direct bond; a substituted or unsubstituted arylene group; or a substituted or unsubstituted heteroarylene group, HAr is a substituted or unsubstituted heterocyclic group; or a substituted or unsubstituted phosphine oxide group, R1 to R4 are the same as or different from each other, and each independently hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to an adjacent group to form a substituted or unsubstituted ring, a is an integer of 0 to 7, b is an integer of 0 to 7, c is an integer of 0 to 5, d is an integer of 0 to 4, n is an integer of 0 to 10, and when a, b, c, d and n are each 2 or greater, structures in the parentheses are the same as or different from each other.

2. The compound of claim 1, wherein Chemical Formula 1 is represented by one of the following Chemical Formulae 2 to 5:

[Chemical Formula 2]

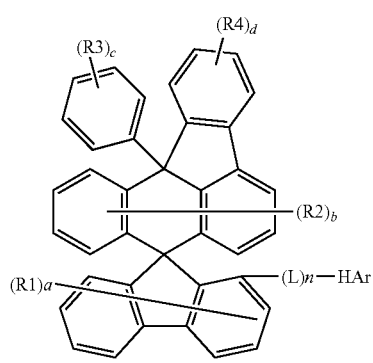

[Chemical Formula 3]

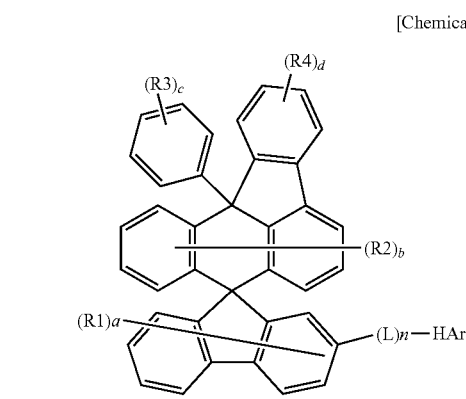

[Chemical Formula 4]

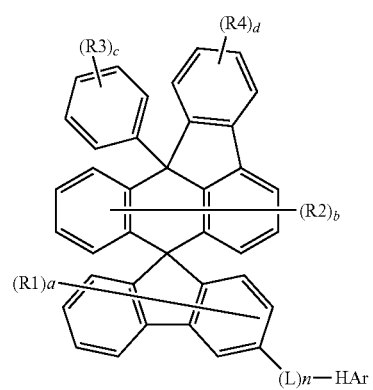

[Chemical Formula 5]

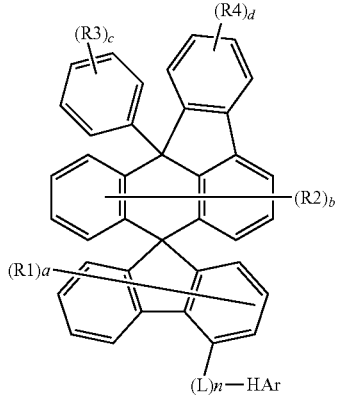

wherein, in Chemical Formulae 2 to 5, definitions of substituents are the same as in Chemical Formula 1.

3. The compound of claim 1, wherein HAr is a substituted or unsubstituted pyridyl group; a substituted or unsubstituted pyrimidyl group; a substituted or unsubstituted triazinyl group; a substituted or unsubstituted furan group; a substituted or unsubstituted thiophene group; a substituted or unsubstituted oxadiazole group; a substituted or unsubstituted thiadiazole group; a substituted or unsubstituted phenanthroline group; a substituted or unsubstituted quinolinyl group; a substituted or unsubstituted isoquinolinyl group; a substituted or unsubstituted quinazoline group; a substituted or unsubstituted benzoxazole group; a substituted or unsubstituted benzothiazole group; a substituted or unsubstituted benzimidazole group; a substituted or unsubstituted phenoxazine group; a substituted or unsubstituted phenothiazine group; a substituted or unsubstituted dibenzofuran group; a substituted or unsubstituted dibenzothiophene group; a substituted or unsubstituted carbazole group; or a substituted or unsubstituted diarylphosphine oxide group.

4. The compound of claim 1, wherein -(L)n-HAr is represented by the following structural formulae:

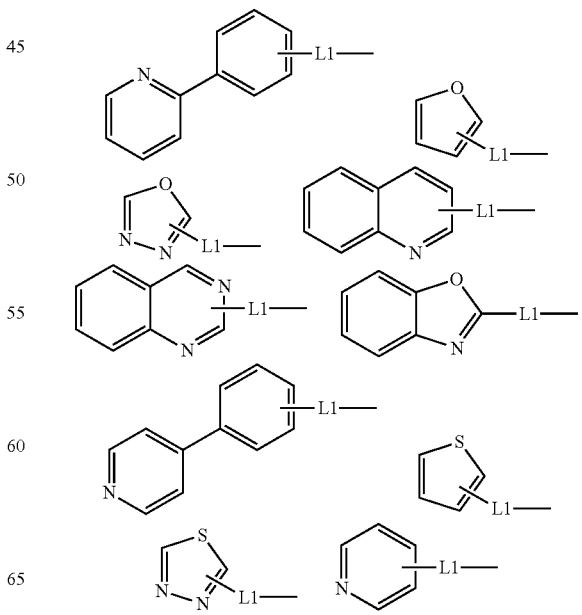

-continued

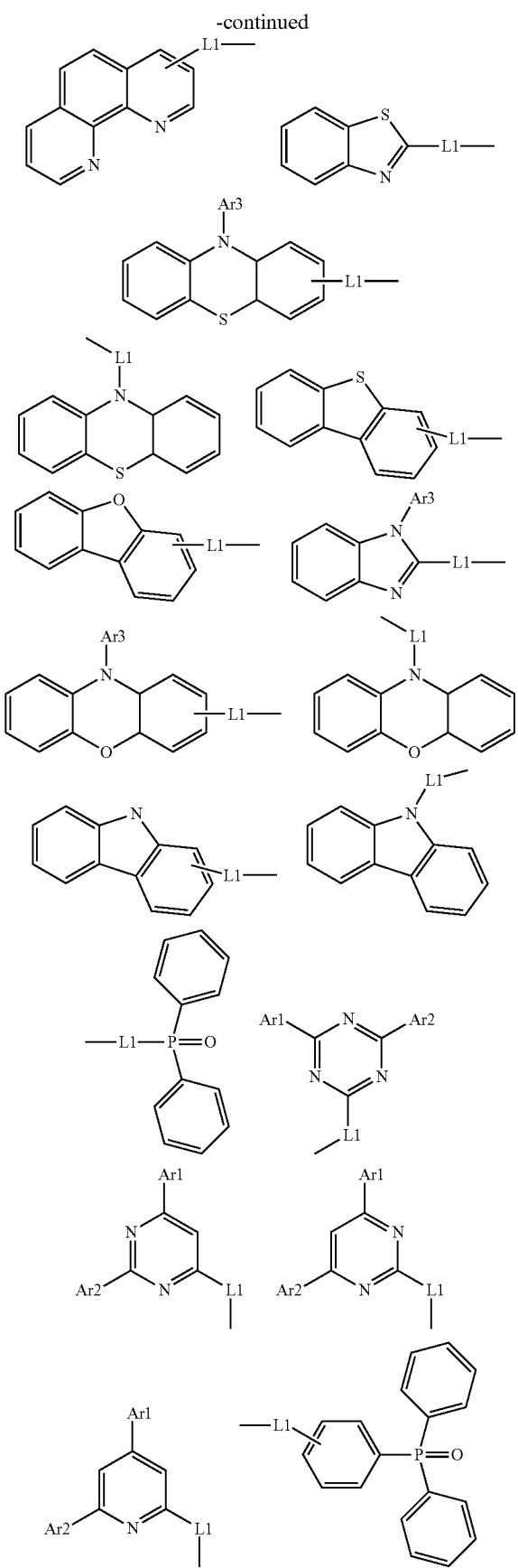

wherein, in the structural formulae,

Ar1 to Ar3 are the same as or different from each other, and each independently a substituted or unsubstituted aryl group; a substituted or unsubstituted heterocyclic group; a substituted or unsubstituted arylamine group; a substituted or unsubstituted heteroarylamine group; or a substituted or unsubstituted arylheteroarylamine group, L1 is a direct bond; a substituted or unsubstituted arylene group; or a substituted or unsubstituted heteroarylene group, and the structures are unsubstituted or substituted with one or more substituents selected from the group consisting of deuterium; a halogen group; a nitrile group; a nitro group; a hydroxyl group; a carbonyl group; an ester group; an imide group; a substituted or unsubstituted amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

5. The compound of claim 1, wherein L is a direct bond; or selected from among the following structures:

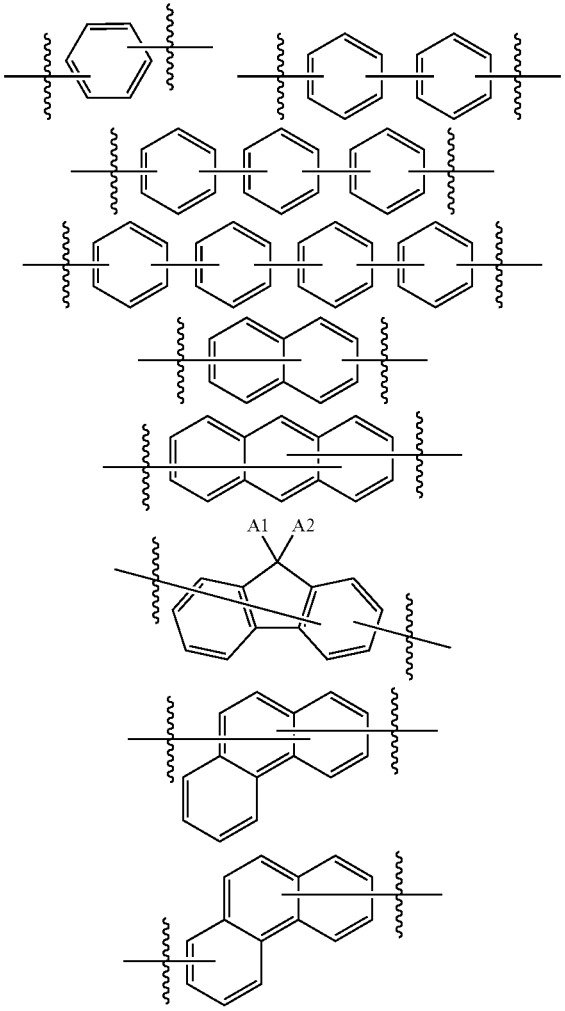

-continued

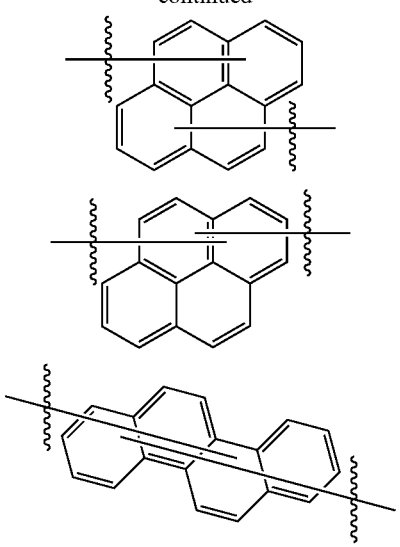

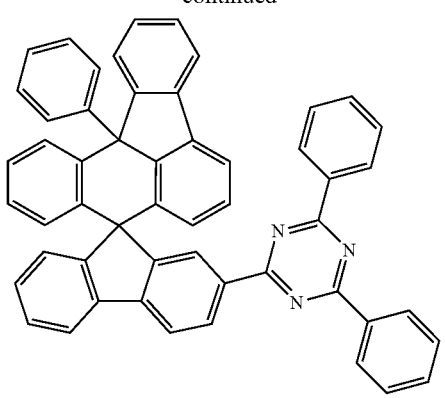

wherein, in the structural formulae,

A1 and A2 are the same as or different from each other, and each independently hydrogen; a substituted or unsubstituted alkyl group; a substituted or unsubstituted aryl group; or a substituted or unsubstituted heterocyclic group, or bond to each other to form a substituted or unsubstituted ring, and the structures are unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

6. The compound of claim 1, wherein the compound of Chemical Formula 1 is any one selected from among the following structural formulae:

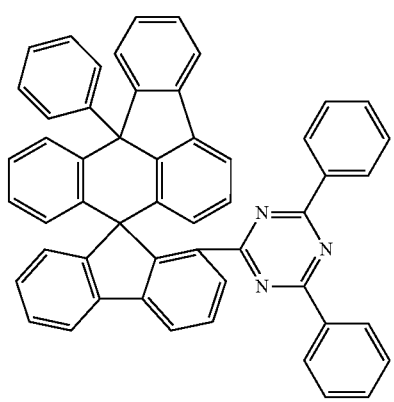

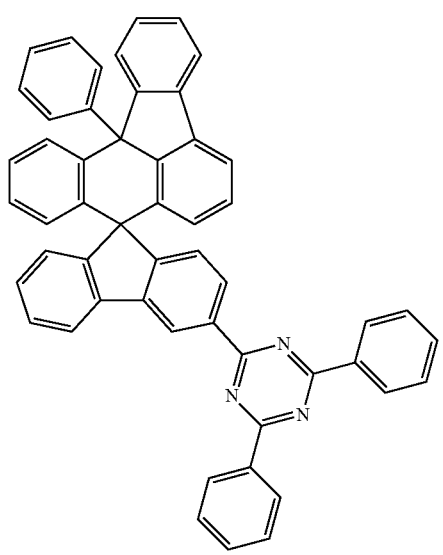

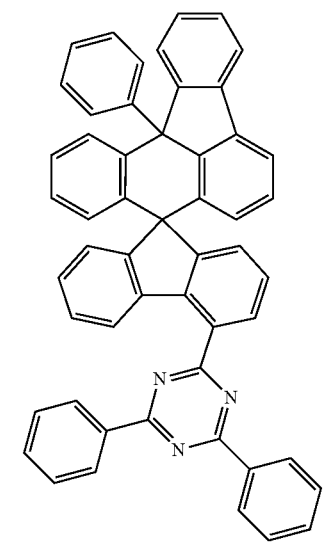

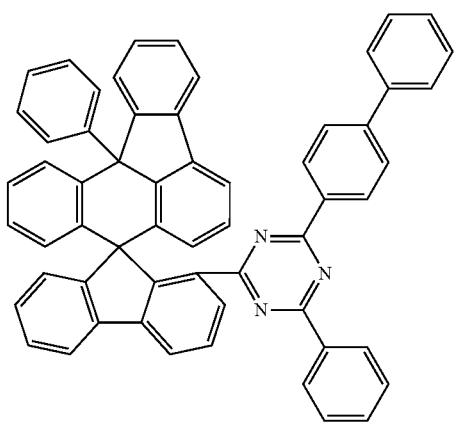
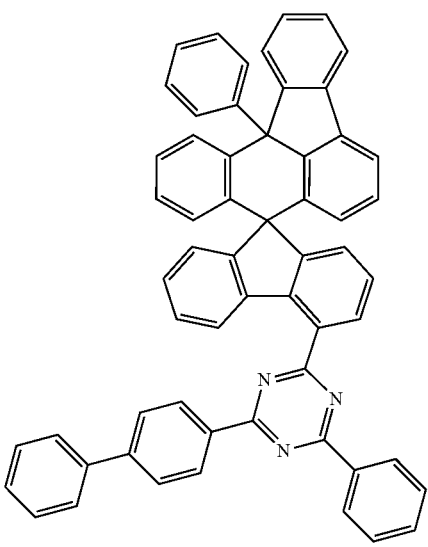
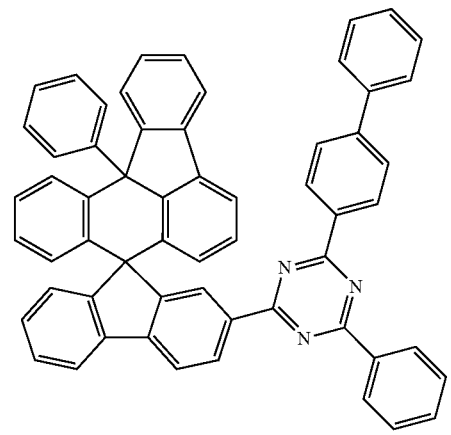
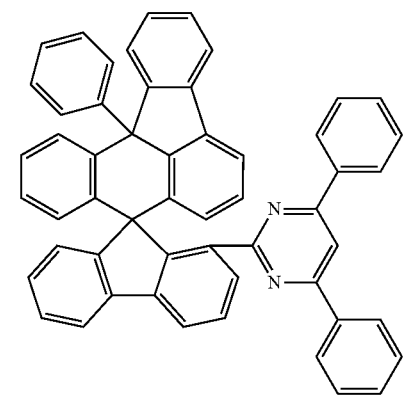
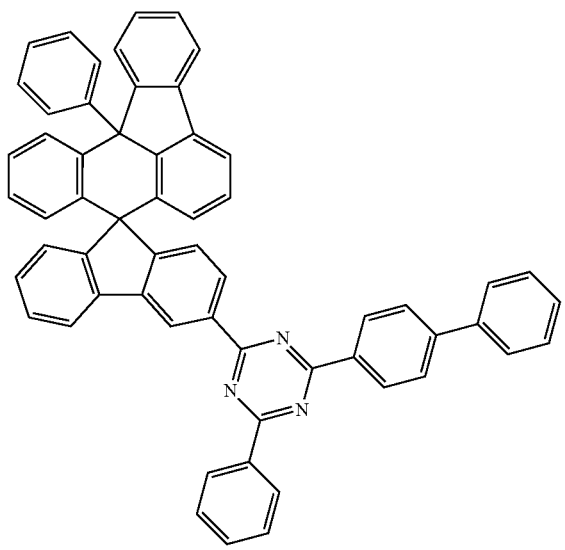
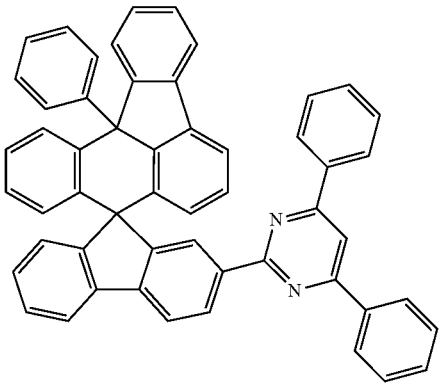

139
-continued
140
-continued
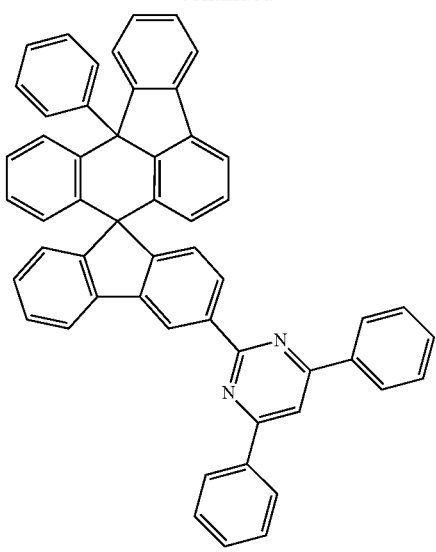
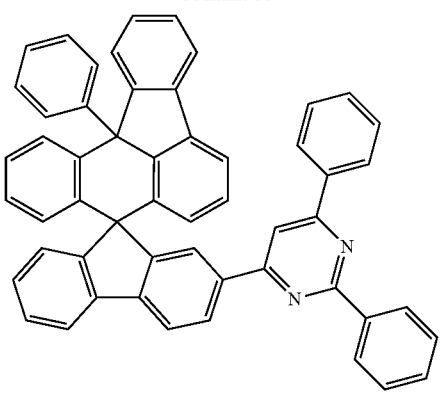
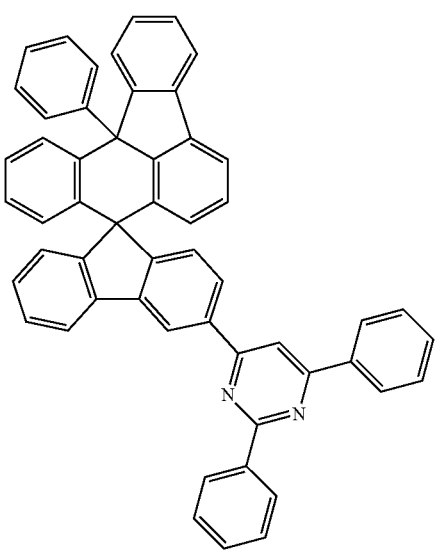
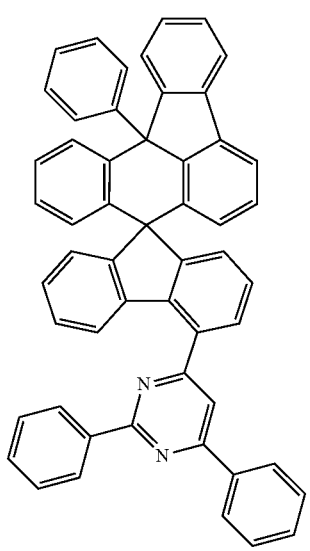

-continued
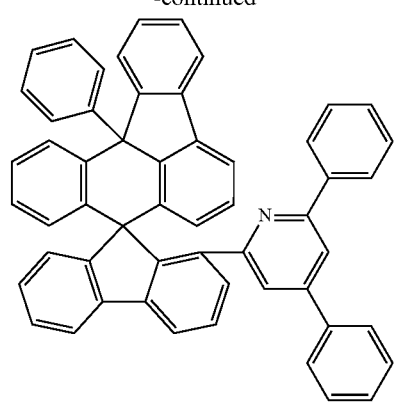
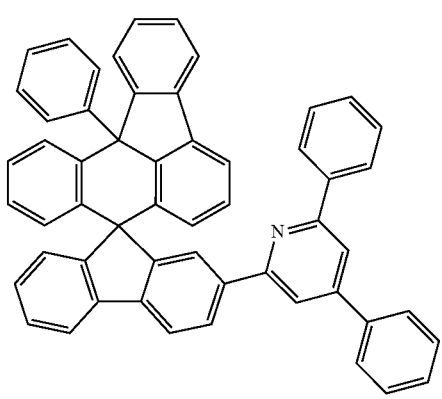
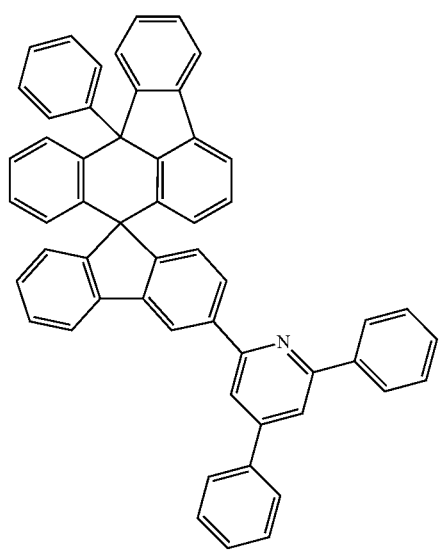
-continued
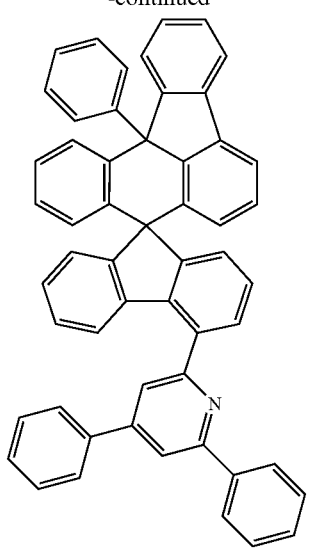
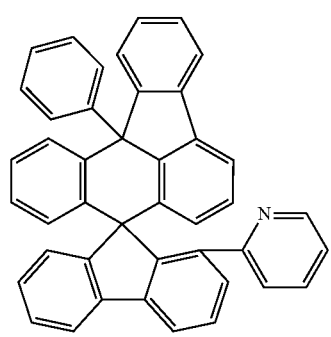
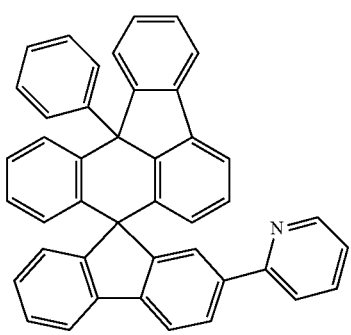
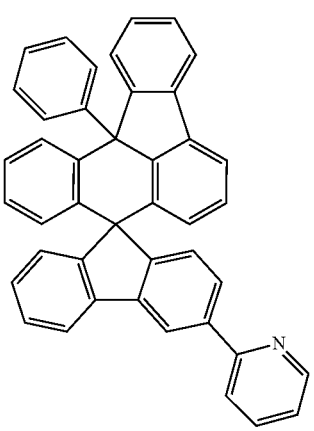

143
-continued
144
-continued
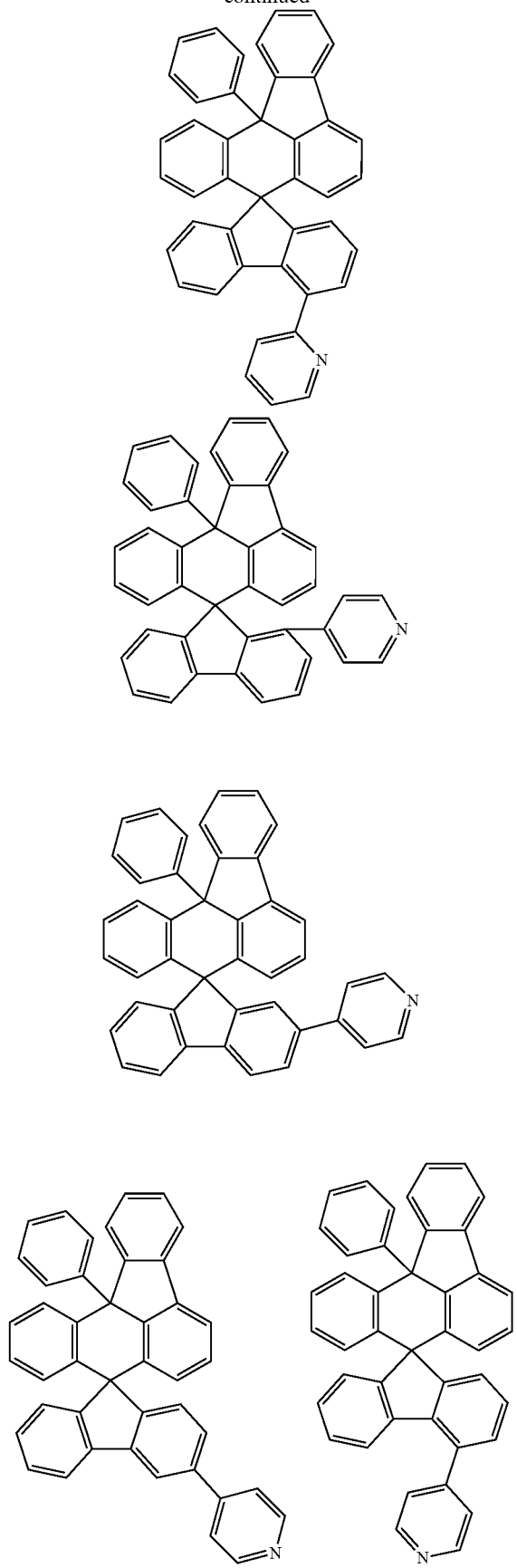
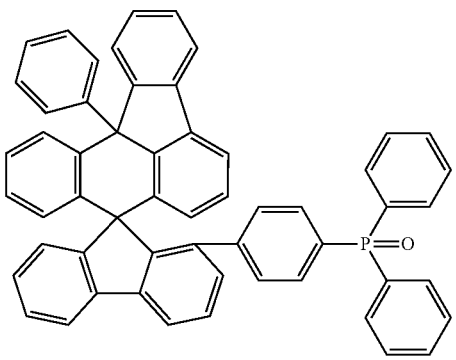
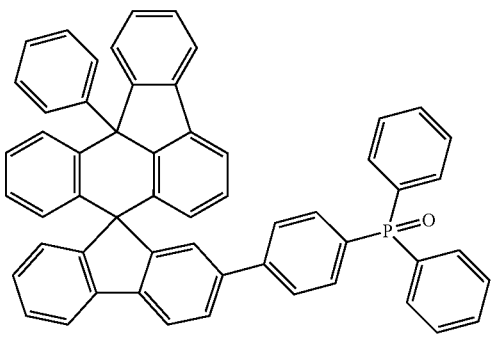
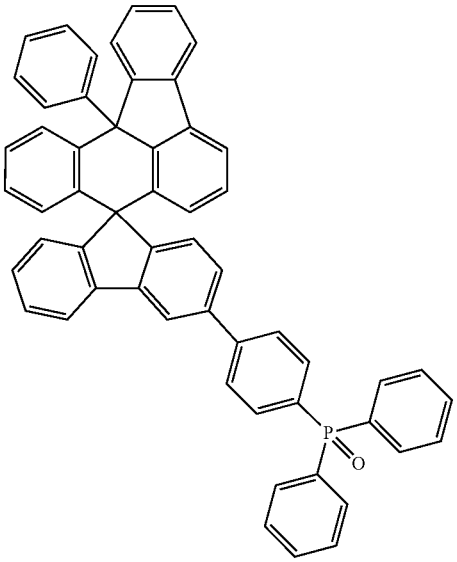

145
-continued
146
-continued
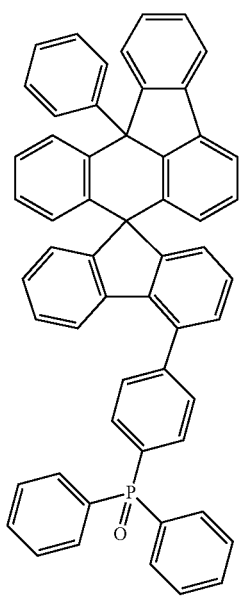
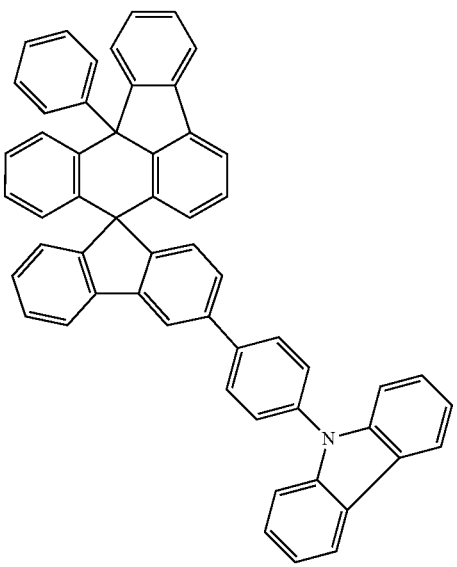
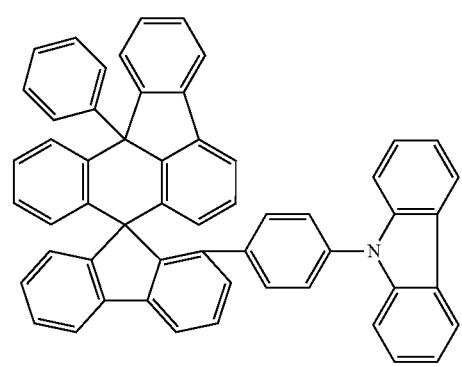
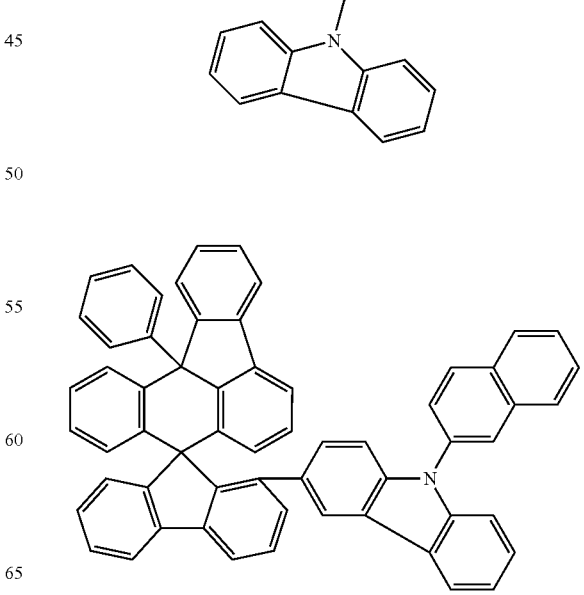

147
-continued
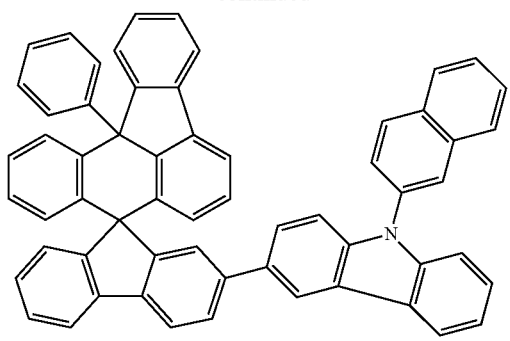
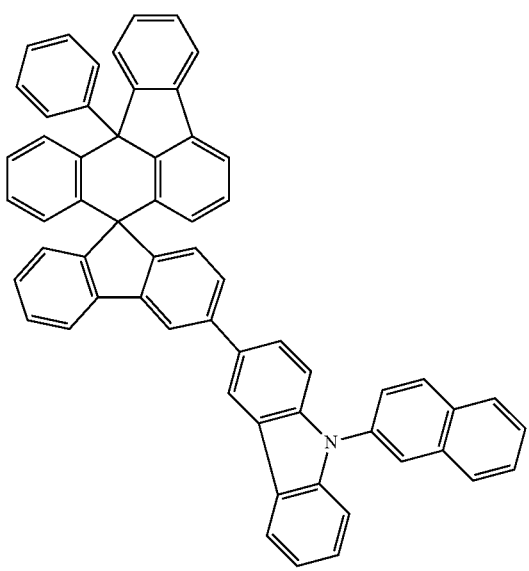
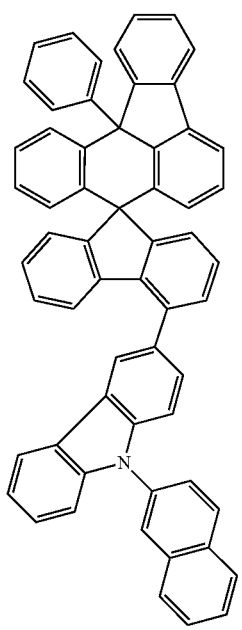
148
-continued
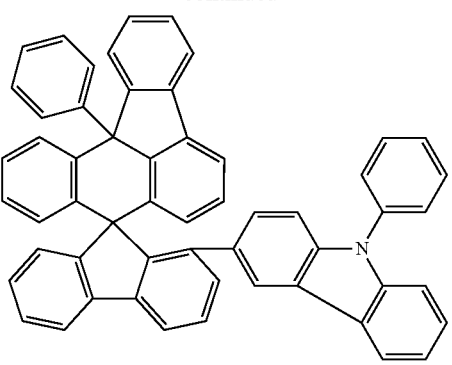
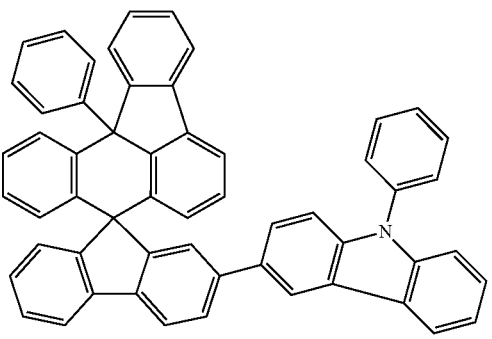
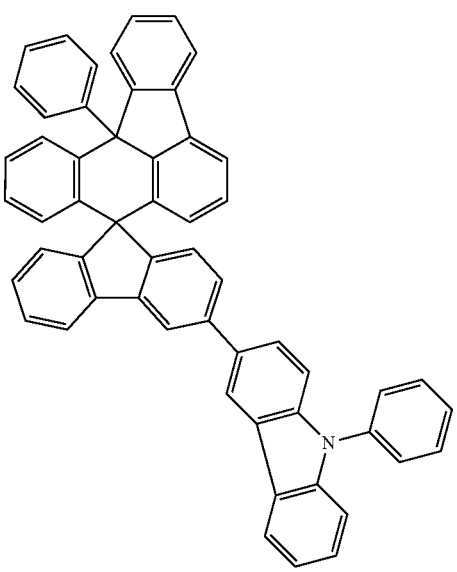

-continued
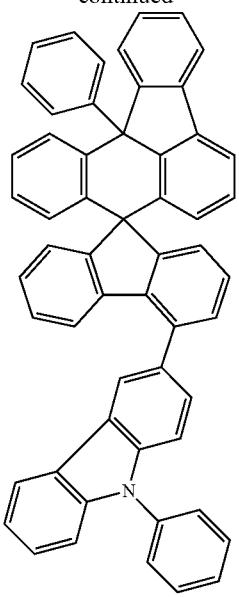
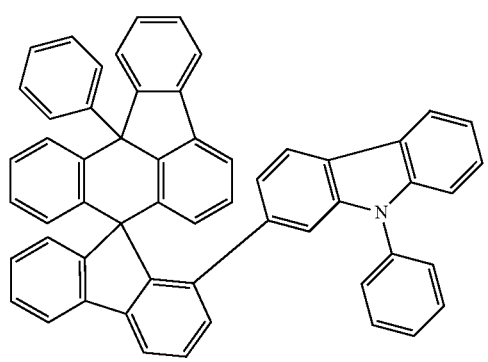
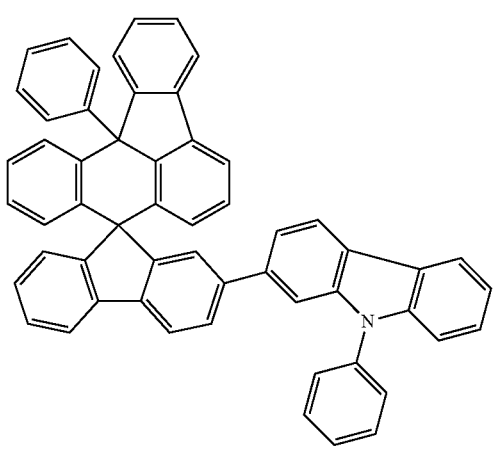
-continued
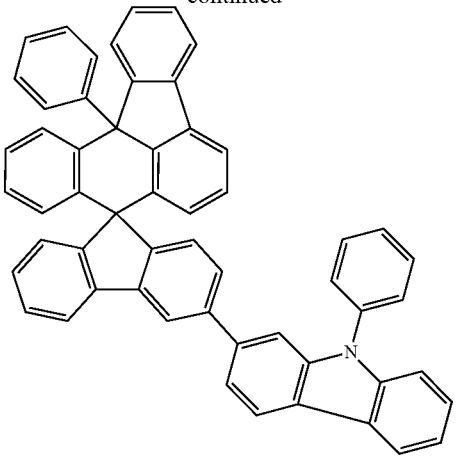
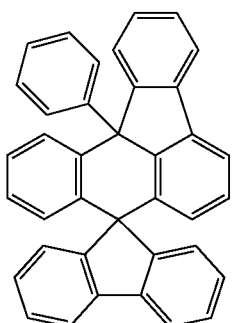
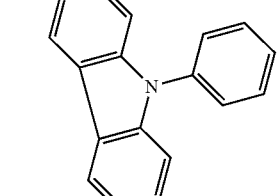
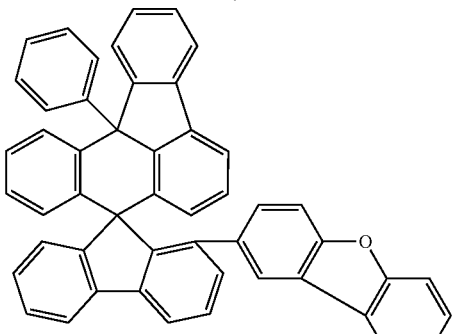
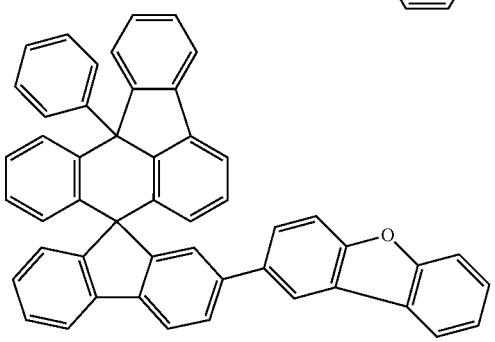

151
-continued
152
-continued
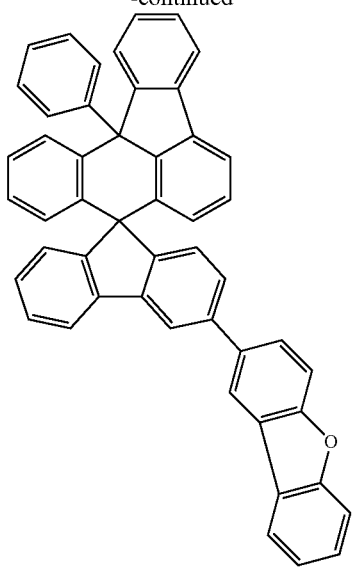
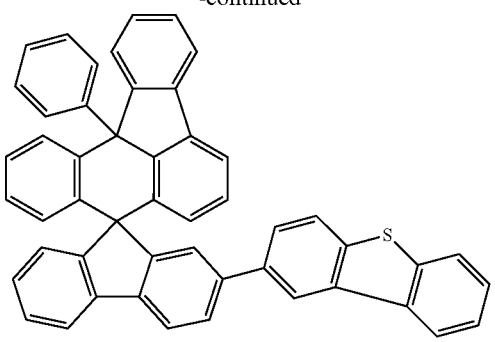
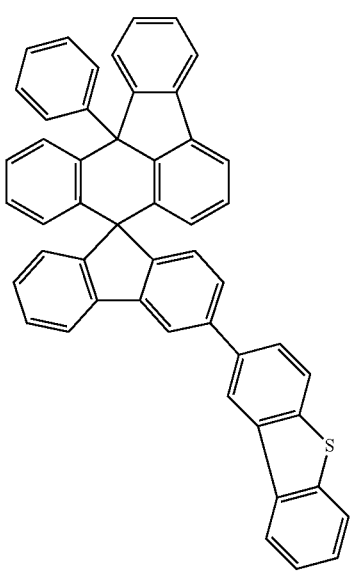
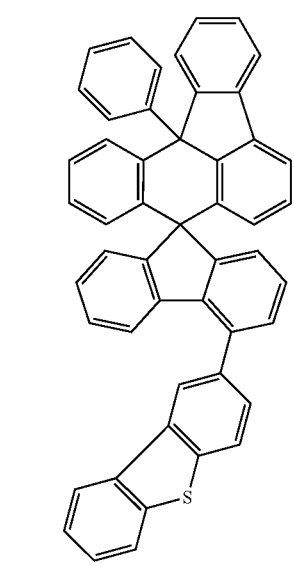

153
-continued
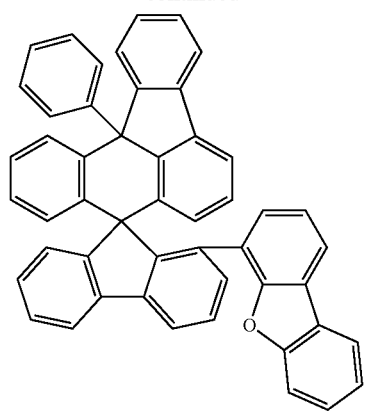
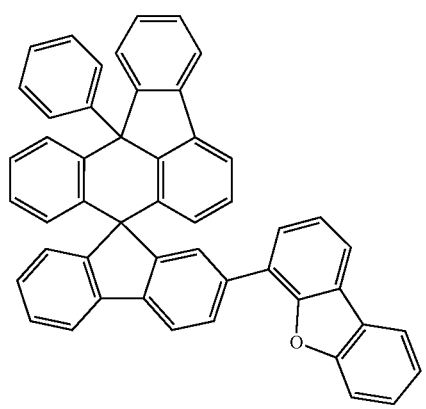
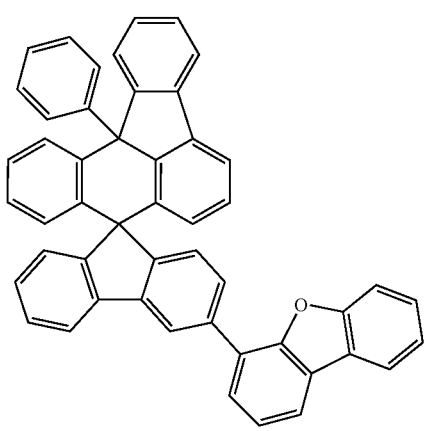
154
-continued
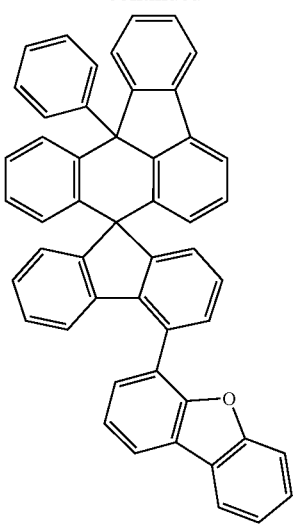
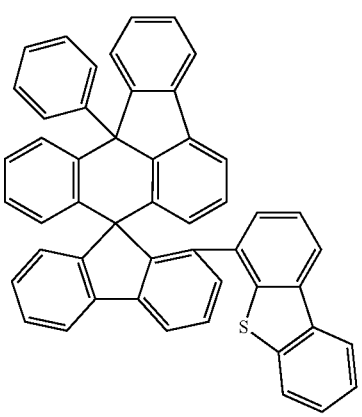
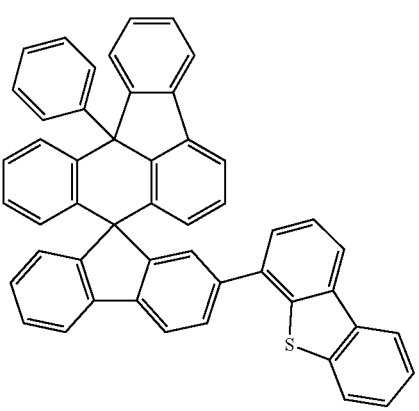

-continued
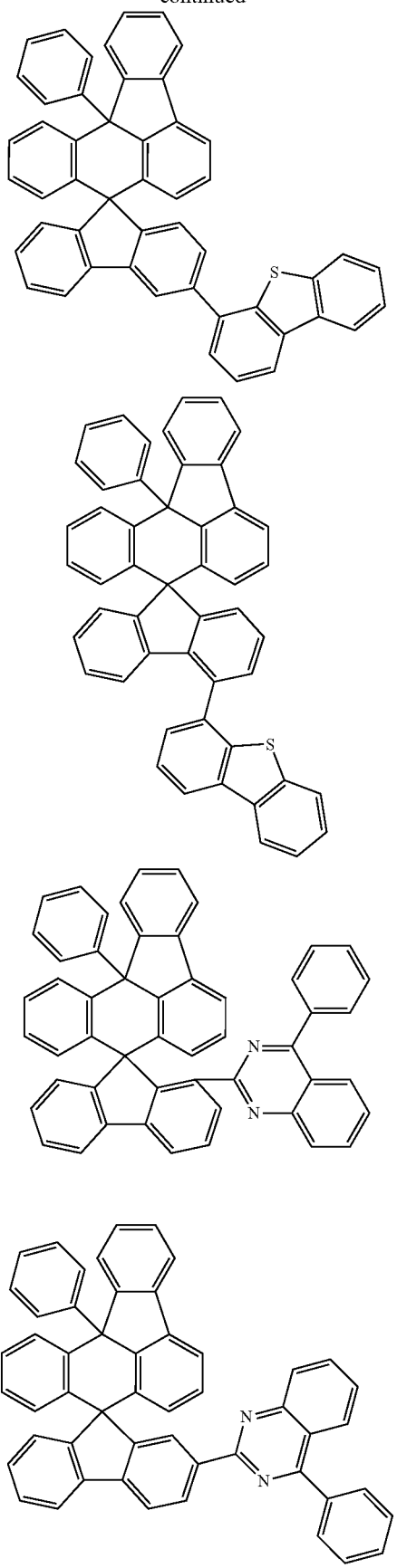
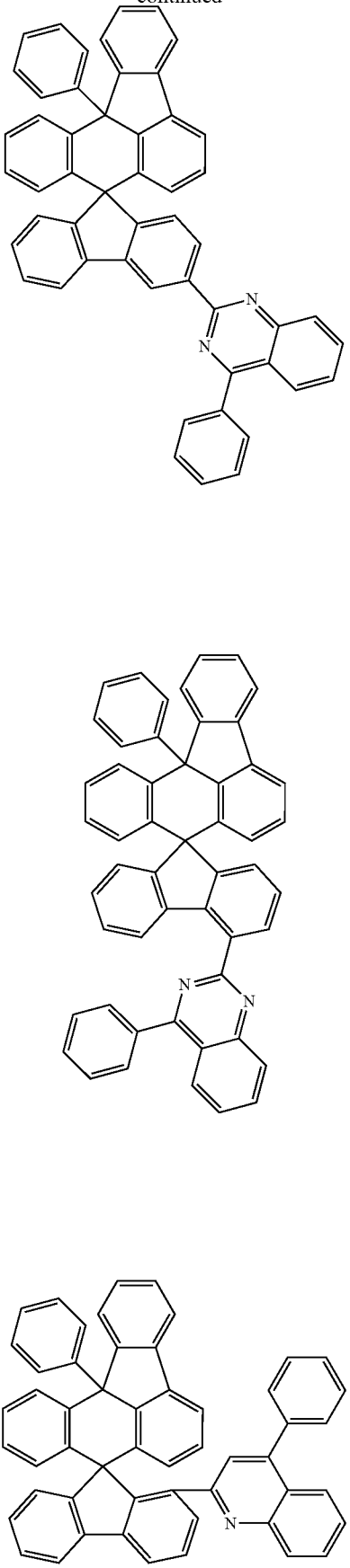

157
-continued
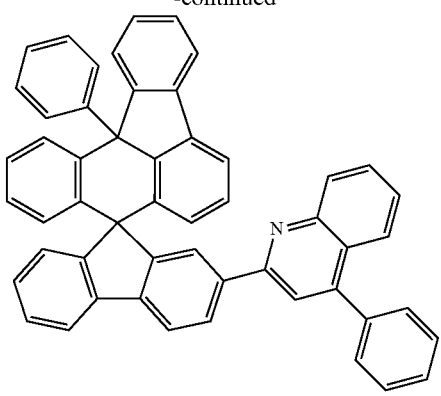
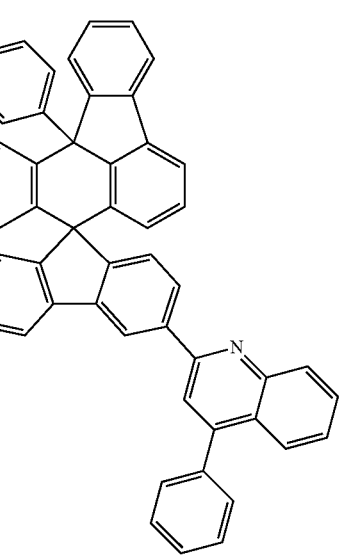
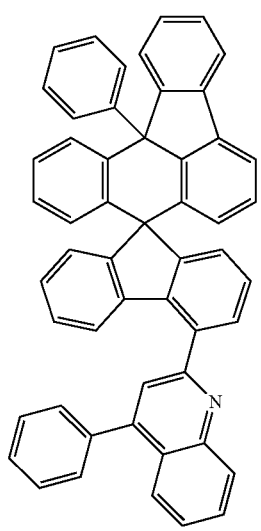
158
-continued
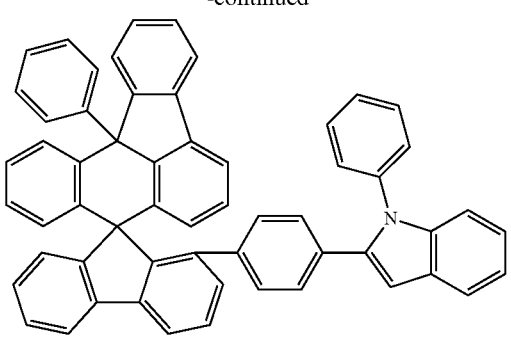
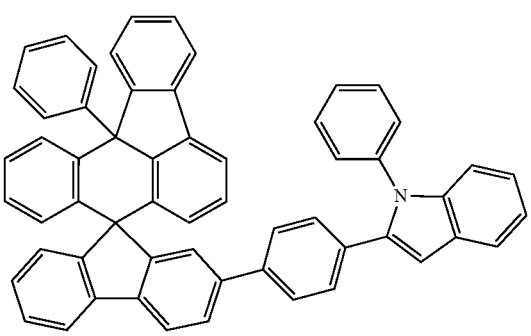
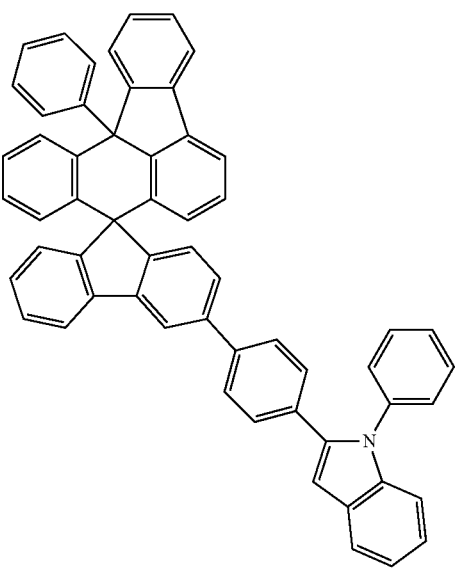

159
-continued
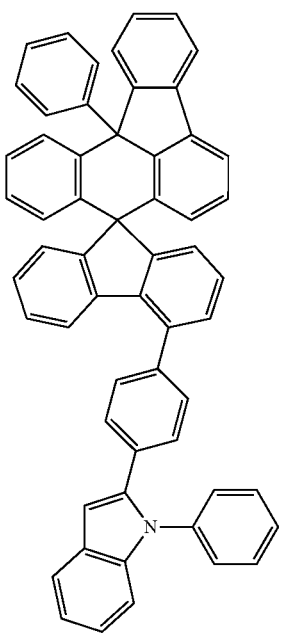
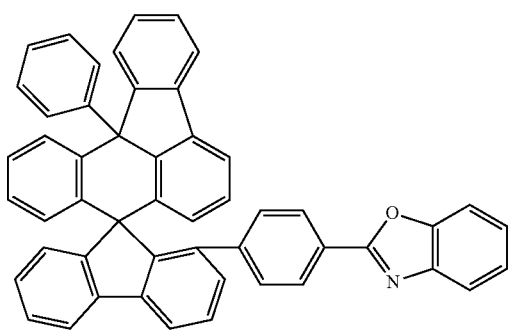
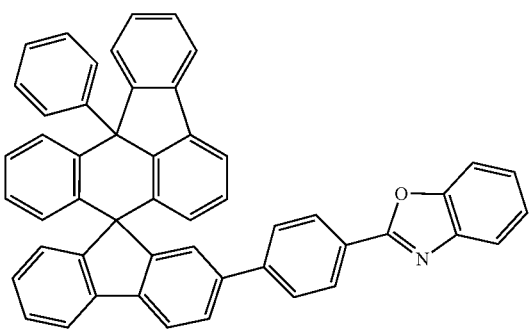
160
-continued
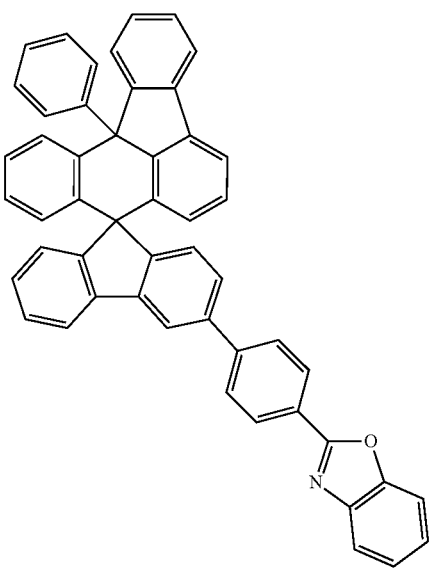
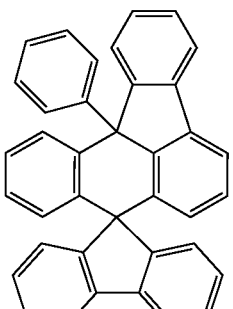
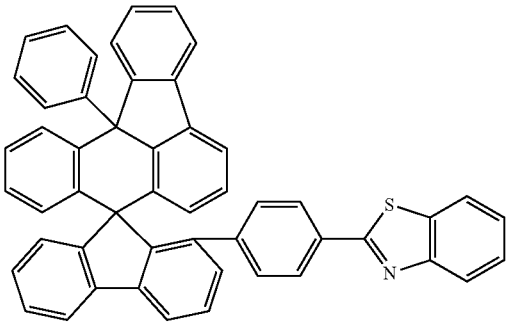

161
-continued
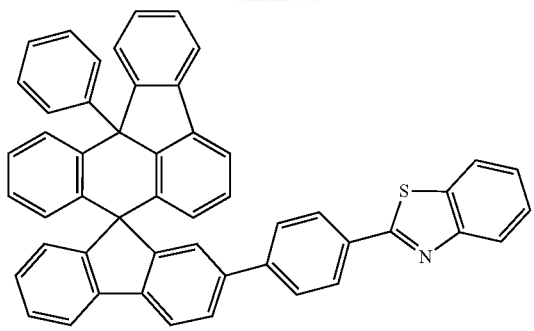
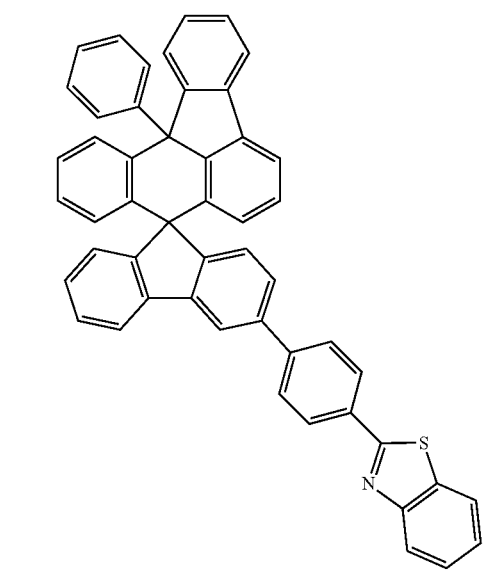
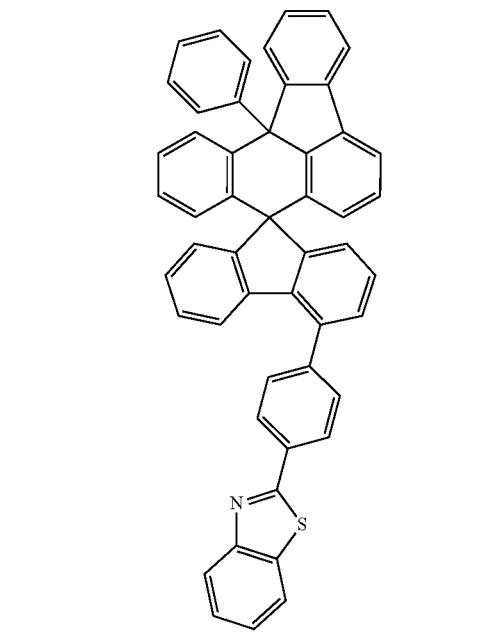
162
-continued
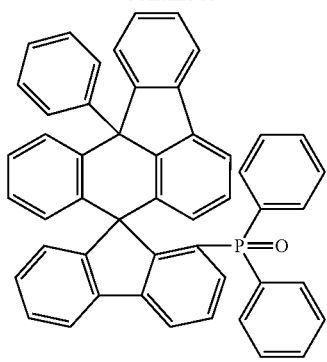
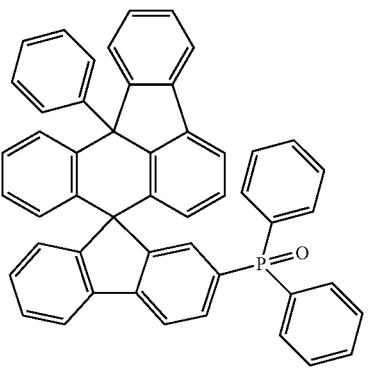
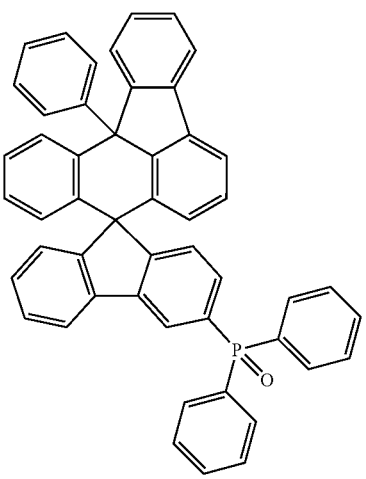
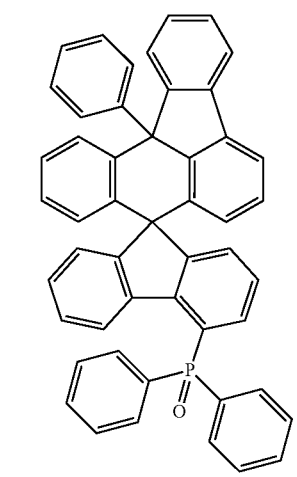

163
-continued
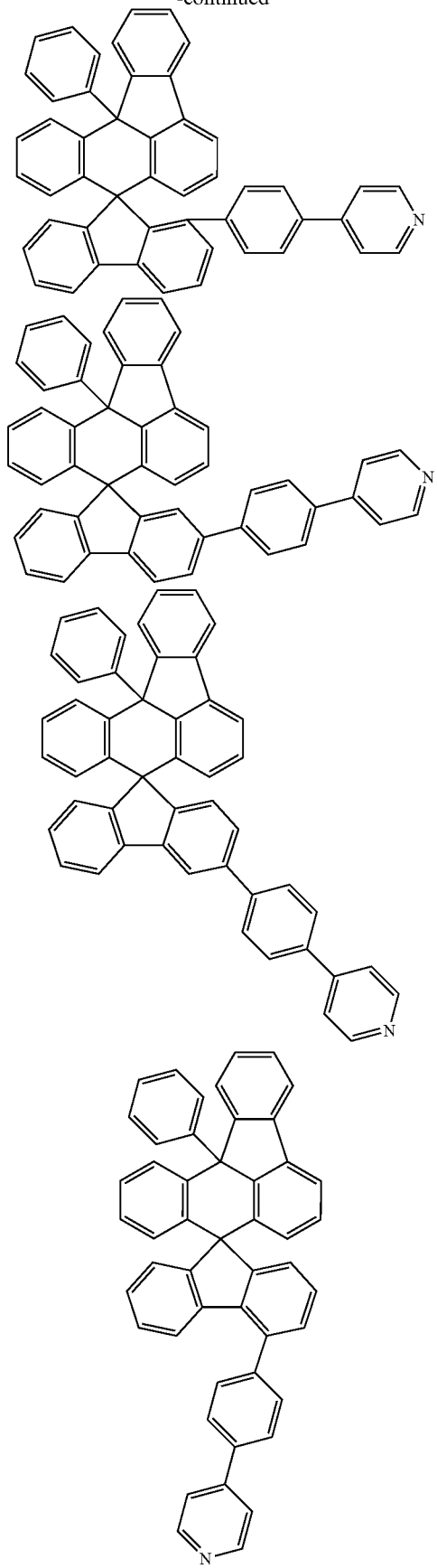
164
-continued
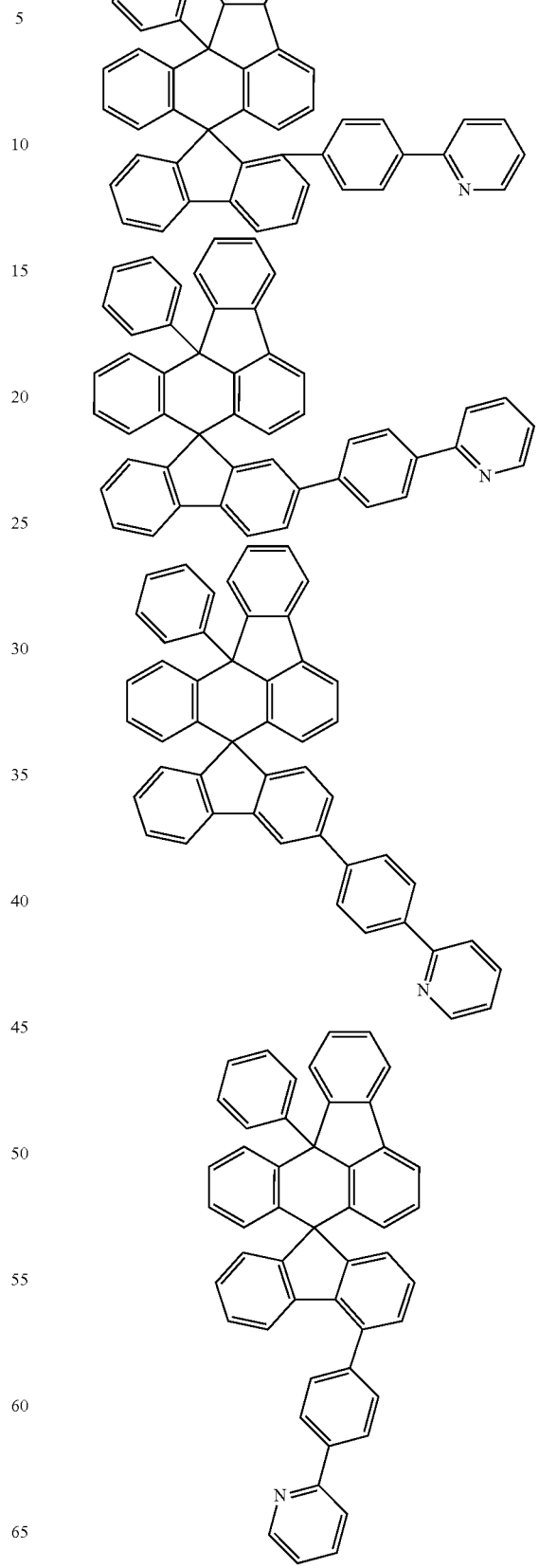

165
-continued
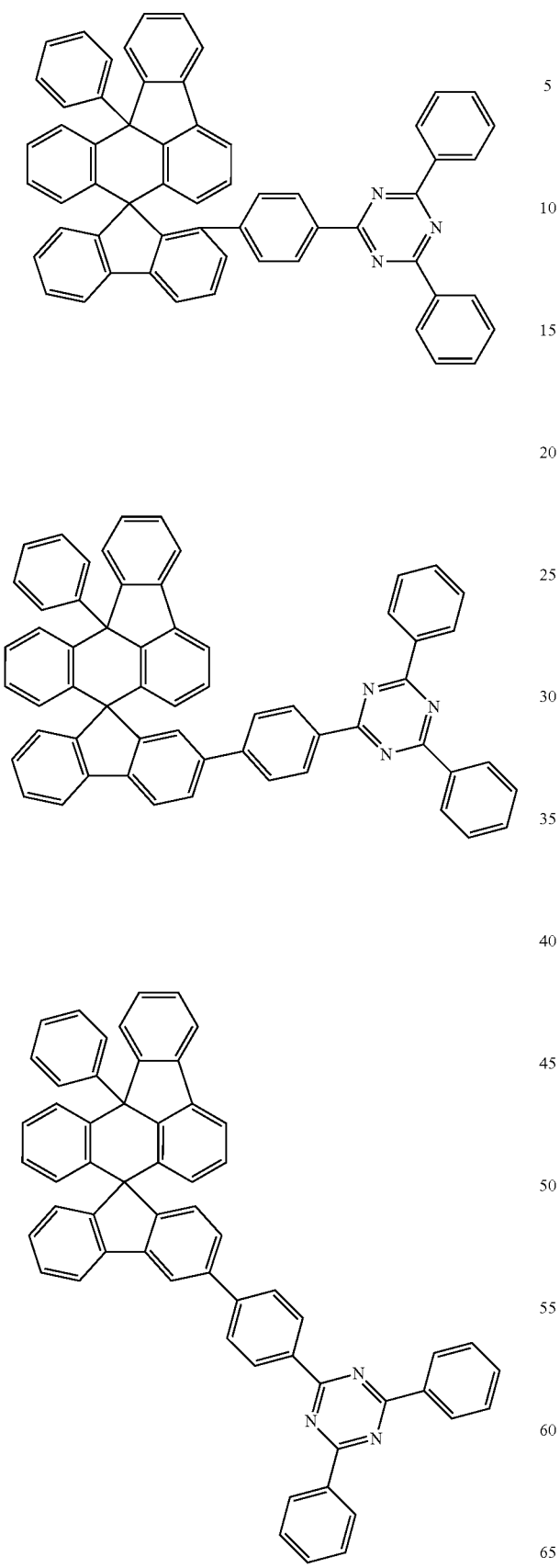
166
-continued
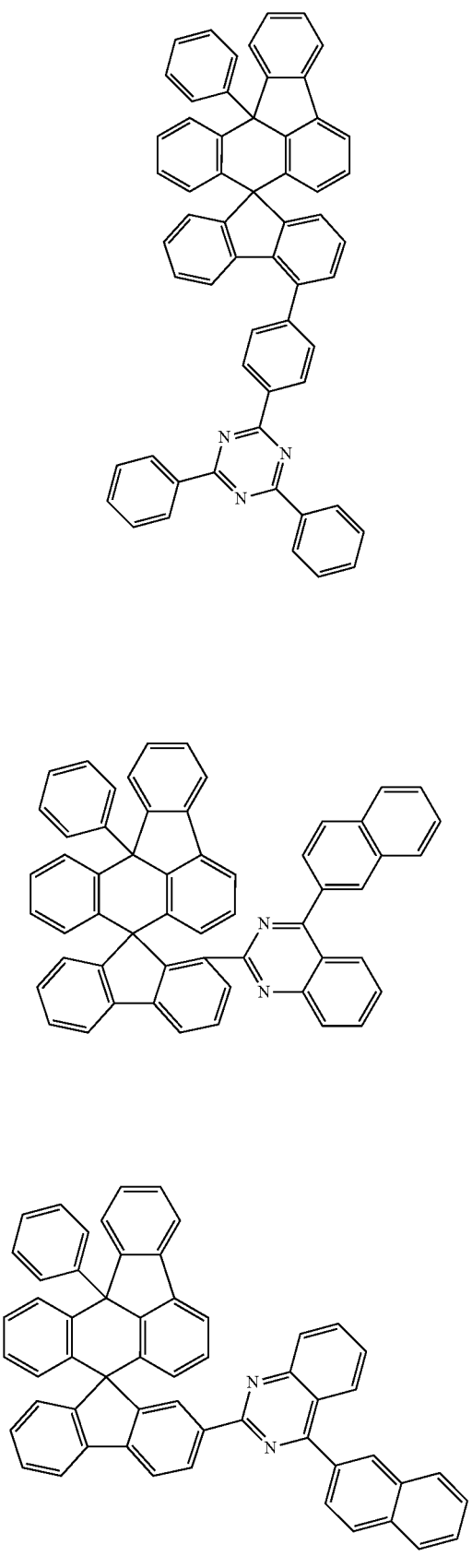

167
-continued
168
-continued
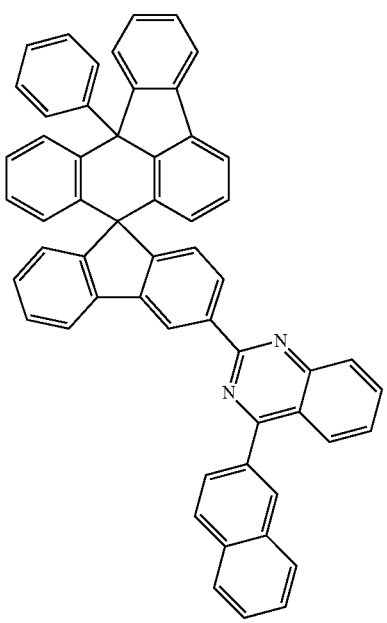
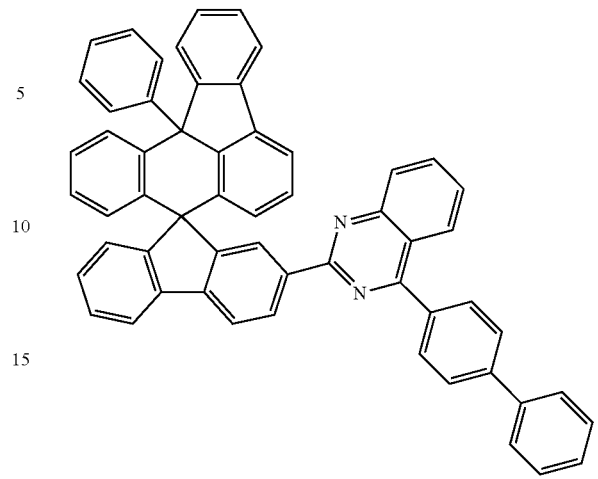
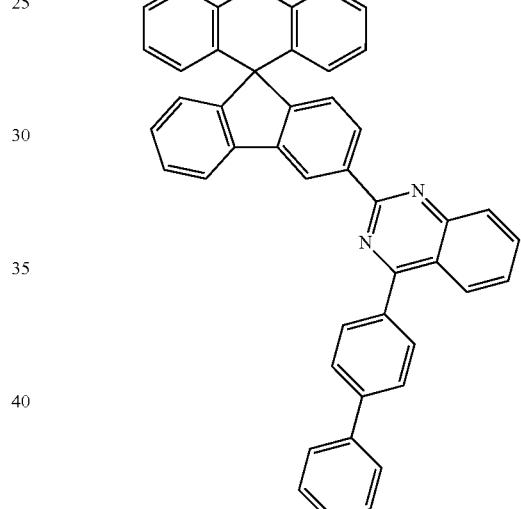
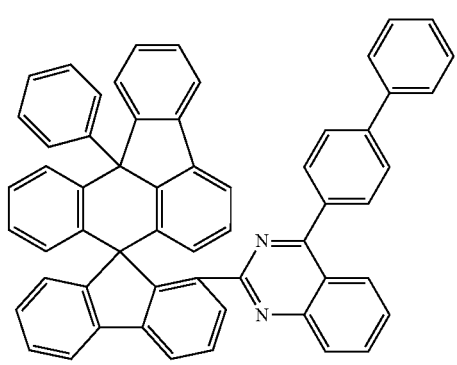
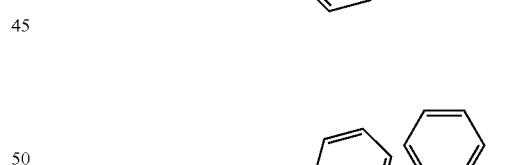
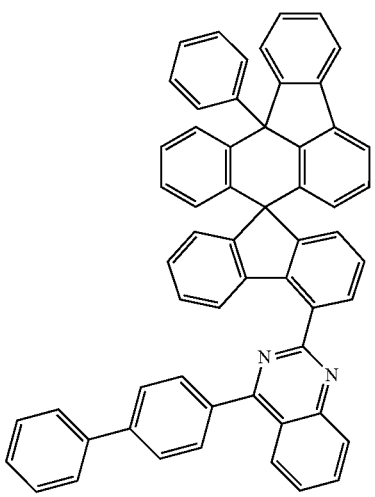

169
-continued
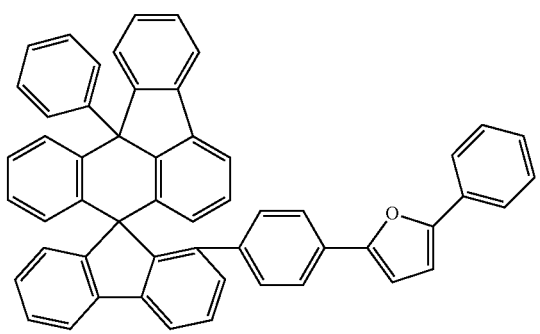
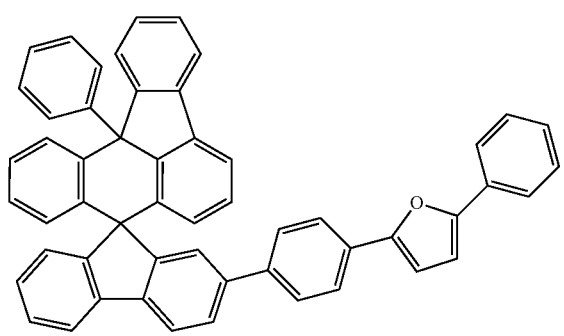
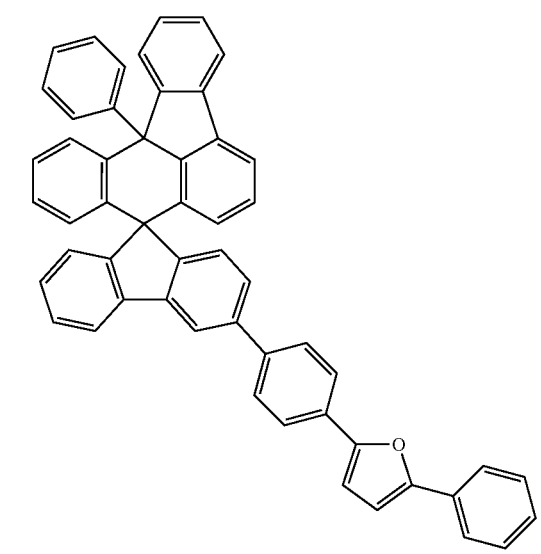
170
-continued
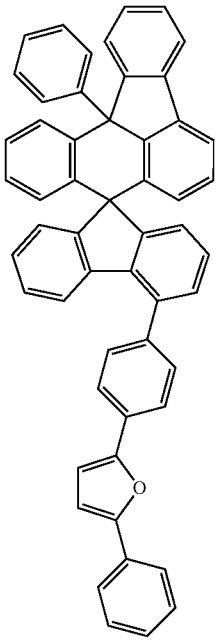
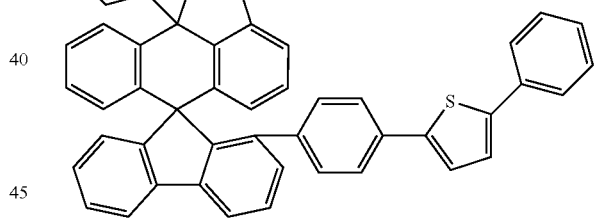
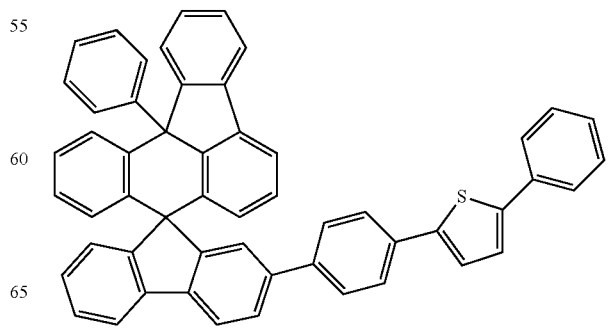

171
-continued
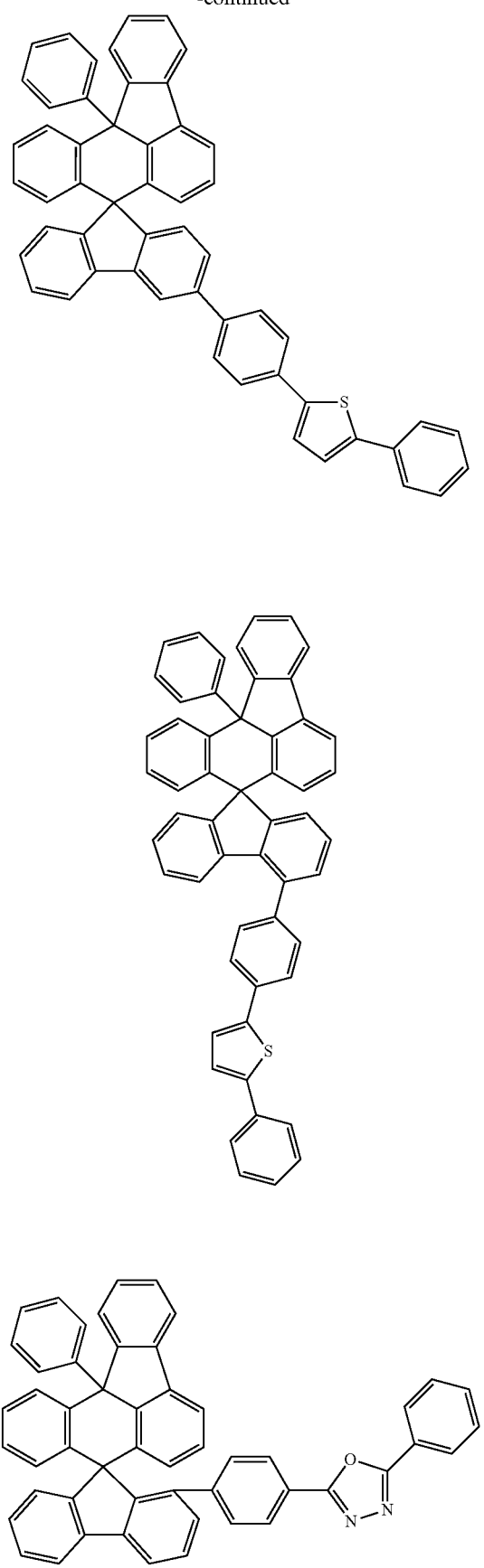
172
-continued
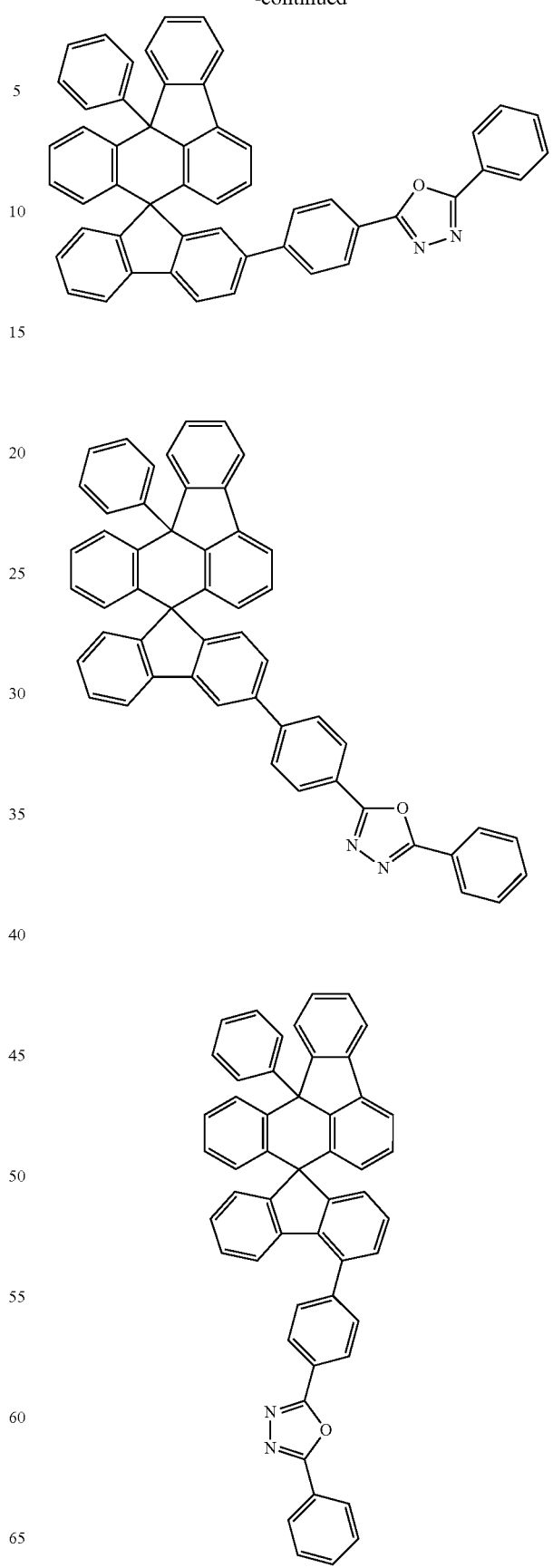

173
-continued
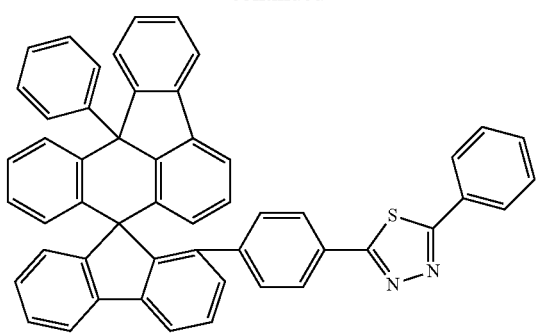
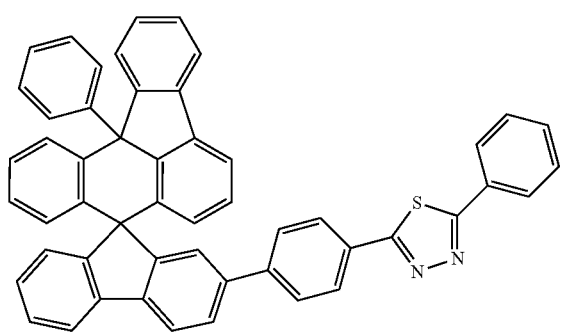
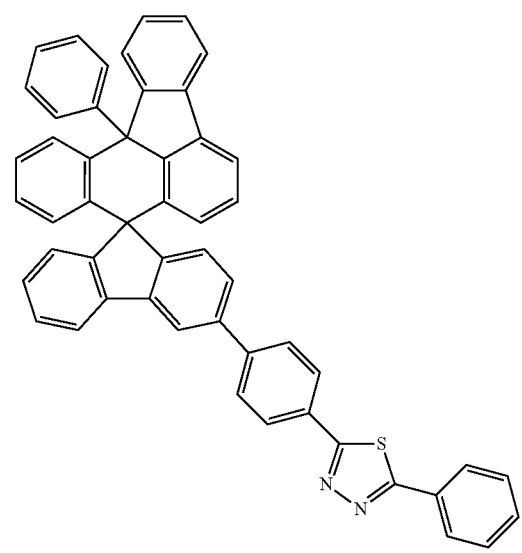
174
-continued
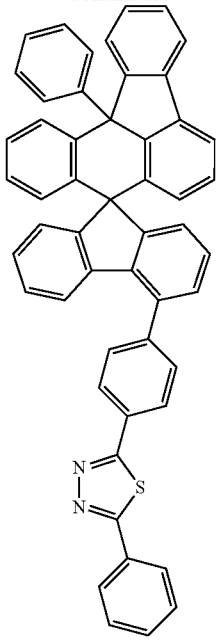
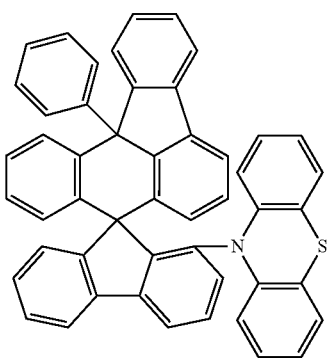
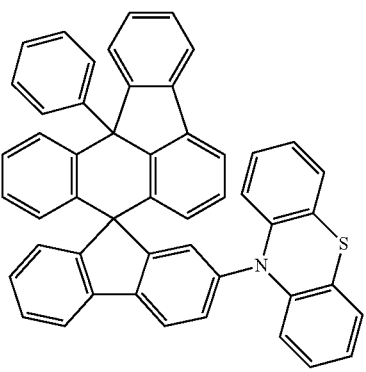

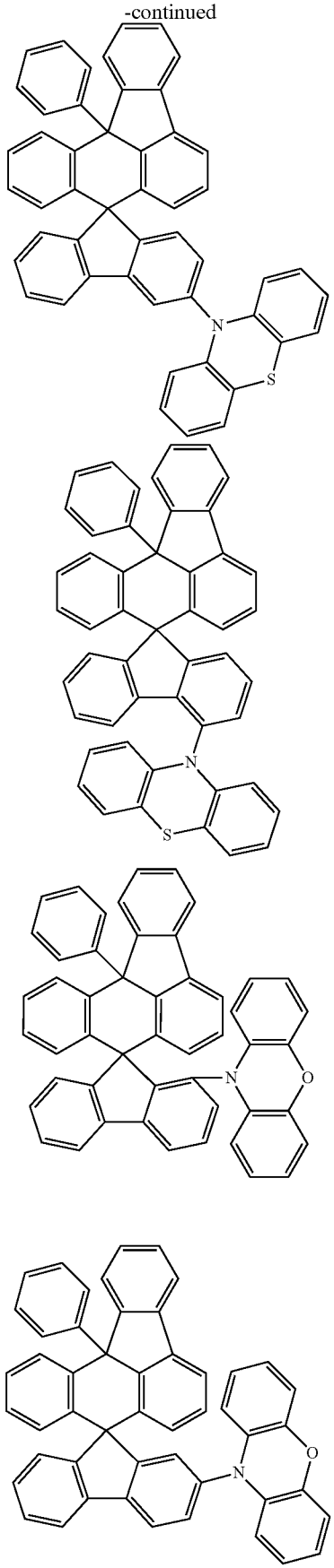

177
-continued
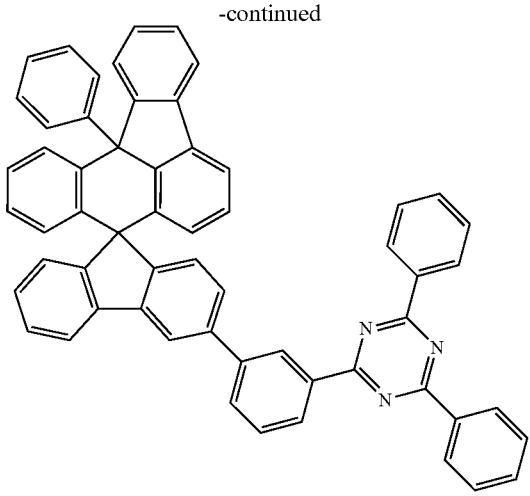
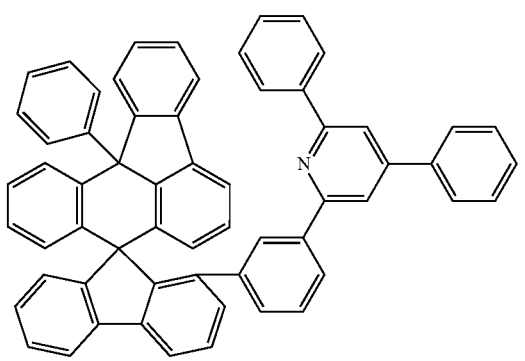
178
-continued
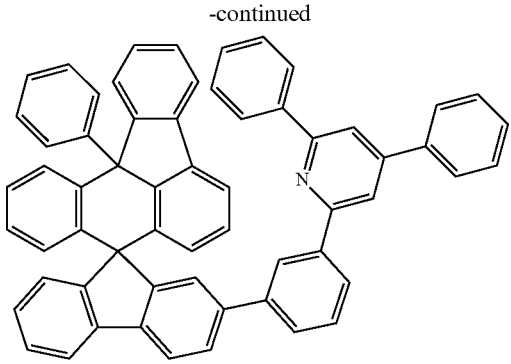
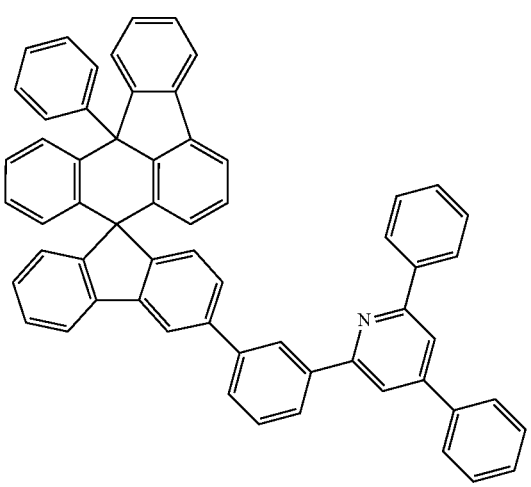
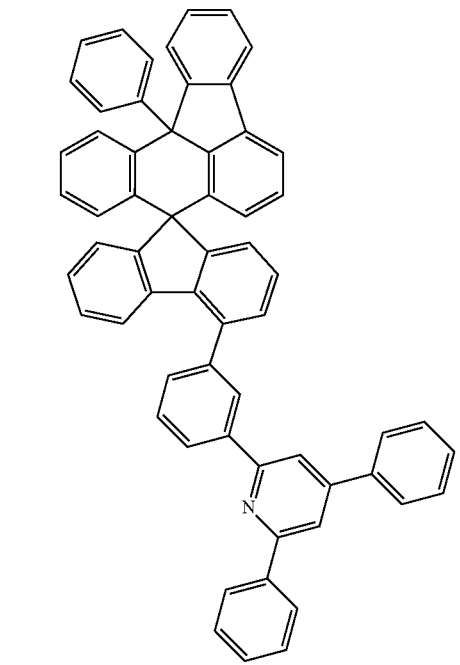

-continued
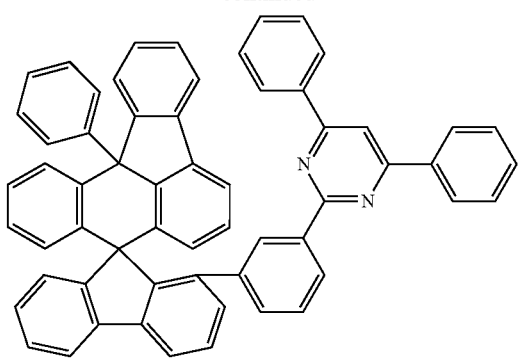
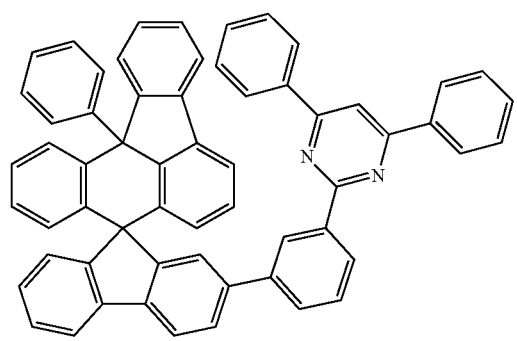
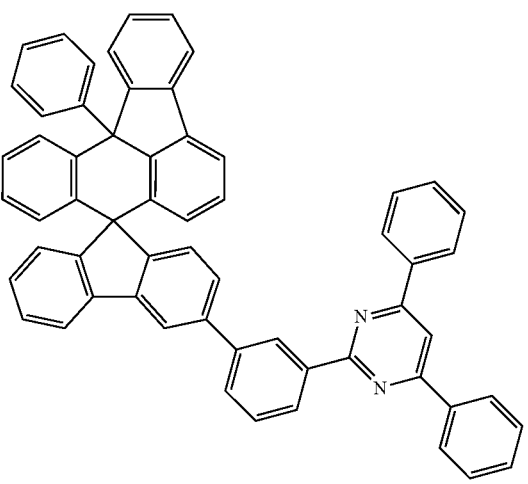
-continued
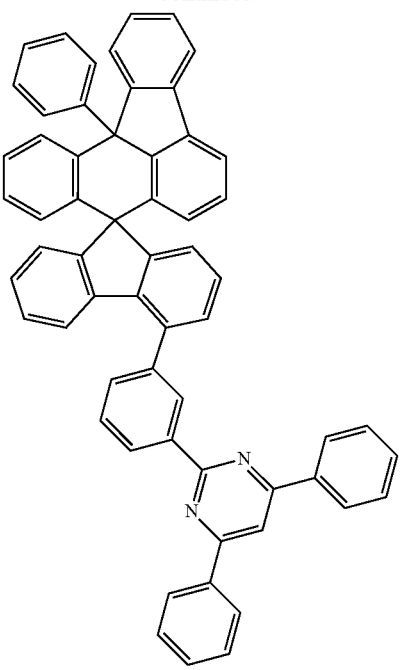
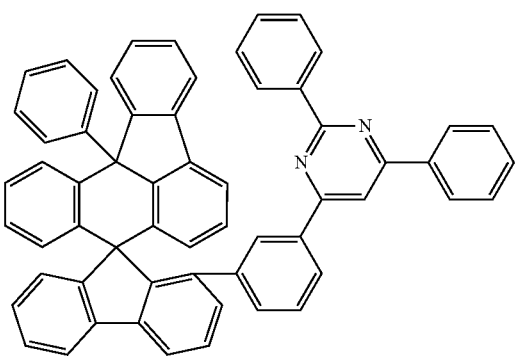
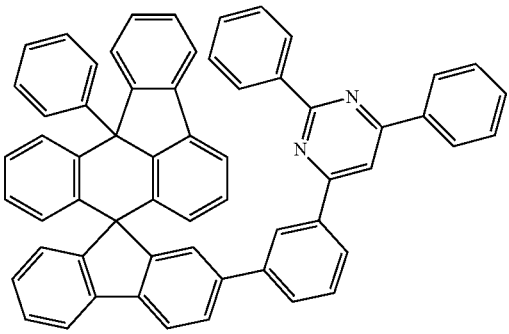

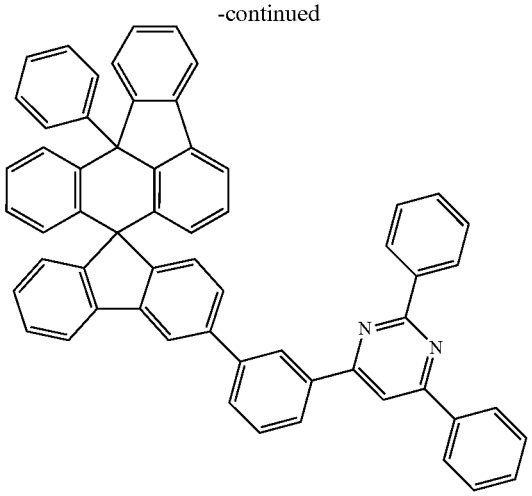

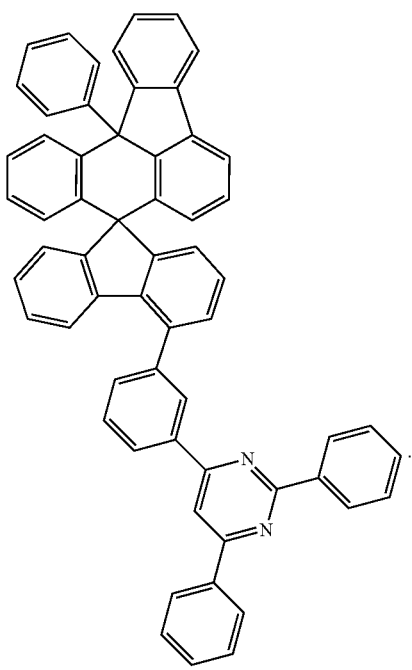

7. An organic light emitting device comprising:
a first electrode;
a second electrode provided opposite to the first electrode; and
one or more organic material layers provided between the first electrode and the second electrode,
wherein one or more layers of the organic material layers include the compound of claim 1.

8. The organic light emitting device of claim 7, wherein the organic material layer includes a light emitting layer, and the light emitting layer includes the compound.

9. The organic light emitting device of claim 8, wherein the light emitting layer further includes a light emitting dopant.

10. The organic light emitting device of claim 7, wherein the organic material layer includes an electron injection layer, an electron transfer layer, or a layer carrying out electron transfer and electron injection at the same time, and the electron injection layer, the electron transfer layer, or the layer carrying out electron transfer and electron injection at the same time includes the compound.

11. The organic light emitting device of claim 10, wherein the electron transfer layer further includes an n-type dopant.

12. The organic light emitting device of claim 7, wherein the organic material layer includes a hole injection layer, a hole transfer layer, a layer carrying out hole injection and transfer at the same time, or an electron suppression layer, and the hole injection layer, the hole transfer layer, the layer carrying out hole injection and transfer at the same time, or the electron suppression layer includes the compound.

13. The organic light emitting device of claim 7, wherein the organic material layer includes a light emitting layer, and the light emitting layer includes a compound represented by the following Chemical Formula 1-A:

[Chemical Formula 1-A]

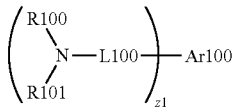

wherein, in Chemical Formula 1-A,
z1 is an integer of 1 or greater, and when z1 is an integer of 2 or greater, structures in the parentheses are the same as or different from each other,
Ar100 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group,
L100 is a direct bond; a substituted or unsubstituted arylene group; or a substituted or unsubstituted heteroarylene group, and
R100 and R101 are the same as or different from each other, and each independently a substituted or unsubstituted aryl group; a substituted or unsubstituted alkyl group; a substituted or unsubstituted silyl group; a substituted or unsubstituted arylalkyl group; or a substituted or unsubstituted heterocyclic group, or bond to each other to form a substituted or unsubstituted ring.

14. The organic light emitting device of claim 13, wherein z1 is 2, Ar100 is a divalent pyrene group, L100 is a direct bond, and R100 and R101 are the same as or different from each other and each independently an aryl group unsubstituted or substituted with an alkylgermanium group.

15. The organic light emitting device of claim 7, wherein the organic material layer includes a light emitting layer, and the light emitting layer includes a compound represented by the following Chemical Formula 1-B:

[Chemical Formula 1-B]

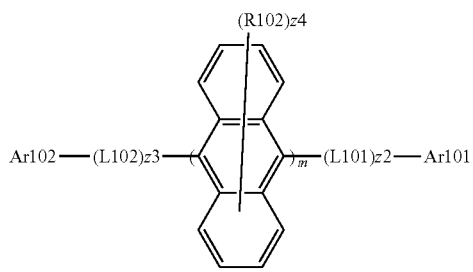

wherein, in Chemical Formula 1-B,
Ar101 and Ar102 are the same as or different from each other, and each independently a substituted or unsubstituted aryl group; or a substituted or unsubstituted heterocyclic group,
L101 and L102 are the same as or different from each other, and each independently a direct bond; a substituted or unsubstituted arylene group; or a substituted or unsubstituted heteroarylene group,
R102 is hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group,
z2 and z3 are the same as or different from each other and each independently an integer of 1 or 2, z4 is an integer of 0 to 8, and when z2 to z4 are 2 or greater, substituents in the parentheses are the same as or different from each other, and
m is an integer of 1 or greater, and when m is an integer of 2 or greater, substituents in the parentheses are the same as or different from each other.

16. The organic light emitting device of claim 15, wherein Ar101 is a 2-naphthyl group, Ar102 is a phenyl group, L101 is a phenylene group, L102 is a direct bond, z2 is 1, R102 is hydrogen, and m is 1.

17. The organic light emitting device of claim 13, wherein the light emitting layer includes a compound represented by the following Chemical Formula 1-B:

[Chemical Formula 1-B]

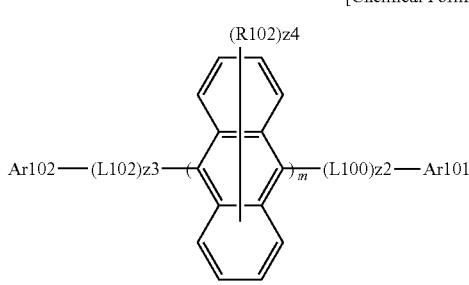

wherein, in Chemical Formula 1-B,
Ar101 and Ar102 are the same as or different from each other, and each independently a substituted or unsubstituted aryl group; or a substituted or unsubstituted heterocyclic group,
L101 and L102 are the same as or different from each other, and each independently a direct bond; a substituted or unsubstituted arylene group; or a substituted or unsubstituted heteroarylene group,
R102 is hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group,
z2 and z3 are the same as or different from each other and each independently an integer of 1 or 2, z4 is an integer of 0 to 8, and when z2 to z4 are 2 or greater, substituents in the parentheses are the same as or different from each other, and
m is an integer of 1 or greater, and when m is an integer of 2 or greater, substituents in the parentheses are the same as or different from each other.

* * * * *